(12) United States Patent
Lichter et al.

(10) Patent No.: US 8,496,957 B2
(45) Date of Patent: Jul. 30, 2013

(54) CONTROLLED RELEASE AURIS SENSORY CELL MODULATOR COMPOSITIONS AND METHODS FOR THE TREATMENT OF OTIC DISORDERS

(75) Inventors: Jay Lichter, Rancho Santa Fe, CA (US); Benedikt Vollrath, San Diego, CA (US); Sergio G. Duron, San Diego, CA (US); Carl Lebel, Malibu, CA (US); Fabrice Piu, San Diego, CA (US); Qiang Ye, San Diego, CA (US); Luis A. Dellamary, San Marcos, CA (US); Andrew M. Trammel, Olathe, KS (US); Michael Christopher Scaife, Los Altos, CA (US); Jeffrey P. Harris, La Jolla, CA (US)

(73) Assignees: Otonomy, Inc, San Diego, CA (US); The Regents of the University of California, Oakland, CA (US)

( * ) Notice: Subject to any disclaimer, the term of this patent is extended or adjusted under 35 U.S.C. 154(b) by 652 days.

(21) Appl. No.: 12/504,553

(22) Filed: Jul. 16, 2009

(65) Prior Publication Data

US 2010/0015263 A1    Jan. 21, 2010

Related U.S. Application Data

(60) Provisional application No. 61/082,450, filed on Jul. 21, 2008, provisional application No. 61/083,830, filed on Jul. 25, 2008, provisional application No. 61/086,094, filed on Aug. 4, 2008, provisional application No. 61/094,384, filed on Sep. 4, 2008, provisional application No. 61/101,112, filed on Sep. 29, 2008, provisional application No. 61/140,033, filed on Dec. 22, 2008, provisional application No. 61/160,233, filed on Mar. 13, 2009, provisional application No. 61/164,812, filed on Mar. 30, 2009, provisional application No. 61/174,421, filed on Apr. 30, 2009.

(30) Foreign Application Priority Data

Apr. 24, 2009 (GB) ...................................... 0907070

(51) Int. Cl.
*A61K 9/14* (2006.01)
*A61K 31/47* (2006.01)
*A61K 31/517* (2006.01)

(52) U.S. Cl.
USPC ........ 424/437; 424/489; 514/266.1; 514/312; 514/646

(58) Field of Classification Search
None
See application file for complete search history.

(56) References Cited

U.S. PATENT DOCUMENTS

| 4,478,822 A | 10/1984 | Haslam et al. |
| 5,292,516 A | 3/1994 | Viegas et al. |

(Continued)

FOREIGN PATENT DOCUMENTS

| CA | 2268331 | 5/1998 |
| CN | 101134780 | 3/2008 |

(Continued)

OTHER PUBLICATIONS

Doleviczenyi et al., "Cochlear dopamine release is modulated by group II metobotropic glutamate receptors via GABAergic neurotransmission," Neuroscience Ltrs 385:93-98 (2005).

(Continued)

*Primary Examiner* — Jeffrey E Russel
(74) *Attorney, Agent, or Firm* — Wilson, Sonsini, Goodrich & Rosati

(57) ABSTRACT

Disclosed herein are methods for the treatment of otic diseases or conditions with intratympanic compositions and formulations of multiparticulate auris sensory cell modulating agent administered locally to an individual afflicted with an otic disease or condition, through direct application of these compositions and formulations onto or via perfusion into the targeted auris structure(s).

13 Claims, 5 Drawing Sheets

U.S. PATENT DOCUMENTS

| | | | |
|---|---|---|---|
| 5,503,848 | A | 4/1996 | Perbellini et al. |
| 6,316,011 | B1 | 11/2001 | Ron et al. |
| 6,392,036 | B1 | 5/2002 | Karlsson et al. |
| 6,740,664 | B2 | 5/2004 | Cagle et al. |
| 7,001,615 | B1 * | 2/2006 | Singh et al. ............... 424/488 |
| 7,524,834 | B2 | 4/2009 | Karlsson et al. |
| 7,589,110 | B2 | 9/2009 | Puel et al. |
| 8,030,297 | B2 * | 10/2011 | Lichter et al. ............ 514/178 |
| 8,197,461 | B1 | 6/2012 | Arenberg et al. |
| 8,399,018 | B2 * | 3/2013 | Lichter et al. ............ 424/484 |
| 2003/0092776 | A1 | 5/2003 | Ron et al. |
| 2003/0229333 | A1 | 12/2003 | Ashton |
| 2004/0082509 | A1 | 4/2004 | Bonny |
| 2004/0101560 | A1 | 5/2004 | Sawchuk et al. |
| 2004/0192763 | A1 | 9/2004 | Chenard et al. |
| 2005/0147585 | A1 | 7/2005 | Schwarz |
| 2005/0214338 | A1 | 9/2005 | Guitton et al. |
| 2006/0013858 | A1 | 1/2006 | Trune |
| 2006/0046970 | A1 | 3/2006 | Bowman et al. |
| 2006/0063802 | A1 | 3/2006 | Guitton et al. |
| 2006/0074083 | A1 | 4/2006 | Kalvinsh et al. |
| 2006/0205789 | A1 | 9/2006 | Lobl et al. |
| 2006/0216353 | A1 | 9/2006 | Liversidge et al. |
| 2006/0264897 | A1 | 11/2006 | Lobl et al. |
| 2006/0269602 | A1 | 11/2006 | Dasch et al. |
| 2007/0021352 | A1 | 1/2007 | Anderson et al. |
| 2007/0178051 | A1 | 8/2007 | Pruitt et al. |
| 2007/0299113 | A1 | 12/2007 | Kalvinsh et al. |
| 2008/0103118 | A1 * | 5/2008 | Clement et al. ............ 514/169 |
| 2011/0166060 | A1 * | 7/2011 | Simons et al. ............. 514/2.8 |

FOREIGN PATENT DOCUMENTS

| | | |
|---|---|---|
| EP | 1107791 B1 | 6/2001 |
| GB | 2459910 | 11/2009 |
| WO | WO 97/38698 | 10/1997 |
| WO | WO 99/24051 | 5/1999 |
| WO | WO-02-056890 A1 | 7/2002 |
| WO | WO 03/034979 | 5/2003 |
| WO | WO 03/017990 | 6/2003 |
| WO | WO 03/071986 | 9/2003 |
| WO | WO 2006/099325 | 9/2006 |
| WO | WO 2007/031098 | 3/2007 |
| WO | WO 2007/031280 | 3/2007 |
| WO | WO 2007/037874 | 4/2007 |
| WO | WO 2007/037886 | 4/2007 |
| WO | WO 2007/038949 | 4/2007 |
| WO | WO-2007-045876 A1 | 4/2007 |
| WO | WO 2007/119098 | 10/2007 |
| WO | WO 2008/076556 | 6/2008 |
| WO | WO 2009/132050 | 10/2009 |
| WO | WO-2010-048095 A2 | 4/2010 |
| WO | WO-2010-048095 A3 | 4/2010 |

OTHER PUBLICATIONS

Dourmishev et al., "Waardenburg syndrome," Intl J Dermatol 39:656-663 (1999).
Hall et al., "Anti-Pneumocystis Activities of Aromatic Diamidoxine Prodrugs," Antimicrobial Agents & Chemotherapy, 1998, American Society for Microbiology 42(4):666-674 (1998).
McCarthy et al., "Alport syndrome: a review," Clinical Eye and Vision Care 12:139-150 (2000).
Nance et al., "The Genetics of Deafness," Mental Retardation and Developmental Disabilities, 2003, Wiley-Liss, vol. 9, pp. 109-119.
Peng et al., "Group I metabotropic glutamate receptors in spiral Ganglion neutrons contribute to excitatory neurotransmissions in the cochlea," Neuroscience 123:221-230 (2004).
Salt et al., "Local Inner Ear Drug Delivery and Pharmacokinetics," Drug Discovery Today 10(19):1299-1306 (2005).
Suzuki et al., "Pharmacological Characterization of a New, orally Active and Potent Allosteric Metabotropic Glutamate receptor 1 Antagonist, 4-[1-2(-Fluoropyrisin-3-yl)-5-methyl-1H-1,2,3-triazol-4-yl]-N-isopropyl-N-methyl-3,6-dihydropyricine-1(2H)-carboxamide (FTIDC)," J Pharmacol Exp Therapeutics 321(3):1144-1153 (2007).
PCT/US09/061190 Search Report mailed May 14, 2010.
U.S. Appl. No. 12/466,310 Office Action mailed Jan. 12, 2011.
PCT/US2009/067552 international search report mailed Aug. 18, 2010.
Ahn et al., "Lipoic acid rescues DBA mice from early-onset age-related hearing impairment," Neuroreport 19(13):1265-9, 2008.
Arnold et al., "Novel slow- and fast-type drug release round-window microimplants for local drug application to the cochlea: an experimental study in guinea pigs," Audiol Neurootol 10(1):53-63, 2005.
Auris Medical, press release reporting initiating of phase I/II clinical trial with AM-101, Feb. 22, 2007.
Auris Medical, press release reporting results of phase I/II clinical trial with AM-111, Jun. 21, 2006.
Battaglia et al., "Combination therapy (intratympanic dexamethasone + high-dose prednisone taper) for the treatment of idiopathic sudden sensorineural hearing loss," Otol Neurotol 29(4):453-60, 2008.
Campbell et al., "Oral-D-methionine (MRX-1024) significantly protects against cisplatin-induced hearing loss: a phase II study in humans," Abst $32^{nd}$ Ann MidWinter Res Meeting, ARO Abstracts 32:7, Feb. 14-19, 2009.
Chen and Nathans, "Estrogen-related receptor beta/NR3B2 controls epithelial cell fate and endolymph production by the stria vascularis," Dev Cell 13(3):325-37, 2007.
Chen et al., "Design and preparation of thermosensitive in situ gel of dexamethasone sodium phosphate," J Guangdong Coll Pharm 23(5):518-21, 2007 (English abstract).
Chen et al., "Evaluation of thermosensitive in situ gel using dynamic rheological experiment," Chin Pharm J 43(6):444-447, 2008 (English abstract).
Chen et al., "In vivo distribution and pharmacokinetics of dexamethasone sodium phosphate thermosensitive in situ gel following intratympanic injection," Sichuan Da Xue Xue Bao Yi Xue Ban 37(3):456-9, 2006 (English translation).
Chen et al., "Preparation and characterization of dexamethasone acetate-loaded solid lipid nanoparticles," Chinese J Pharm 39(4):261-264, 2008 (English abstract).
Chen et al., "Study on dexamethasone thermosensitive in situ gel for treating deafness," Chin Pharm J 41(9):685-688, 2006 (English abstract).
CIPRODEX, product label, 2009.
Derin et al., "The effects of L-carnitine on presbyacusis in the rat model," Clin Otolaryngol Allied Sci 29(3):238-41, 2004.
Endo et al., "Novel strategy for treatment of inner ears using a biodegradable gel," Laryngoscope 115(11):2016-20, 2005.
Feng et al., "Effect of poloxamer 407 on the middle ear and inner ear after regional perfusion in guinea pigs," Zhonghua Er Bi Yan Hou Tou Jing Wai Ke Za Zhi 42(6):443-6, 2007 (English translation).
Feng et al., "In vitro and in vivo biodegradation of sustained-release vehicle poloxamer 407 in situ gel," Lin Chung Er Bi Yan Hou Tou Jing Wai Ke Za Zhi 22(1):28-31, 2008 (English translation).
Fernandez et al., "Self-curing controlled release systems for steroids. Application of prednisolone-based polymeric systems to ear diseases," Biomaterials 26(16):3311-8, 2005.
Friedman et al., "GRM7 variants confer susceptibility to age-related hearing impairment," Hum Mol Genet 18(4):785-96, 2009.
Garduno-Anaya et al., "Dexamethasone inner ear perfusion by intratympanic injection in unilateral Ménière's disease: a two-year prospective, placebo-controlled, double-blind, randomized trial," Otolaryngol Head Neck Surg 133(2):285-94, 2005.
Gubbels et al., "Functional auditory hair cells produced in the mammalian cochlea by in utero gene transfer," Nature 455(7212):537-41, 2008.
Guyot et al., "Intratympanic application of an antiviral agent for the treatment of Ménière's disease," ORL J Otorhinolaryngol Relat Spec 70(1):21-6; discussion 26-7, 2008.
Hargunani et al., "Intratympanic injection of dexamethasone: time course of inner ear distribution and conversion to its active form," Otol Neurotol 27(4):564-9, 2006.
Harris et al., "Prevention of noise-induced hearing loss with Src-PTK inhibitors," Hear Res 208(1-2):14-25, 2005.
Harris et al., "Treatment of corticosteroid-responsive autoimmune inner ear disease with methotrexate: a randomized controlled trial," JAMA 290(14):1875-83, 2003.

Hill et al., "Cisplatin-induced ototoxicity: effect of intratympanic dexamethasone injections," Otol Neurotol 29:1005-11, 2008.

Hoffer et al., "Transtympanic management of tinnitus," Otolaryngol Clin North Am 36(2):353-8, 2003.

Hoshino et al., "The non-steroidal anti-inflammatory drugs protect mouse cochlea against acoustic injury," Tohoku J Exp Med 216(1):53-9, 2008.

Inaoka et al., "Local application of hepatocyte growth factor using gelatin hydrogels attenuates noise-induced hearing loss in guinea pigs," Acta Otolaryngol 129(4):453-7, 2009.

Jia et al., "Intratympanic dexamethasone for refractory sudden deafness," Lin Chung Er Bi Yan Hou Tou Jing Wai Ke Za Zhi 22(7):309-11, 2008 (English translation).

Kazama et al., "Lithium effectively complements vasopressin V2 receptor antagonist in the treatment of hyponatraemia of SIADH rats," Nephrol Dial Transplant 22(1):68-76, 2007.

Keithley et al., "GDNF protects the cochlea against noise damage," Neuroreport 9(10):2183-7, 1998.

Kim et al., "Effects of tumor necrosis factor alpha antagonist, platelet activating factor antagonist, and nitric oxide synthase inhibitor on experimental otitis media with effusion," Ann Otol Rhinol Laryngol 115(8):617-23, 2006.

Kitahara et al., "Up-regulation of cochlear aquaporin-3 mRNA expression after intra-endolymphatic sac application of dexamethasone," Neurol Res. 25(8):865-70, 2003.

Lamm and Arnold, "The effect of prednisolone and non-steroidal anti-inflammatory agents on the normal and noise-damaged guinea pig inner ear," Hear Res 115(1-2):149-61, 1998.

Lavreysen and Dautzenberg, "Therapeutic potential of group III metabotropic glutamate receptors," Curr Med Chem 15(7):671-84, 2008.

Lee et al., "Novel therapy for hearing loss: delivery of insulin-like growth factor 1 to the cochlea using gelatin hydrogel," Otol Neurotol 28(7):976-81, 2007.

Lee et al., "Regional delivery of vancomycin using pluronic F-127 to inhibit methicillin resistant Staphylococcus aureus (MRSA) growth in chronic otitis media in vitro and in vivo," J Control Release 96(1):1-7, 2004.

Liu et al., "Permeability of different Dexamethasone drugs through round window membrane," Zhonghua Er Bi Yan Hou Tou Jing Wai Ke Za Zhi 41(3):211-5, 2006 (English abstract).

McGuinness and Shepherd, "Exogenous BDNF rescues rat spiral ganglion neurons in vivo," Otol Neurotol 26(5):1064-72, 2005.

Meltser et al., "Estrogen receptor beta protects against acoustic trauma in mice," J Clin Invest 118(4):1563-70, 2008.

Miceli et al., "Molecular pharmacology and therapeutic potential of neuronal Kv7-modulating drugs," Curr Opin Pharmacol 8(1):65-74, 2008.

Mitsukawa et al., "A selective metabotropic glutamate receptor 7 agonist: activation of receptor signaling via an allosteric site modulates stress parameters in vivo," Proc Natl Acad Sci U S A 102(51):18712-7, 2005.

Nakagawa and Ito, "Local drug delivery to inner ear for treatment of hearing loss," Curr Drug Ther 3:143-147, 2008.

Nishimaki et al., "Reduction of metabotropic glutamate receptor-mediated heterosynaptic inhibition of developing MNTB-LSO inhibitory synapses," Eur J Neurosci 26(2):323-30, 2007.

Nouvian et al., "Degeneration of sensory outer hair cells following pharmacological blockade of cochlear KCNQ channels in the adult guinea pig," Eur J Neurosci 17(12):2553-62, 2003.

Park et al., "Effect of inhibitor of tumor necrosis factor-alpha and oxatomide on immune mediated otitis media," Laryngoscope 116(9):1642-6, 2006.

Parnes et al., "Corticosteroid pharmacokinetics in the inner ear fluids: an animal study followed by clinical application," Laryngoscope 109(7 Pt 2 Supplement No. 91):1-17, 1999.

Paulson et al., "A novel controlled local drug delivery system for inner ear disease," Laryngoscope 118(4):706-11, 2008.

Peng et al., "Clinical investigation of different routes of administration of dexamethasone on sudden deafness," Lin Chung Er Bi Yan Hou Tou Jing Wai Ke Za Zhi 22(10):442-5, 2008 (English translation).

Plontke et al., "Rapid clearance of methylprednisolone after intratympanic application in humans. Comment on: Bird PA, Begg EJ, Zhang M, et al. Intratympanic versus intravenous delivery of methylprednisolone to cochlear perilymph. Otol Neurotol 2007; 28:1124-30," Otol Neurotol 29(5):732-3, 2008.

Pondugula et al., "Glucocorticoid regulation of genes in the amiloride-sensitive sodium transport pathway by semicircular canal duct epithelium of neonatal rat," Physiol Genomics 24(2):114-23, 2006.

Pondugula et al., "Glucocorticoids stimulate cation absorption by semicircular canal duct epithelium via epithelial sodium channel," Am J Physiol Renal Physiol 286(6):F1127-35, 2004.

Psillas et al., "Potential efficacy of early treatment of acute acoustic trauma with steroids and piracetam after gunshot noise," Eur Arch Otorhinolaryngol 265(12):1465-9, 2008.

Puel, "Chemical synaptic transmission in the cochlea," Prog Neurobiol 47(6):449-76, 1995.

Satoh et al., "Tumor necrosis factor-alpha, an initiator, and etanercept, an inhibitor of cochlear inflammation," Laryngoscope 112(9):1627-34, 2002.

Schoepp et al., "Pharmacological agents acting at subtypes of metabotropic glutamate receptors," Neuropharmacology 38(10):1431-76, 1999.

Seidman et al., "Anti-intercellular adhesion molecule-1 antibody's effect on noise damage," Laryngoscope 119(4):707-12, 2009.

She et al., "A short term study on the efficacies of intratympanic prednisolone and dexamethasone injection for subjective tinnitus," Lin Chung Er Bi Yan Hou Tou Jing Wai Ke Za Zhi 22(19):871-3, 2008 (English translation).

Shepherd et al., "Neurotrophins and electrical stimulation for protection and repair of spiral ganglion neurons following sensorineural hearing loss," Hear Res 242(1-2):100-9, 2008.

Shinohara et al., "Neurotrophic factor intervention restores auditory function in deafened animals," Proc Natl Acad Sci U S A 99(3):1657-60, 2002.

Sun et al., "In vitro permeability of round window membrane to transforming dexamethasone with delivery vehicles—a dosage estimation," Chin Med J (Engl) 120(24):2284-9, 2007.

SYNPHORA AB, website printout for JB004/A, 2009.

Tabuchi et al., "Hearing impairment in TRPV4 knockout mice," Neurosci Lett 382(3):304-8, 2005.

Taguchi et al., "Expressions of aquaporin-2, vasopressin type 2 receptor, transient receptor potential channel vanilloid (TRPV)1, and TRPV4 in the human endolymphatic sac," Laryngoscope 117(4):695-8, 2007.

Tahera et al., "NF-kB mediated glucocorticoid response in the inner ear after acoustic trauma," J Neurosci Res 1;83(6):1066-76, 2006.

Takeda and Taguchi, "Aquaporins as potential drug targets for Meniere's disease and its related diseases," Handb Exp Pharmacol 190:171-84, 2009.

Takeda et al., "Decompression effects of erythritol on endolymphatic hydrops," Auris Nasus Larynx 36(2):146-51, 2009.

Takeda et al., "The effects of V2 antagonist (OPC-31260) on endolymphatic hydrops," Hear Res 182(1-2):9-18, 2003.

Takemura et al., "Direct inner ear infusion of dexamethasone attenuates noise-induced trauma in guinea pig," Hear Res 196(1-2):58-68, 2004.

Takumida and Anniko, "Nitric oxide in the inner ear,"Cur Opin Neurol 15(1):11-5, 2002.

Tang et al., "COUP-TFI controls Notch regulation of hair cell and support cell differentiation," Development 133(18):3683-93, 2006.

The Royal National Institute for Deaf People (RNID), advertisement in Nature 8(5):339-431, 2009.

Thorne et al., "Potential role of purinergic signalling in cochlear pathology," Audiol Neurootol 7(3):180-4, 2002.

Van Wijk et al., "Local perfusion of the tumor necrosis factor alpha blocker infliximab to the inner ear improves autoimmune neurosensory hearing loss," Audiol Neurootol 11(6):357-65, 2006.

Wang et al., "A novel dual inhibitor of calpains and lipid peroxidation (BN82270) rescues the cochlea from sound trauma," Neuropharmacology 52(6):1426-37, 2007.

Wang et al., "Over-expression of X-linked inhibitor of apoptosis protein slows presbycusis in C57BL/6J mice," Neurobiol Aging Aug. 26, 2008 [Epub ahead of print].

Watanabe et al., "Inhibition of inducible nitric oxide synthase lowers the cochlear damage by lipopolysaccharide in guinea pigs," Free Radic Res 32(4):363-70, 2000.

Watanabe et al., "Nitric oxide synthase inhibitor reduces the apoptotic change in the cisplatin-treated cochlea of guinea pigs," Anticancer Drugs 11(9):731-5, 2000.

Watanabe et al., "Nitric oxide synthase inhibitor suppresses the ototoxic side effect of cisplatin in guinea pigs," Anticancer Drugs 11(5):401-6, 2000.

Yamamoto et al., "Inhibition of Notch/RBP-J signaling induces hair cell formation in neonate mouse cochleas," J Mol Med 84(1):37-45, 2006.

Yang et al., "Intratympanic immunosuppressives for prevention of immune-mediated sensorineural hearing loss," Am J Otol 21(4):499-504, 2000.

Yildirim et al., "Effect of intratympanic dexamethasone on noise-induced temporary threshold shift," Laryngoscope 115(7):1219-22, 2005.

Zheng et al., "Vanilloid receptors in hearing: altered cochlear sensitivity by vanilloids and expression of TRPV1 in the organ of corti," J Neurophysiol 90(1):444-55, 2003.

Zhou et al., "Intratympanic administration of methylprednisolone reduces impact of experimental intensive impulse noise trauma on hearing," Acta Oto-Laryngologica 129:602-607, 2009.

Combined search and examination report in UK Patent Application No. GB0823378.5 dated Feb. 27, 2009.

Combined search and examination report in UK Patent Application No. GB0912650.9 dated Oct. 23, 2009.

Combined search and examination report in UK Patent Application No. GB0907065.7 dated Nov. 16, 2009.

Examination report in UK Patent Application No. GB0823378.5 dated Oct. 23, 2009.

PCT/US2008/061330 International Search Report mailed Jul. 31, 2008.

Lichter et al., U.S. Appl. No. 12/466,310, filed May 14, 2009.
Lichter et al., U.S. Appl. No. 12/472,034, filed May 26, 2009.
Lichter et al., U.S. Appl. No. 12/493,611, filed Jun. 29, 2009.
Lichter et al., U.S. Appl. No. 12/427,663, filed Apr. 21, 2009.
Lichter et al., U.S. Appl. No. 12/486,697, filed Jun. 17, 2009.
Lichter et al., U.S. Appl. No. 12/500,486, filed Jul. 9, 2009.
Lichter et al., U.S. Appl. No. 12/494,156, filed Jun. 29, 2009.
Lichter et al., U.S. Appl. No. 12/506,127, filed Jul. 20, 2009.
Lichter et al., U.S. Appl. No. 12/506,091, filed Jul. 20, 2009.
Lichter et al., U.S. Appl. No. 12/506,616, filed Jul. 21, 2009.
Lichter et al., U.S. Appl. No. 12/506,664, filed Jul. 21, 2009.
Lichter et al., U.S. Appl. No. 12/506,573, filed Jul. 21, 2009.
Friedman et al., U.S. Appl. No. 12/597,054, filed Oct. 22, 2009.

Karolewicz and Pluta, "Thermosensitive polymers in drug form technology II. Possibilities of use of thermosensitive polymers as active substance carriers," Polimery W Medycynie 38(1):15-26, 2008 (English language abstract).

Combined search and examination report in UK Patent Application No. GB0907070.7 dated Nov. 23, 2009.

PCT/US2009/051078 International Search Report mailed Feb. 24, 2010.

U.S. Appl. No. 12/506,091 Office Action dated Feb. 22, 2012.

Feng et al., Zhonghua er Bi Yan Hou Tou Jing Wai Ke Zu Zhi, Jun. 2004;42(6):443-6 (English Abstract).

Feng et al., Zhonghua Yi Xue Za Zhi, Aug. 28, 2007;87(32):2289-91 (English Translation).

* cited by examiner

SEQUENCE LISTING

<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atgaattaat                                                          10

CONTROLLED RELEASE AURIS SENSORY CELL MODULATOR COMPOSITIONS AND METHODS FOR THE TREATMENT OF OTIC DISORDERS

CROSS-REFERENCE

This patent application claims the benefit of U.S. Provisional Application Ser. No. 61/082,450 filed Jul. 21, 2008; U.S. Provisional Application Ser. No. 61/083,830 filed Jul. 25, 2008; U.S. Provisional Application Ser. No. 61/086,094, filed Aug. 4, 2008; U.S. Provisional Application Ser. No. 61/094,384 filed Sep. 4, 2008; U.S. Provisional Application Ser. No. 61/101,112 filed Sep. 29, 2008; U.S. Provisional Application Ser. No. 61/140,033 filed Dec. 22, 2008; U.S. Provisional Application Ser. No. 61/160,233, filed Mar. 13, 2009; U.S. Provisional Application Ser. No. 61/164,812, filed Mar. 30, 2009; U.S. Provisional Application Ser. No. 61/174,421 filed Apr. 30, 2009; and UK Patent Application No. 0907070.7, filed Apr. 24, 2009; all of which are incorporated by reference herein in their entirety.

SEQUENCE LISTING

The instant application contains a Sequence Listing which has been submitted via EFS-Web and is hereby incorporated by reference in its entirety. Said ASCII copy, created on Jul. 26, 2010, is named 37173-707-201-Sequence.txt and is 1,156 bytes in size.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein are compositions, formulations, manufacturing methods, therapeutic methods, uses, kits, and delivery devices for the controlled release or delivery of at least one auris sensory cell modulator to at least one structure or region of the ear. In some embodiments, an auris sensory cell modulator is an auris sensory cell damage agent. In some embodiments, an auris sensory cell modulator is an auris sensory cell death agent. In some embodiments, an auris sensory cell modulator is an auris sensory cell protection agent (e.g., promotes survival of auris sensory cells). In some embodiments, an auris sensory cell modulator is an auris sensory cell growth/regeneration agent. Disclosed herein are controlled release compositions for treating or ameliorating hearing loss or reduction resulting from destroyed, stunted, malfunctioning, damaged, fragile or missing hairs in the inner ear. In one embodiment, the controlled release composition comprises a therapeutically-effective amount of at least one modulator of neuron and/or hair cells of the auris (also known as "auris sensory cell modulating agent"), a controlled release auris-acceptable excipient, and an auris-acceptable vehicle.

In some embodiments, the target portion of the ear is the middle ear or auris media. In other embodiments, the target portion of the ear is the inner ear, or auris interna. In other embodiments, the target portion of the ear is the middle ear, or auris media. In still other embodiments, the target portion of the ear is both the auris media and the auris interna. In some embodiments, the controlled release formulations further comprise a rapid or immediate release component for delivering an auris sensory cell modulating agent to the auris media and/or the auris interna. All formulations comprise excipients that are auris-media and/or auris-interna acceptable.

Described herein are methods for inducing selective auris sensory cell damage and/or death within the auris media or auris interna comprising administration of the auris sensory cell modulating agent controlled release formulations described herein. Also described herein are methods for inducing auris sensory cell growth and/or reversal of damage to auris sensory cells (e.g. stunted or malfunctioning auris sensory cells) and/or protection against further damage to auris sensory cells (e.g. stunted or malfunctioning auris sensory cells) comprising administration of the auis sensory cell modulating agent compositions described herein.

Also disclosed herein are methods for the treatment of otic disorders comprising administration of auris sensory cell modulating agent controlled release formulations. In some embodiments, the auris sensory cell modulating agent is a toxicant (e.g., gentamicin) and induces cell death. In some embodiments, the auris sensory cell modulating agent is an otoprotectant, e.g., amifostine, an antioxidant, or the like. In some embodiments, the auris sensory cell modulating agent induces growth of new auris sensory cells, e.g., an adenovirus expressing Atoh1. In some embodiments, the auris sensory cell modulating is an agent that reduces or inhibits auris sensory cell death, e.g., a glutamate receptor modulator.

In some embodiments, a glutamate receptor modulator is a glutamate receptor antagonist. In some embodiments, a glutamate receptor antagonist is an NMDA receptor antagonist. In some embodiments, the agent that modulates the NMDA receptor is an NMDA receptor antagonist. In some embodiments, an auris sensory cell modulating agent is a trophic agent (e.g., an agent that promotes growth of healthy cells and/or tissue). In some embodiments, a trophic agent is a growth factor. In some embodiments, a growth factor is brain-derived neurotrophic factor (BDNF), ciliary neurotrophic factor (CNTF), glial cell-line derived neurotrophic factor (GDNF), neurotrophin-3, neurotrophin-4, fibroblast growth factor (FGF), insulin-like growth factor (IGF) or the like and/or combinations thereof. In some embodiments, the auris sensory cell modulating agent is an agent that has a protective effect, e.g., immune system cells that reduce inflammation and/or infections. In some embodiments, the immune system cells are macrophages, microglia, and/or microglia-like cells. In some embodiments, the auris sensory cell modulating agent is a Na+ channel blocker and reduces or inhibits auris sensory cell damage and/or death. In some embodiments, the auris sensory cell modulating agent is an otoprotectant, e.g., a corticosteroid that reduces, delays or reverses damage to auris sensory cells. In some embodiments, the auris sensory cell modulating agent is an ototoxic agent or a toxicant that causes auris sensory cell death. In some embodiments, the auris sensory cell modulating agent is a modulator of pRB. In some embodiments, the auris sensory cell modulating agent is a modulator of a TH receptor. In some embodiments, the auris sensory cell modulating agent is an adenovirus expressing a BRN3. In some embodiments, the auris sensory cell modulating agent is an agonist of a BRN3. In some embodiments, the auris sensory cell modulating agent is an antagonist of a BRN3. In some embodiments, the auris sensory cell modulating agent is a stem cell and/or differentiated auris sensory cell that promotes growth and/or regeneration of auris sensory cells.

In some embodiments, the composition further comprises an auris sensory cell modulating agent as an immediate release agent wherein the immediate release auris sensory cell modulating agent is the same agent as the controlled-release agent, a different auris sensory cell modulating agent, an additional therapeutic agent, or a combination thereof.

In some embodiments, the composition further comprises an additional therapeutic agent. In some embodiments, the additional therapeutic agent is an anesthetic, a local acting anesthetic, an analgesic, an antibiotic, an antiemetic, an antifungal, an anti-microbial agent, an antiseptic, an antiviral, a chemotherapeutic agent, a diuretic, a keratolytic agent, an otoprotectant (e.g., a steroid), an immunosuppressant comprising but not limited to such agents as calcineurin inhibitors (cyclosporine, tacrolimus, pimecrolimus), macrolides such as rapamycin, corticosteroids, or combinations thereof. In some embodiments, the additional therapeutic agent is an immediate release agent. In some embodiments, the additional therapeutic agent is a controlled release agent.

Disclosed herein are controlled release formulations for delivering an auris sensory cell modulating agent to the ear. In some embodiments, the composition is administered so that the composition is in contact with the crista fenestrae cochleae, the round window or the tympanic cavity.

The auris formulations and therapeutic methods described herein have numerous advantages that overcome the previously-unrecognized limitations of formulations and therapeutic methods described in prior art.

Sterility

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., auris sensory cell modulating agents) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobins (e.g. in response to a microbial infection) into the endolymph and/or the perilymph and the delicate ionic composition of inner ear fluids is upset by the influx of leukocytes and/or immunoglobins. In certain instances, a change in the ionic composition of inner ear fluids results in hearing loss, loss of balance and/or ossification of auditory structures. In certain instances, even trace amounts of pyrogens and/or microbes can trigger infections and related physiological changes in the isolated microenvironment of the inner ear.

Due to the susceptibility of the inner ear to infections, auris formulations require a level of sterility (e.g., low bioburden) that has not been recognized hitherto in prior art. Provided herein are auris formulations that are manufactured with low bioburden or sterilized with stringent sterility requirements and are suitable for administration to the middle and/or inner ear. In some embodiments, the auris compatible compositions described herein are substantially free of pyrogens and/or microbes.

Compatibility with Inner Ear Environment

Described herein are otic formulations with an ionic balance that is compatible with the perilymph and/or the endolymph and does not cause any change in cochlear potential. In specific embodiments, osmolarity/osmolality of the present formulations is adjusted, for example, by the use of appropriate salt concentrations (e.g., concentration of sodium salts) or the use of tonicity agents which renders the formulations endolymph-compatible and/or perilymph-compatible (i.e. isotonic with the endolymph and/or perilymph). In some instances, the endolymph-compatible and/or perilymph-compatible formulations described herein cause minimal disturbance to the environment of the inner ear and cause minimum discomfort (e.g., vertigo) to a mammal (e.g., a human) upon administration. Further, the formulations comprise polymers that are biodegradable and/or dispersable, and/or otherwise non-toxic to the inner ear environment. In some embodiments, the formulations described herein are free of preservatives and cause minimal disturbance (e.g., change in pH or osmolarity, irritation) in auditory structures. In some embodiments, the formulations described herein comprise antioxidants that are non-irritating and/or non-toxic to otic structures.

Dosing Frequency

The current standard of care for auris formulations requires multiple administrations of drops or injections (e.g. intratympanic injections) over several days (e.g., up to two weeks), including schedules of receiving multiple injections per day. In some embodiments, auris formulations described herein are controlled release formulations, and are administered at reduced dosing frequency compared to the current standard of care. In certain instances, when an auris formulation is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the ear drum. The formulations described herein provide a constant, sustained, extended, delayed or pulsatile rate of release of an active agent into the inner ear environment and thus avoid any variability in drug exposure in treatment of otic disorders.

Therapeutic Index

Auris formulations described herein are administered into the ear canal, or in the vestibule of the ear. Access to, for example, the vestibular and cochlear apparatus will occur through the auris media including the round window membrane, the oval window/stapes footplate, the annular ligament and through the otic capsule/temporal bone. Otic administration of the formulations described herein avoids toxicity associated with systemic administration (e.g., hepatotoxicity, cardiotoxicity, gastrointestinal side effects, renal toxicity) of the active agents. In some instances, localized administration in the ear allows an active agent to reach a target organ (e.g., inner ear) in the absence of systemic accumulation of the active agent. In some instances, local administration to the ear provides a higher therapeutic index for an active agent that would otherwise have dose-limiting systemic toxicity.

Prevention of Drainage into Eustachian Tube

In some instances, a disadvantage of liquid formulations is their propensity to drip into the eustachian tube and cause rapid clearance of the formulation from the inner ear. Provided herein, in certain embodiments, are auris formulations comprising polymers that gel at body temperature and remain in contact with the target auditory surfaces (e.g., the round window) for extended periods of time. In some embodiments, the formulations further comprise mucoadhesives that allow the formulations to adhere to otic mucosal surfaces. In some instances, the auris formulations described herein avoid attenuation of therapeutic benefit due to drainage or leakage of active agents via the eustachian tube.

DESCRIPTION OF CERTAIN EMBODIMENTS

Described herein are controlled release compositions and devices for treating otic disorders comprising a therapeutically-effective amount of an auris sensory cell modulating agent, a controlled release auris-acceptable excipient and an auris-acceptable vehicle. In one aspect, the controlled release auris-acceptable excipient is chosen from an auris-acceptable polymer, an auris-acceptable viscosity enhancing agent, an auris-acceptable gel, an auris-acceptable paint, an auris-acceptable foam, an auris-acceptable microsphere or microparticle, an auris-acceptable hydrogel, an auris-acceptable in situ forming spongy material, an auris-acceptable actinic radiation curable gel, an auris-acceptable liposome, an auris-acceptable nanocapsule or nanosphere, an auris-acceptable thermoreversible gel or combinations thereof. In further embodiments, the auris-acceptable viscosity enhancing agent is a cellulose, a cellulose ether, alginate, polyvinylpyrrolidone, a gum, a cellulosic polymer or combinations thereof. In yet another embodiment, the auris-acceptable viscosity enhancing agent is present in an amount sufficient to provide a viscosity of between about 1000 to about 1,000,000 centipoise. In still another aspect, the auris-acceptable viscosity enhancing agent is present in an amount sufficient to provide a viscosity of between about 50,000 to about 1,000,000 centipoise. In some embodiments, the auris sensory cell modulating agent formulations or compositions are optimal for osmolality or osmolarity of the target auris structure to ensure homeostasis is maintained.

In some embodiments, the compositions are formulated for pH, and a practical osmolality or osmolarity to ensure that homeostasis of the target auris structure is maintained. A perilymph-suitable osmolarity/osmolality is a practical/deliverable osmolarity/osmolality that maintains the homeostasis of the target auris structure during administration of the pharmaceutical formulations described herein.

For example, the osmolarity of the perilymph is between about 270-300 mOsm/L, and the compositions described herein are optionally formulated to provide a practical osmolarity of about 150 to about 1000 mOsm/L. In certain embodiments, the formulations described herein provide a practical and/or deliverable osmolarity within about 150 to about 500 mOsm/L at the target site of action (e.g., the inner ear and/or the perilymph and/or the endolymph). In certain embodiments, the formulations described herein provide a practical osmolarity within about 200 to about 400 mOsm/L at the target site of action (e.g., the inner ear and/or the perilymph and/or the endolymph). In certain embodiments, the formulations described herein provide a practical osmolarity within about 250 to about 320 mOsm/L at the target site of action (e.g., the inner ear and/or the perilymph and/or the endolymph). In certain embodiments, the formulations described herein provide a perilymph-suitable osmolarity within about 150 to about 500 mOsm/L, about 200 to about 400 mOsm/L or about 250 to about 320 mOsm/L at the target site of action (e.g., the inner ear and/or the perilymph and/or the endolymph). In certain embodiments, the formulations described herein provide a perilymph-suitable osmolality within about 150 to about 500 mOsm/kg, about 200 to about 400 mOsm/kg or about 250 to about 320 mOsm/kg at the target site of action (e.g., the inner ear and/or the perilymph and/or the endolymph). Similarly, the pH of the perilymph is about 7.2-7.4, and the pH of the present formulations is formulated (e.g., with the use of buffers) to provide a perilymph-suitable pH of about 5.5 to about 9.0, about 6.0 to about 8.0 or about 7.0 to about 7.6. In certain embodiments, the pH of the formulations is within about 6.0 to about 7.6. In certain instances, the pH of the endolymph is about 7.2-7.9, and the pH of the present formulations is formulated (e.g., with the use of buffers) to be within about 5.5 to about 9.0, within about 6.5 to about 8.0 or within about 7.0 to about 7.6.

In some aspects, the controlled-release auris-acceptable excipient is biodegradable. In some aspects the controlled release auris-acceptable excipient is bioeliminated (e.g., degraded and/or eliminated through urine, feces or other routes of elimination). In another aspect, the controlled release composition further comprises an auris-acceptable mucoadhesive, an auris-acceptable penetration enhancer or an auris-acceptable bioadhesive.

In one aspect, the controlled release auris sensory cell modulating agent composition is delivered using a drug delivery device, which is a needle and syringe, a pump, a microinjection device or combinations thereof. In some embodiments, the auris sensory cell modulating agent of the controlled release composition has limited or no systemic release, is toxic when administered systemically, has poor pK characteristics or combinations thereof. In some aspects, the auris sensory cell modulating agent is a small molecule agent. In other aspects, the auris sensory cell modulating agent is an antibody.

Also disclosed herein is a method for treating an otic disorder comprising administering at least once every 3, 4, 5, 6, 7, 8, 9, 10, 11, 12, 13, 14, or 15 days, at least once a week, once every two weeks, once every three weeks, once every four weeks, once every five weeks, or once every six weeks; or once a month, once every two months, once every three months, once every four months, once every five months, once every six months, once every seven months, once every eight months, once every nine months, once every ten months, once every eleven months, or once every twelve months with the compositions and formulations disclosed herein. In particular embodiments, the controlled release formulations described herein provide a sustained dose of auris sensory cell modulating agent to the inner ear between subsequent doses of the controlled release formulation. That is, taking one example only, if new doses of the auris sensory cell modulating agent controlled release formulation are administered via intratympanic injection to the round window membrane every 10 days, then the controlled release formulation provides an effective dose of auris sensory cell modulating agent to the inner ear (e.g., across the round window membrane) during that 10-day period.

In one aspect, the composition is administered so that the composition is in contact with the crista fenestrae cochleae, the round window membrane or the tympanic cavity. In one aspect the composition is administered by intratympanic injection.

Provided herein, in some embodiments, are methods of selectively inducing auris sensory cell damage comprising administering to an individual in need thereof an intratympanic composition or device comprising a therapeutically effective amount of an ototoxic agent, the composition or device comprising substantially low degradation products of the ototoxic agent, the composition or device further comprising two or more characteristics selected from:
(i) between about 0.1% to about 10% by weight of the ototoxic agent, or pharmaceutically acceptable prodrug or salt thereof;
(ii) between about 14% to about 21% by weight of a polyoxyethylene-polyoxypropylene triblock copolymer of general formula E106 P70 E106;

(iii) sterile water, q.s., buffered to provide a pH between about 5.5 and about 8.0;
(iv) multiparticulate ototoxic agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the ototoxic agent; and
(ix) an apparent viscosity of about 100,000 cP to about 500,000 cP.

In some embodiments of the methods, the ototoxic agent is released from the composition or device for a period of at least 3 days. In some embodiments of the methods, the ototoxic agent is released from the composition or device for a period of at least 5 days. In some embodiments of the methods, the ototoxic agent is essentially in the form of micronized particles.

Also provided herein are methods of inducing auris sensory cell growth comprising administering to an individual in need thereof an intratympanic composition or device comprising a therapeutically effective amount of a trophic agent, the composition or device comprising substantially low degradation products of the trophic agent, the composition or device further comprising two or more characteristics selected from:
(i) between about 0.1% to about 10% by weight of the trophic agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate trophic agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the trophic agent; and
(ix) an apparent viscosity of about 100,000 cP to about 500,000 cP.

In some embodiments of the methods, the trophic agent is released from the composition or device for a period of at least 3 days. In some embodiments of the methods, the trophic agent is released from the composition or device for a period of at least 5 days. In some embodiments of the methods, the trophic agent is essentially in the form of micronized particles.

Also provided herein are methods of alleviating damage to auris sensory cells from an otic intervention comprising administering to an individual in need thereof an intratympanic composition or device comprising a therapeutically effective amount of an otoprotectant, the composition or device comprising substantially low degradation products of the otoprotectant, the composition or device further comprising two or more characteristics selected from:
(i) between about 0.1% to about 10% by weight of the otoprotectant, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate otoprotectant agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the otoprotectant agent; and
(ix) an apparent viscosity of about 100,000 cP to about 500,000 cP.

In some embodiments of the methods, the otoprotectant is administered before or during an otic intervention. In some embodiments of the methods, the otoprotectant is administered after an otic intervention. In some embodiments of the methods, the otoprotectant is essentially in the form of micronized particles.

In some embodiments of the methods described above, the composition or device comprises:
(i) between about 0.1% to about 10% by weight of the auris sensory cell modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate auris sensory cell modulating agent;
(iv) a gelation temperature between about 19° C. to about 42° C.; and
(v) an apparent viscosity of about 100,000 cP to about 500,000 cP.

In some embodiments of the methods described above, the composition or device comprises:
(i) between about 0.1% to about 10% by weight of the auris sensory cell modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate auris sensory cell modulating agent;
(iv) a gelation temperature between about 19° C. to about 42° C.; and
(v) a mean dissolution time of about 30 hours for the auris sensory cell modulating agent.

In some embodiments of the methods described above, the auris sensory cell modulating agent is released from the composition or device for a period of at least 3 days. In some embodiments of the methods described above, the auris sensory cell modulating agent is released from the composition or device for a period of at least 5 days. In some embodiments of the methods described above, the auris sensory cell modulating agent is released from the composition or device for a period of at least 10 days. In some embodiments of the method described above, the auris sensory cell modulating agent is essentially in the form of micronized particles.

In some embodiments of the methods described herein, the composition is administered across the round window. In some embodiments, the otic and/or vestibular disorder is ototoxicity, chemotherapy-induced hearing loss, sensorineural hearing loss, noise induced hearing loss, excitotoxicity, Meniere's Disease/Syndrome, endolymphatic hydrops, labyrinthitis, Ramsay Hunt's Syndrome, vestibular neuronitis, tinnitus or microvascular compression syndrome.

Provided herein are pharmaceutical compositions or devices comprising an amount of an ototoxic agent that is therapeutically effective for treating an otic disease or condition comprising substantially low degradation products of the ototoxic agent, the pharmaceutical composition or device further comprising two or more characteristics selected from:
(i) between about 0.1% to about 10% by weight of the ototoxic agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate ototoxic agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the ototoxic agent; and
(ix) an apparent viscosity of about 100,000 cP to about 500,000 cP.

In some embodiments, the pharmaceutical composition or device comprises:
(i) between about 0.1% to about 10% by weight of the ototoxic agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate ototoxic agent;
(iv) a gelation temperature between about 19° C. to about 42° C.;
(v) an apparent viscosity of about 100,000 cP to about 500,000 cP.

In some embodiments, the pharmaceutical composition or device comprises:
(i) between about 0.1% to about 10% by weight of the ototoxic agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate ototoxic agent;
(iv) a gelation temperature between about 19° C. to about 42° C.;
(v) an apparent viscosity of about 100,000 cP to about 500,000 cP.

In some embodiments, the pharmaceutical composition or device comprising an ototoxic agent provides a practical osmolarity between about 200 and 400 mOsm/L. In some embodiments, the pharmaceutical composition or device comprising an ototoxic agent provides a practical osmolarity between about 250 and 320 mOsm/L.

In some embodiments, an ototoxic agent is released from the composition or device for a period of at least 3 days. In some embodiments, an ototoxic agent is released from the composition or device for a period of at least 5 days. In some embodiments, the pharmaceutical composition or device comprising an ototoxic agent is an auris-acceptable thermoreversible gel. In some embodiments, the pharmaceutical composition or device comprises the ototoxic agent as essentially in the form of micronized particles.

Provided herein are pharmaceutical compositions or devices comprising an amount of a trophic agent that is therapeutically effective for treating an otic disease or condition comprising substantially low degradation products of the trophic agent, the pharmaceutical composition or device further comprising two or more characteristics selected from:
(i) between about 0.1% to about 10% by weight of the trophic agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate trophic agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the trophic agent; and
(ix) an apparent viscosity of about 100,000 cP to about 500,000 cP.

In some embodiments, the pharmaceutical composition or device comprises:
(i) between about 0.1% to about 10% by weight of the trophic agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate trophic agent;
(iv) a gelation temperature between about 19° C. to about 42° C.;
(viii) a mean dissolution time of about 30 hours for the trophic agent; and
(ix) an apparent viscosity of about 100,000 cP to about 500,000 cP.

In some embodiments, the pharmaceutical composition or device comprising a trophic agent provides a practical osmolarity between about 200 and 400 mOsm/L. In some embodiments, the pharmaceutical composition or device comprising a trophic agent provides a practical osmolarity between about 250 and 320 mOsm/L. In some embodiments, the trophic agent is released from the composition or device for a period of at least 3 days. In some embodiments, the trophic agent is released from the composition or device for a period of at least 5 days.

In some embodiments, the pharmaceutical composition or device comprising a trophic agent is an auris-acceptable thermoreversible gel. In some embodiments, the pharmaceutical composition or device comprises the trophic agent as essentially in the form of micronized particles.

In some embodiments any composition or device described above comprises:
(i) between about 0.1% to about 10% by weight of the auris sensory cell modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate auris sensory cell modulating agent;
(iv) a gelation temperature between about 19° C. to about 42° C.; and (v) a mean dissolution time of about 30 hours for the auris sensory cell modulating agent.

In some embodiments, any pharmaceutical composition or device described above comprises substantially low degradation products of the auris sensory cell modulating agent.

In some embodiments a pharmaceutical composition or device described above provides a practical osmolarity between about 150 and 500 mOsm/L. In some embodiments a pharmaceutical composition or device described above provides a practical osmolarity between about 200 and 400 mOsm/L. In some embodiments a pharmaceutical composition or device described above provides a practical osmolarity between about 250 and 320 mOsm/L.

In some embodiments, the auris sensory cell modulating agent is released from the pharmaceutical composition or device described above for a period of at least 3 days. In some embodiments, the auris sensory cell modulating agent is released from the pharmaceutical composition or device described above for a period of at least 5 days. In some embodiments, the auris sensory cell modulating agent is released from the pharmaceutical composition or device described above for a period of at least 10 days. In some embodiments, the auris sensory cell modulating agent is released from the pharmaceutical composition or device described above for a period of at least 14 days. In some embodiments, the auris sensory cell modulating agent is released from the pharmaceutical composition or device described above for a period of at least one month.

In some embodiments, a pharmaceutical composition or device described above comprises auris sensory cell modulating agent as a neutral compound, a free acid, a free base, a salt or a prodrug. In some embodiments, a pharmaceutical composition or device described above comprises auris sensory cell modulating agent as a neutral compound, a free acid, a free base, a salt or a prodrug, or a combination thereof. In some embodiments of the pharmaceutical compositions or devices described herein, the auris sensory cell modulating agent is administered in the form of an ester prodrug.

In some embodiments, a pharmaceutical composition or device described above is an auris-acceptable thermoreversible gel. In some embodiments of the pharmaceutical composition or device, the polyoxyethylene-polyoxypropylene triblock copolymer is bioeliminated.

In some embodiments the pharmaceutical composition or device further comprises a penetration enhancer. In some embodiments, the pharmaceutical composition or device further comprises a dye.

In some embodiments, the pharmaceutical composition or device further comprises the auris sensory cell modulating agent, or pharmaceutically acceptable salt thereof, prodrug or combination thereof as an immediate release agent.

In some embodiments of the pharmaceutical composition or device the auris sensory cell modulating agent comprises multiparticulates. In some embodiments of the pharmaceutical composition or device the auris sensory cell modulating agent is essentially in the form of micronized particles. In some embodiments of the pharmaceutical composition or device, the auris sensory cell modulating agent is in the form of micronized auris sensory cell modulating agent powder.

In some embodiments, a pharmaceutical composition or device described above comprises about 10% of a polyoxyethylene-polyoxypropylene triblock copolymer of general formula E106 P70 E106 by weight of the composition. In some embodiments, a pharmaceutical composition or device described above comprises about 15% of a polyoxyethylene-polyoxypropylene triblock copolymer of general formula E106 P70 E106 by weight of the composition. In some embodiments, a pharmaceutical composition or device described above comprises about 20% of a polyoxyethylene-polyoxypropylene triblock copolymer of general formula E106 P70 E106 by weight of the composition. In some embodiments, a pharmaceutical composition or device described above comprises about 25% of a polyoxyethylene-polyoxypropylene triblock copolymer of general formula E106 P70 E106 by weight of the composition.

In some embodiments, a pharmaceutical composition or device described above comprises about 0.01% of an auris sensory cell modulating agent, or pharmaceutically acceptable prodrug or salt thereof, by weight of the composition. In some embodiments, a pharmaceutical composition or device described above comprises about 0.05% of an auris sensory cell modulating agent, or pharmaceutically acceptable prodrug or salt thereof, by weight of the composition. In some embodiments, a pharmaceutical composition or device described above comprises about 0.1% of an auris sensory cell modulating agent, or pharmaceutically acceptable prodrug or salt thereof, by weight of the composition. In some embodiments, a pharmaceutical composition or device described above comprises about 1% of an auris sensory cell modulating agent, or pharmaceutically acceptable prodrug or salt thereof, by weight of the composition. In some embodiments, a pharmaceutical composition or device described above comprises about 2.5% of an auris sensory cell modulating agent, or pharmaceutically acceptable prodrug or salt thereof, by weight of the composition. In some embodiments, a pharmaceutical composition or device described above comprises about 5% of an auris sensory cell modulating agent, or pharmaceutically acceptable prodrug or salt thereof, by weight of the composition. In some embodiments, a pharmaceutical composition or device described above comprises about 10% of an auris sensory cell modulating agent, or pharmaceutically acceptable prodrug or salt thereof, by weight of the composition. In some embodiments, a pharmaceutical composition or device described above comprises about 20% of an auris sensory cell modulating agent, or pharmaceutically acceptable prodrug or salt thereof, by weight of the composition. In some embodiments, a pharmaceutical composition or device described above comprises about 30% of an auris sensory cell modulating agent, or pharmaceutically acceptable prodrug or salt thereof, by weight of the composition. In some embodiments, a pharmaceutical composition or device described above comprises about 40% of an auris sensory cell modulating agent, or pharmaceutically acceptable prodrug or salt thereof, by weight of the composition. In some embodiments, a pharmaceutical composition or device described above comprises up to about 50% of an auris sensory cell modulating agent, or pharmaceutically acceptable prodrug or salt thereof, by weight of the composition.

In some embodiments, a pharmaceutical composition or device described above has a pH between about 5.5 to about 8.0. In some embodiments, a pharmaceutical composition or device described above has a pH between about 6.0 to about 8.0. In some embodiments, a pharmaceutical composition or device described above has a pH between about 6.0 to about 7.6. In some embodiments, a pharmaceutical composition or device described above has a pH between about 7.0 to about 7.6.

In some embodiments, a pharmaceutical composition or device described above contains less than 100 colony forming units (cfu) of microbiological agents per gram of formulation. In some embodiments, a pharmaceutical composition or device described above contains less than 50 colony forming units (cfu) of microbiological agents per gram of formulation.

In some embodiments, a pharmaceutical composition or device described above contains less than 10 colony forming units (cfu) of microbiological agents per gram of formulation.

In some embodiments, a pharmaceutical composition or device described above contains less than 5 endotoxin units (EU) per kg of body weight of a subject. In some embodiments, a pharmaceutical composition or device described above contains less than 4 endotoxin units (EU) per kg of body weight of a subject.

In some embodiments a pharmaceutical composition or device described above provides a gelation temperature between about between about 19° C. to about 42° C. In some embodiments a pharmaceutical composition or device described above provides a gelation temperature between about between about 19° C. to about 37° C. In some embodiments a pharmaceutical composition or device described above provides a gelation temperature between about between about 19° C. to about 30° C.

In some embodiments, the pharmaceutical composition or device is an auris-acceptable thermoreversible gel. In some embodiments, the polyoxyethylene-polyoxypropylene triblock copolymer is biodegradable and/or bioeliminated (e.g., the copolymer is eliminated from the body by a biodegradation process, e.g., elimination in the urine, the feces or the like). In some embodiments, a pharmaceutical composition or device described herein further comprises a mucoadhesive. In some embodiments, a pharmaceutical composition or device described herein further comprises a penetration enhancer. In some embodiments, a pharmaceutical composition or device described herein further comprises a thickening agent. In some embodiments, a pharmaceutical composition or device described herein further comprises a dye.

In some embodiments, a pharmaceutical composition or device described herein further comprises a drug delivery device selected from a needle and syringe, a pump, a microinjection device, a wick, an in situ forming spongy material or combinations thereof.

In some embodiments, a pharmaceutical composition or device described herein is a pharmaceutical composition or device wherein the auris sensory cell modulating agent, or pharmaceutically acceptable salt thereof, has limited or no systemic release, systemic toxicity, poor PK characteristics, or combinations thereof. In some embodiments pharmaceutical compositions or devices described herein comprise one or more auris sensory cell modulating agent, or pharmaceutically acceptable salt thereof, prodrug or combination thereof as an immediate release agent.

In some embodiments, pharmaceutical compositions or devices described herein are pharmaceutical compositions or devices wherein the pH of the pharmaceutical composition or device is a perilymph-suitable pH between about 6.0 to about 7.6.

In some embodiments of the pharmaceutical compositions or devices described herein, the ratio of a polyoxyethylene-polyoxypropylene triblock copolymer of general formula E106 P70 E106 to a thickening agent is from about 40:1 to about 5:1. In some embodiments, the thickening agent is carboxymethyl cellulose, hydroxypropyl cellulose or hydroxypropyl methylcellulose.

In some embodiments, the otic and/or vestibular disorder is ototoxicity, chemotherapy-induced hearing loss, sensorineural hearing loss, noise induced hearing loss, excitotoxicity, Meniere's Disease/Syndrome, endolymphatic hydrops, labyrinthitis, Ramsay Hunt's Syndrome, vestibular neuronitis, tinnitus or microvascular compression syndrome.

DETAILED DESCRIPTION OF THE INVENTION

Figure 1:
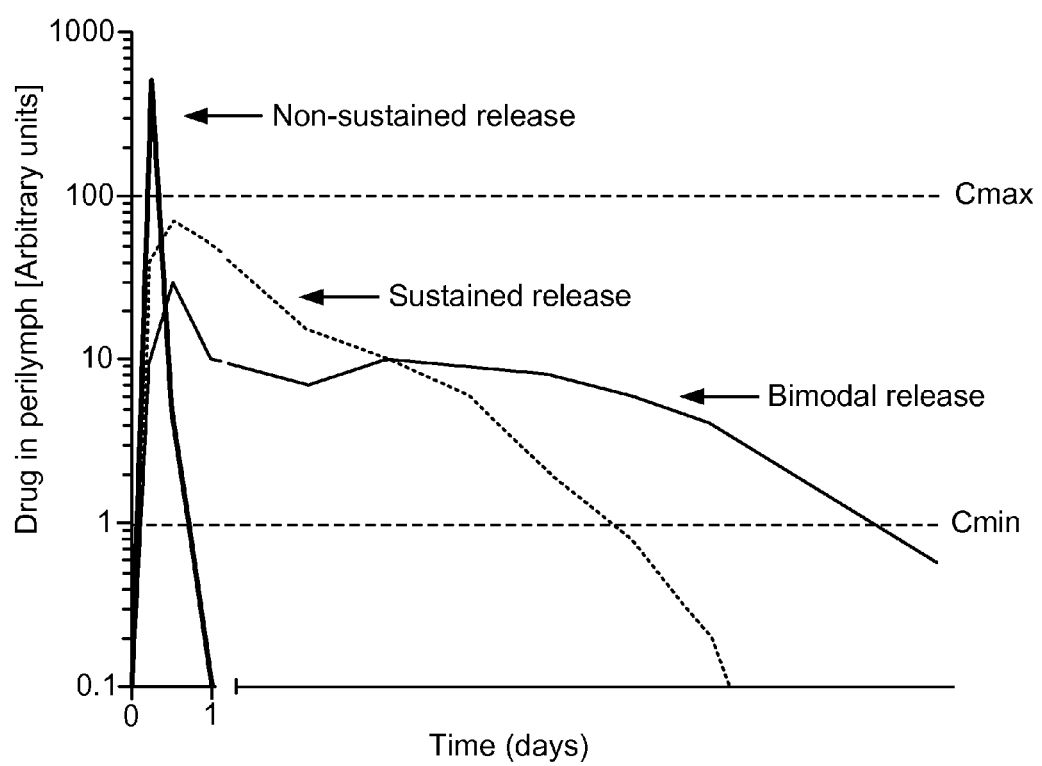
FIG. 1. illustrates a comparison of non-sustained release and sustained release formulations.
Figure 2:
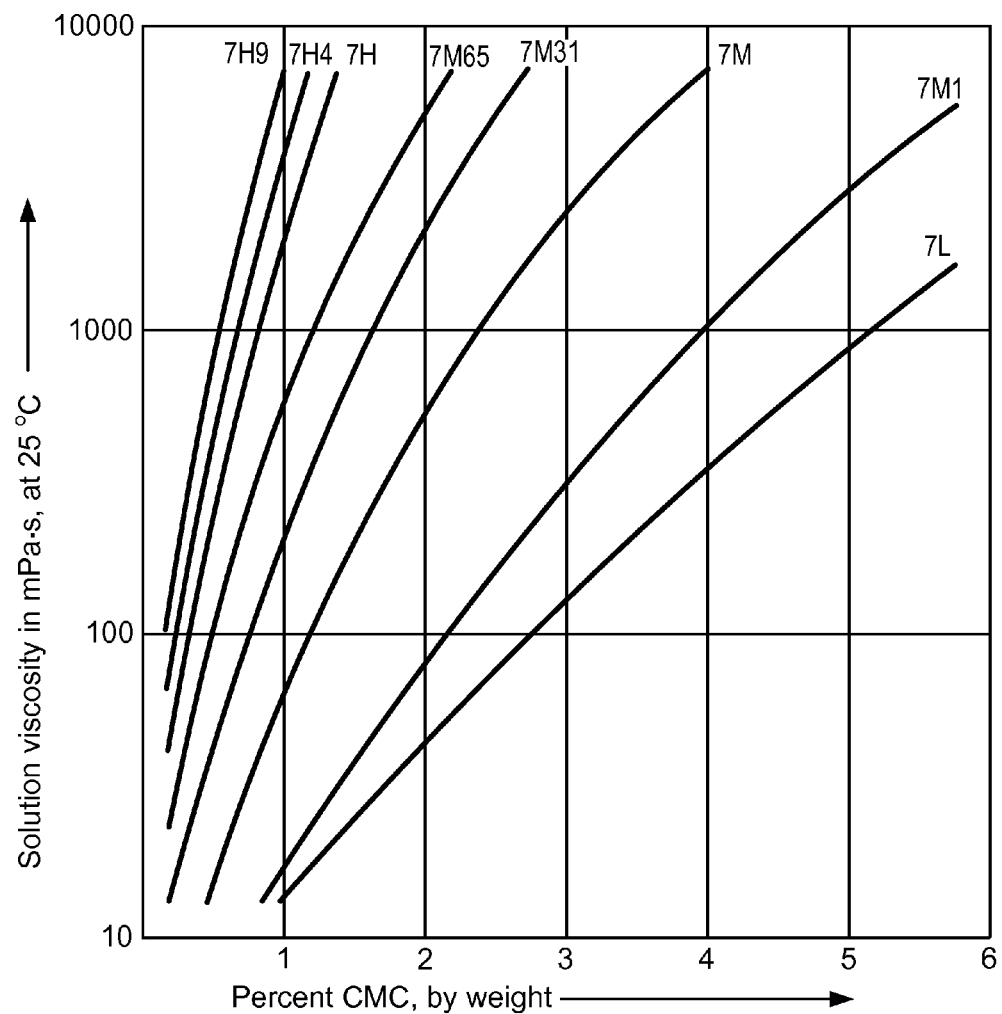
FIG. 2 illustrates the effect of concentration on the viscosity of aqueous solutions of Blanose refined CMC.
Figure 3:
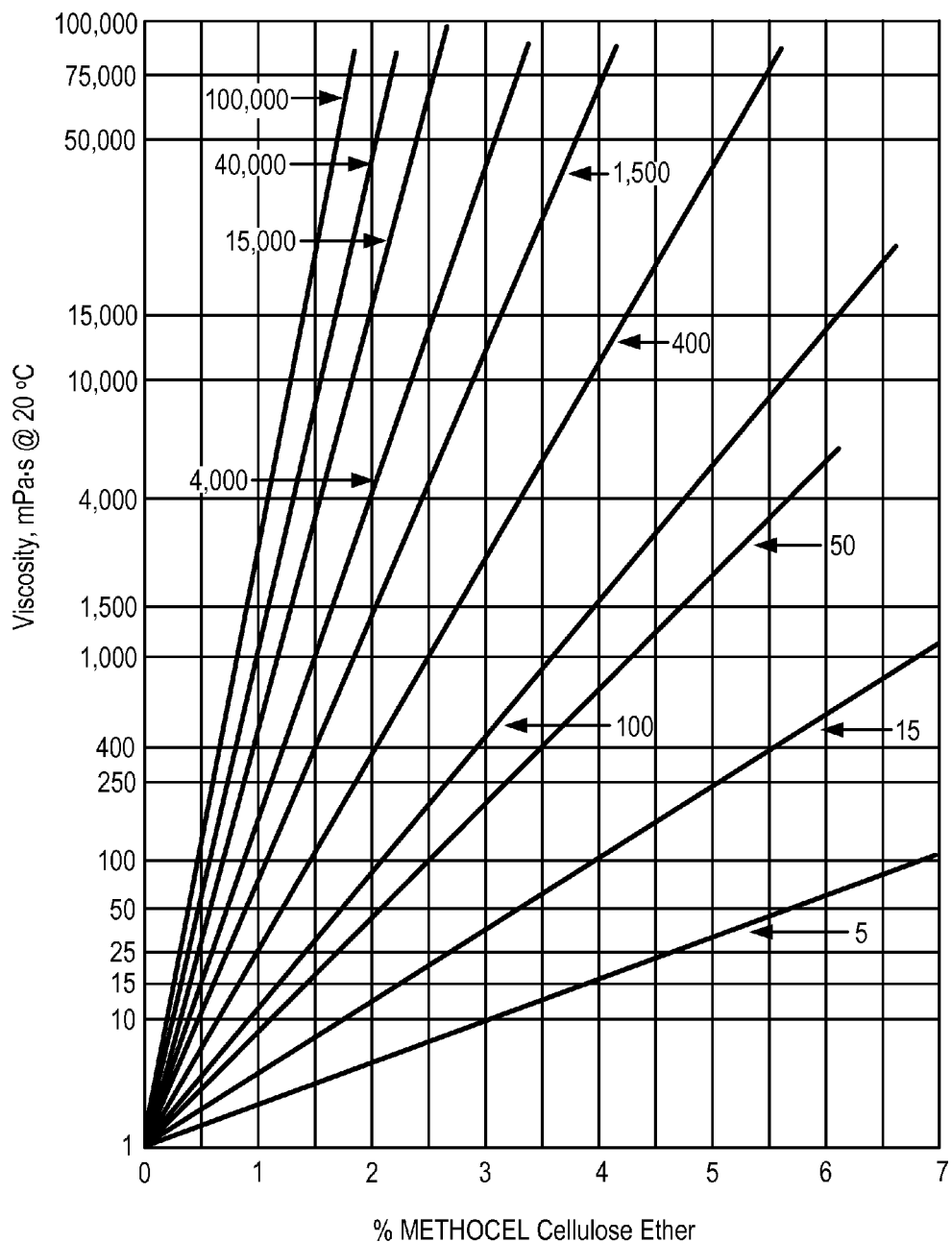
FIG. 3 illustrates the effect of concentration on the viscosity of aqueous solutions of Methocel.

Provided herein are controlled release compositions for treating or ameliorating hearing loss or reduction resulting from destroyed, stunted, malfunctioning, damaged, fragile or missing hairs in the inner ear. In one embodiment, the controlled release composition comprises a therapeutically-effective amount of at least one modulator of growth and/or regeneration of auris sensory cells (e.g., neuron and/or hair cells of the auris), a controlled release auris-acceptable excipient, and an auris-acceptable vehicle. In one embodiment, the controlled release composition comprises a therapeutically-effective amount of at least one modulator of auris sensory cell damage, a controlled release auris-acceptable excipient, and an auris-acceptable vehicle. In one embodiment, the controlled release composition comprises a therapeutically-effective amount of at least one agent that protects neuron and/or hair cells of the auris from damage or reduces, reverses or delays damage to auris sensory cells, a controlled release auris-acceptable excipient, and an auris-acceptable vehicle.

Further disclosed herein are controlled release auris sensory cell modulating agent compositions and formulations to treat ototoxicity, excitotoxicity, sensorineural hearing loss, noise induced hearing loss, Meniere's Disease/Syndrome, endolymphatic hydrops, labyrinthitis, Ramsay Hunt's Syndrome, vestibular neuronitis, tinnitus and microvascular compression syndrome.

A few therapeutic products are available for the treatment of ototoxicity, excitotoxicity, sensorineural hearing loss, noise induced hearing loss, Meniere's Disease/Syndrome, endolymphatic hydrops, labyrinthitis, Ramsay Hunt's Syndrome, vestibular neuronitis, tinnitus and microvascular compression syndrome; however, systemic routes via oral, intravenous or intramuscular routes are currently used to deliver these therapeutic agents.

Systemic drug administration may create a potential inequality in drug concentration with higher circulating levels in the serum, and lower levels in the target auris interna organ structures. As a result, fairly large amounts of drug are required to overcome this inequality in order to deliver sufficient, therapeutically effective quantities to the inner ear. Further, bioavailability is often decreased due to metabolism of the drug by the liver. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic (e.g. metabolites of carbamazepine can cause hepatic injuries and death in some patients).

To overcome the toxic and attendant undesired side effects of systemic delivery of auris sensory cell modulating agents (which are generally understood to be toxic to cells), disclosed herein are methods and compositions for local delivery of auris sensory cell modulating agents to auris media and/or auris interna structures. Access to, for example, the vestibular and cochlear apparatus will occur through the auris media or auris interna, including the round window membrane, the oval window/stapes footplate, the annular ligament and through the otic capsule/temporal bone. In further or alternative embodiments, the auris controlled-release formulations are capable of being administered on or near the round window membrane via intratympanic injection. In other embodiments, the auris controlled release formulations are administered on or near the round window or the crista fenestrae cochleae through entry via a post-auricular incision and surgical manipulation into or near the round window or the crista fenestrae cochleae area. Alternatively, the auris controlled release formulation is applied via syringe and needle, wherein the needle is inserted through the tympanic membrane and guided to the area of the round window or crista fenestrae cochleae.

In addition, localized treatment of the auris interna also affords the use of previously undesired therapeutic agents, including agents with poor pK profiles, poor uptake, low systemic release, and/or toxicity issues.

Because of the localized targeting of the auris sensory cell modulating agent formulations and compositions, as well as the biological blood barrier present in the auris interna, the risk of adverse effects will be reduced as a result of treatment with previously characterized toxic or ineffective auris sensory cell modulating agent. Accordingly, also contemplated within the scope of the embodiments herein is the use of auris sensory cell modulating agents in the treatment of ototoxicity, excitotoxicity, sensorineural hearing loss, noise induced hearing loss, Meniere's Disease/Syndrome, endolymphatic hydrops, labyrinthitis, Ramsay Hunt's Syndrome, vestibular neuronitis, tinnitus and microvascular compression syndrome, including therapeutic agents that have been previously rejected by practitioners because of adverse effects or ineffectiveness of the auris sensory cell modulating agent(s).

Also included within the embodiments disclosed herein is the use of additional auris media and/or auris interna-acceptable agents in combination with the auris sensory cell modulating agent formulations and compositions disclosed herein. When used, such agents assist in the treatment of hearing or equilibrium loss or dysfunction resulting from an autoimmune disorder, including vertigo, tinnitus, hearing loss, balance disorders, infections, inflammatory response or combinations thereof. Accordingly, agents that ameliorate or reduce the effects of vertigo, tinnitus, hearing loss, balance disorders, infections, inflammatory response or combinations thereof are also contemplated to be used in combination with the auris sensory cell modulating agent(s) described herein.

In some embodiments, the composition further comprises an auris sensory cell modulating agent as an immediate release agent wherein the immediate release auris sensory cell modulating agent is the same agent as the controlled-release agent, a different auris sensory cell modulating agent, an additional therapeutic agent, or a combination thereof. In some embodiments, the composition further comprises an additional therapeutic agent. In some embodiments, the additional therapeutic agent is an anesthetic, a local acting anesthetic, an analgesic, an antibiotic, an antiemetic, an antifungal, an anti-microbial agent, an antiseptic, an antiviral, a chemotherapeutic agent, a diuretic, a keratolytic agent, an otoprotectant, an immunosuppressant comprising but not limited to such agents as calcineurin inhibitors (cyclosporine, tacrolimus, pimecrolimus), macrolides such as rapamycin, corticosteroids or combinations thereof. In some embodiments, the additional therapeutic agent is an immediate release agent. In some embodiments, the additional therapeutic agent is a controlled release agent.

Accordingly, provided herein are controlled release auris sensory cell modulating agent formulations and compositions to locally treat auris media and/or auris interna structures, thereby avoiding side effects as a result of systemic administration of the auris sensory cell modulating agents. The locally applied auris sensory cell modulating agent formulations and compositions are compatible with auris media and/or auris interna structures, and are administered either directly to the desired auris media and/or auris interna structure, e.g. the cochlear region or the tympanic cavity, or administered to a structure in direct communication with areas of the auris interna, including but not limited to the round window membrane, the crista fenestrae cochleae or the oval window membrane. By specifically targeting the auris media or auris interna structures, adverse side effects as a result of systemic treatment are avoided. Moreover, by providing a controlled release auris sensory cell modulating agent formulation or composition to treat otic disorders, a constant and/or extended source of auris sensory cell modulating agent is provided to the individual or patient suffering from an otic disorder, reducing or eliminating the variability of treatment.

Intratympanic injection of therapeutic agents is the technique of injecting a therapeutic agent behind the tympanic membrane into the auris media and/or auris interna. Despite early success with this technique (Schuknecht, Laryngoscope (1956) 66, 859-870) some challenges do remain. For example, access to the round window membrane, the site of drug absorption into the auris interna, can be challenging.

However, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intra-tympanic compositions: the inner ear provides sui generis formulation challenges. Thus, compositions developed for other parts of the body have little to no relevance for an intra-tympanic composition.

There is no guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic formulations that meet stringent criteria for pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the formulations described herein comprise dyes and aid visualization of the administered compositions obviating the need for invasive procedures (e.g., removal of perilymph) during preclinical and/or clinical development of intratympanic therapeutics.

Provided herein are controlled release auris sensory cell modulating agent formulations and compositions to locally treat targeted auris structures, thereby avoiding side effects as a result of systemic administration of the auris sensory cell modulating agent formulations and compositions. The locally applied auris sensory cell modulating agent formulations and compositions and devices are compatible with the targeted auris structures, and administered either directly to the desired targeted auris structure, e.g. the cochlear region, the tympanic cavity or the external ear, or administered to a structure in direct communication with areas of the auris interna, including but not limited to the round window membrane, the crista fenestrae cochleae or the oval window membrane. By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled release auris sensory cell modulating agent formulation or composition to treat otic disorders, a constant, and/or extended source of auris sensory cell modulating agent is provided to the individual or patient suffering from an otic disorder, reducing or eliminating variabilities in treatment. Accordingly, one embodiment disclosed herein is to provide a composition that enables at least one auris sensory cell modulating agent to be released in therapeutically effective doses either at variable or constant rates such as to ensure a continuous release of the at least one agent. In some embodiments, the auris sensory cell modulating agents disclosed herein are administered as an immediate release formulation or composition. In other embodiments, the auris sensory cell modulating agents are administered as a sustained release formulation, released either continuously, variably or in a pulsatile manner, or variants thereof. In still other embodiments, auris sensory cell modulating agent formulation is administered as both an immediate release and sustained release formulation, released either continuously, variably or in a pulsatile manner, or variants thereof. The release is optionally dependent on environmental or physiological conditions, for example, the external ionic environment (see, e.g. Oros® release system, Johnson & Johnson).

In addition, the auris-acceptable controlled-release auris sensory cell modulating agent formulations and treatments described herein are provided to the target ear region of the individual in need, including the inner ear, and the individual in need is additionally administered an oral dose of auris sensory cell modulating agent. In some embodiments, the oral dose of auris sensory cell modulating agent is administered prior to administration of the auris-acceptable controlled-release auris sensory cell modulating agent formulation, and then the oral dose is tapered off over the period of time that the auris-acceptable controlled-release auris sensory cell modulating agent formulation is provided. Alternatively, the oral dose of auris sensory cell modulating agent is administered during administration of the auris-acceptable controlled-release auris sensory cell modulating agent formulation, and then the oral dose is tapered off over the period of time that the auris-acceptable controlled-release auris sensory cell modulating agent formulation is provided. Alternatively, the oral dose of auris sensory cell modulating agent is administered after administration of the auris-acceptable controlled-release auris sensory cell modulating agent formulation has been initiated, and then the oral dose is tapered off over the period of time that the auris-acceptable controlled-release auris sensory cell modulating agent formulation is provided.

In addition, the auris sensory cell modulating agent pharmaceutical compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, auris sensory cell modulating agent pharmaceutical compositions or formulations or devices disclosed herein are optionally targeted to distinct regions of the targeted auris structures, including but not limited to the tympanic cavity, vestibular bony and membranous labyrinths, cochlear bony and membranous labyrinths and other anatomical or physiological structures located within the auris interna.

Certain Definitions

The term "auris-acceptable" with respect to a formulation, composition or ingredient, as used herein, includes having no persistent detrimental effect on the auris interna (or inner ear) of the subject being treated. By "auris-pharmaceutically acceptable," as used herein, refers to a material, such as a carrier or diluent, which does not abrogate the biological activity or properties of the compound in reference to the auris interna (or inner ear), and is relatively or is reduced in toxicity to the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the auris sensory cell modulating agents disclosed herein.

"Auris interna" refers to the inner ear, including the cochlea and the vestibular labyrinth, and the round window that connects the cochlea with the middle ear.

"Auris-interna bioavailability" refers to the percentage of the administered dose of compounds disclosed herein that becomes available in the inner ear of the animal or human being studied.

"Auris media" refers to the middle ear, including the tympanic cavity, auditory ossicles and oval window, which connects the middle ear with the inner ear.

"Balance disorder" refers to a disorder, illness, or condition which causes a subject to feel unsteady, or to have a sensation of movement. Included in this definition are dizziness, vertigo, disequilibrium, and pre-syncope. Diseases which are classified as balance disorders include, but are not limited to, Ramsay Hunt's Syndrome, Meniere's Disease, mal de debarquement, benign paroxysmal positional vertigo, and labyrinthitis.

"Blood plasma concentration" refers to the concentration of compounds provided herein in the plasma component of blood of a subject.

"Carrier materials" are excipients that are compatible with the auris sensory cell modulating agent, the auris interna and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute the auris sensory cell modulating agent prior to delivery and which are compatible with the auris interna.

"Dispersing agents," and/or "viscosity modulating agents" are materials that control the diffusion and homogeneity of the auris sensory cell modulating agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Dispersing agents useful in liposomal dispersions and self-emulsifying dispersions of the auris sensory cell modulating agents disclosed herein are dimyristoyl phosphatidyl choline, natural phosphatidyl choline from eggs, natural phosphatidyl glycerol from eggs, cholesterol and isopropyl myristate.

"Drug absorption" or "absorption" refers to the process of movement of the auris sensory cell modulating agents from the localized site of administration, by way of example only, the round window membrane of the inner ear, and across a barrier (the round window membranes, as described below) into the auris interna or inner ear structures. The terms "co-administration" or the like, as used herein, are meant to encompass administration of the auris sensory cell modulating agents to a single patient, and are intended to include treatment regimens in which the auris sensory cell modulating agents are administered by the same or different route of administration or at the same or different time.

The terms "effective amount" or "therapeutically effective amount," as used herein, refer to a sufficient amount of the auris sensory cell modulating agent being administered that would be expected to relieve to some extent one or more of the symptoms of the disease or condition being treated. For example, the result of administration of the auris sensory cell modulating agent disclosed herein is reduction and/or alleviation of the signs, symptoms, or causes of tinnitus or balance disorders. For example, an "effective amount" for therapeutic uses is the amount of auris sensory cell modulating agent, including a formulation as disclosed herein required to provide a decrease or amelioration in disease symptoms without undue adverse side effects. The term "therapeutically effective amount" includes, for example, a prophylactically effective amount. An "effective amount" of a modulator of neuron and/or hair cells of the auris composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

The terms "enhance" or "enhancing" refers to an increase or prolongation of either the potency or duration of a desired effect of auris sensory cell modulating agent, or a diminution of any adverse symptomatology that is consequent upon the administration of the therapeutic agent. Thus, in regard to enhancing the effect of the auris sensory cell modulating agents disclosed herein, the term "enhancing" refers to the ability to increase or prolong, either in potency or duration, the effect of other therapeutic agents that are used in combination with the auris sensory cell modulating agent disclosed herein. An "enhancing-effective amount," as used herein, refers to an amount of auris sensory cell modulating agent or other therapeutic agent which is adequate to enhance the effect of another therapeutic agent or auris sensory cell modulating agent of the target auris structure in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, or advancement of a condition in a patient necessitating treatment.

The terms "kit" and "article of manufacture" are used as synonyms.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

"Modulator of neuron and/or hair cells of the auris" and "auris sensory cell modulating agent" are synonyms. They include agents that promote the growth and/or regeneration of neurons and/or the hair cells of the auris, and agents that destroy neurons and/or hair cells of the auris. In some embodiments, an auris sensory cell modulating agent provides therapeutic benefit (e.g., alleviation of hearing loss) by promoting the growth and/or regeneration of auris sensory cells (e.g., neurons and/or the hair cells) of the auris. In some embodiments, an auris sensory cell modulating agent (e.g., a toxicant) provides therapeutic benefit (e.g., alleviation of vertigo) by destroying or damaging auris sensory cells (e.g., neurons and/or hair cells of the auris). In some embodiments, an auris sensory cell modulating agent provides therapeutic benefit (e.g., alleviation of tinnitus due to acoustic trauma) by treating and/or reversing damage to auris sensory cells (e.g., dysfunction of neurons and/or hair cells of the auris) or reducing or delaying further damage (e.g., cell death) to auris sensory cells (e.g., by exerting an otoprotectant effect or a trophic effect).

The term "trophic agent" means an agent that promotes the survival, growth and/or regeneration of auris sensory cells (e.g., neurons and/or the hair cells of the auris). In some embodiments, a trophic agent reduces or inhibits oxidative damage and/or osteoneogenesis and/or degeneration of auris sensory cells. In some embodiments, a trophic agent maintains healthy auris sensory cells (e.g., after a surgical implant of a medical device). In some embodiments, a trophic agent upregulates activity of antioxidant enzymes (e.g., during administration of ototoxic agents). In some embodiments, a trophic agent is an immunosuppressant (e.g., an immunosuppressant used during otic surgery). In some embodiments, a trophic agent is a growth factor (e.g., a growth factor used after an implantation procedure to promote growth of auris cells).

The term "glutamate receptor antagonist" means a compound that interferes with or inhibits the activity of a glutamate receptor. In some embodiments, the receptor is an AMPA receptor, or NMDA receptor. In some embodiments, a glutamate receptor antagonist binds to a glutamate receptor but said binding does not produce a physiological response. Glutamate receptor antagonists include partial agonists, inverse agonists, neutral or competitive antagonists, non-competitive antagonists, allosteric antagonists, and/or orthosteric antagonists.

The term "glutamate receptor agonist" means a compound that binds to a glutamate receptor and activates the receptor. The term further includes a compound that facilitates the binding of a native ligand. In some embodiments, the receptor is an mGlu receptor. Glutamate receptor agonists include partial antagonists, allosteric agonists, and/or orthosteric agonists.

In prophylactic applications, compositions comprising the auris sensory cell modulating agents described herein are administered to a patient susceptible to or otherwise at risk of a particular disease, disorder or condition. For example, such conditions include and are not limited to ototoxicity, excitotoxicity, sensorineural hearing loss, noise induced hearing loss, Meniere's Disease/Syndrome, endolymphatic hydrops, labyrinthitis, Ramsay Hunt's Syndrome, vestibular neuronitis, tinnitus and microvascular compression syndrome. Such an amount is defined to be a "prophylactically effective amount or dose." In this use, the precise amounts also depend on the patient's state of health, weight, and the like.

As used herein, a "pharmaceutical device" includes any composition described herein that, upon administration to an ear, provides a reservoir for extended release of an active agent described herein.

The term "substantially low degradation products" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent. In some embodiments, any individual impurity (e.g., metal impurity, degradation products of active agent and/or excipients, or the like) present in a formulation described herein is less than 5%, less than 2%, or less than 1% by weight of the active agent. In some embodiments the formulation does not contain precipitate during storage or change in color after manufacturing and storage.

As used herein "essentially in the form of micronized powder" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent.

The term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. Otic surgery includes middle ear surgery, inner ear surgery, tympanostomy, cochleostomy, labyrinthotomy, mastoidectomy, stapedectomy, stapedotomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

A "prodrug" refers to an auris sensory cell modulating agent that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Solubilizers" refer to auris-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like that assist or increase the solubility of the auris sensory cell modulating agents disclosed herein.

"Stabilizers" refers to compounds such as any antioxidation agents, buffers, acids, preservatives and the like that are compatible with the environment of the auris interna. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the auris interna is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject may be used interchangeably.

"Surfactants" refer to compounds that are auris-acceptable, such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition, for example tinnitus, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Anatomy of the Ear

Figure 4:
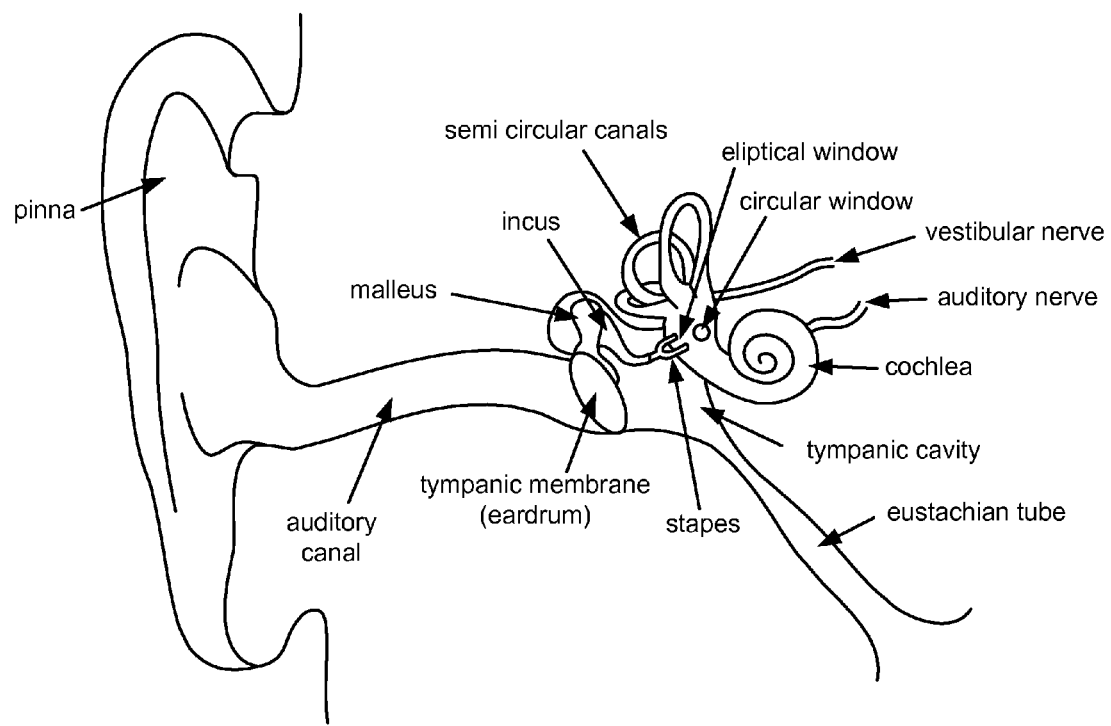
FIG. 4 illustrates the anatomy of the ear

As shown in FIG. 4, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Diseases

Otic disorders produce symptoms which include but are not limited to hearing loss, nystagmus, vertigo, tinnitus, inflammation, infection and congestion. The otic disorders which are treated with the compositions disclosed herein are numerous and include ototoxicity, excitotoxicity, sensorineural hearing loss, noise induced hearing loss, Meniere's Disease/Syndrome, endolymphatic hydrops, labyrinthitis, Ramsay Hunt's Syndrome, vestibular neuronitis, tinnitus and microvascular compression syndrome.

Excitotoxicity

Excitotoxicity refers to the death or damaging of neurons and/or otic hair cells by glutamate and/or similar substances.

Glutamate is the most abundant excitatory neurotransmitter in the central nervous system. Pre-synaptic neurons release glutamate upon stimulation. It flows across the synapse, binds to receptors located on post-synaptic neurons, and activates these neurons. The glutamate receptors include the NMDA, AMPA, and kainate receptors. Glutamate transporters are tasked with removing extracellular glutamate from the synapse. Certain events (e.g. ischemia or stroke) can damage the transporters. This results in excess glutamate accumulating in the synapse. Excess glutamate in synapses results in the over-activation of the glutamate receptors.

The AMPA receptor is activated by the binding of both glutamate and AMPA. Activation of certain isoforms of the AMPA receptor results in the opening of ion channels located in the plasma membrane of the neuron. When the channels open, $Na+$ and $Ca2+$ ions flow into the neuron and $K+$ ions flow out of the neuron.

The NMDA receptor is activated by the binding of both glutamate and NMDA. Activation of the NMDA receptor, results in the opening of ion channels located in the plasma membrane of the neuron. However, these channels are blocked by $Mg2+$ ions. Activation of the AMPA receptor results in the expulsion of $Mg2+$ ions from the ion channels into the synapse. When the ion channels open, and the $Mg2+$ ions evacuate the ion channels, $Na+$ and $Ca2+$ ions flow into the neuron, and $K+$ ions flow out of the neuron.

Excitotoxicity occurs when the NMDA receptor and AMPA receptors are over-activated by the binding of excessive amounts of ligands, for example, abnormal amounts of glutamate. The over-activation of these receptors causes excessive opening of the ion channels under their control. This allows abnormally high levels of $Ca2+$ and $Na+$ to enter the neuron. The influx of these levels of $Ca2+$ and $Na+$ into the neuron causes the neuron to fire more often, resulting in a rapid buildup of free radicals and inflammatory compounds within the cell. The free radicals eventually damage the mitochondria, depleting the cell's energy stores. Furthermore, excess levels of $Ca2+$ and $Na+$ ions activate excess levels of enzymes including, but not limited to, phospholipases, endonucleases, and proteases. The over-activation of these enzymes results in damage to the cytoskeleton, plasma membrane, mitochondria, and DNA of the sensory neuron. In some embodiments, an auris sensory cell modulating agent is a glutamate receptor antagonist that reduces or inhibits excessive neuronal firing and/or neuronal cell death. Disclosed herein, in certain embodiments, is a pharmaceutical composition for use in the treatment of a disease of the ear characterized by the dysfunction of an NMDA receptor.

Tinnitus

As used herein, "tinnitus" refers to a disorder characterized by the perception of sound in the absence of any external stimuli. In certain instances, tinnitus occurs in one or both ears, continuously or sporadically, and is most often described as a ringing sound. It is most often used as a diagnostic symptom for other diseases. There are two types of tinnitus: objective and subjective. The former is a sound created in the body which is audible to anyone. The latter is audible only to the affected individual. Studies estimate that over 50 million Americans experience some form of tinnitus. Of those 50 million, about 12 million experience severe tinnitus.

There are several treatments for tinnitus. Lidocaine, administered by IV, reduces or eliminates the noise associated with tinnitus in about 60-80% of sufferers. Selective neurotransmitter reuptake inhibitors, such as nortriptyline, sertraline, and paroxetine, have also demonstrated efficacy against tinnitus. Benzodiazepines are also prescribed to treat tinnitus. In some embodiments, an auris sensory cell modulating agent reduces or inhibits auris sensory cell damage and/or death associated with tinnitus.

Sensorineural Hearing Loss

Sensorineural hearing loss is a type of hearing loss which results from defects (congenital and acquired) in the vestibulocochlear nerve (also known as cranial nerve VIII), or sensory cells of the inner ear. The majority of defects of the inner ear are defects of otic hair cells.

Aplasia of the cochlea, chromosomal defects, and congenital cholesteatoma are examples of congenital defects which can result in sensorineural hearing loss. By way of non-limiting example, inflammatory diseases (e.g. suppurative labyrinthitis, meningitis, mumps, measles, viral syphilis, and autoimmune disorders), Meniere's Disease, exposure to ototoxic drugs (e.g. aminoglycosides, loop diuretics, antimetabolites, salicylates, and cisplatin), physical trauma, presbyacusis, and acoustic trauma (prolonged exposure to sound in excess of 90 dB) can all result in acquired sensorineural hearing loss.

If the defect resulting in sensorineural hearing loss is a defect in the auditory pathways, the sensorineural hearing loss is called central hearing loss. If the defect resulting in sensorineural hearing loss is a defect in the auditory pathways, the sensorineural hearing loss is called cortical deafness. In some embodiments, an auris sensory cell modulating agent is a trophic agent (e.g., BDNF, GDNF) that promotes growth of auris sensory cells and reduces or reverses sensorineural hearing loss.

Noise Induced Hearing Loss

Noise induced hearing loss (NIHL) is caused upon exposure to sounds that are too loud or loud sounds that last an extended period of time. Long or repeated or impulse exposure to sounds at or above 85 decibels can cause hearing loss. Hearing loss may also occur from prolonged exposure to loud noises, such as loud music, heavy equipment or machinery, airplanes, gunfire or other human-based noises. NIHL causes damage to the hair cells and/or the auditory nerve. The hair cells are small sensory cells that convert sound energy into electrical signals that travel to the brain. Impulse sound can result in immediate hearing loss that may be permanent. This kind of hearing loss may be accompanied by tinnitus—a ringing, buzzing, or roaring in the ears or head—which may subside over time. Hearing loss and tinnitus may be experienced in one or both ears, and tinnitus may continue constantly or occasionally throughout a lifetime. Continuous exposure to loud noise also damages the structure of hair cells, resulting in permanent hearing loss and tinnitus, although the process occurs more gradually than for impulse noise.

In some embodiments, an otoprotectant can reverse, reduce or ameliorate NIHL. Examples of otoprotectants that treat or prevent NIHL include, but are not limited to, otoprotectants described herein.

Ototoxicity

Ototoxicity refers to hearing loss caused by a toxin. The hearing loss may be due to trauma to otic hair cells, the cochlea, and/or the cranial nerve VII. Multiple drugs are known to be ototoxic. Often ototoxicity is dose-dependent. It may be permanent or reversible upon withdrawal of the drug.

Known ototoxic drugs include, but are not limited to, the aminoglycoside class of antibiotics (e.g. gentamicin, and amikacin), some members of the macrolide class of antibiotics (e.g. erythromycin), some members of the glycopeptide class of antibiotics (e.g. vancomycin), salicylic acid, nicotine, some chemotherapeutic agents (e.g. actinomycin, bleomycin, cisplatin, carboplatin and vincristine), and some members of the loop diuretic family of drugs (e.g. furosemide), 6-hydroxy dopamine (6-OH DPAT), 6,7-dinitroquinoxaline-2,3-dione (DNQX) or the like.

Cisplatin and the aminoglycoside class of antibiotics induce the production of reactive oxygen species ("ROS"). ROS can damage cells directly by damaging DNA, polypeptides, and/or lipids. Antioxidants prevent damage of ROS by preventing their formation or scavenging free radicals before they can damage the cell. Both cisplatin and the aminoglycoside class of antibiotics are also thought to damage the ear by binding melanin in the stria vascularis of the inner ear.

Salicylic acid is classified as ototoxic as it inhibits the function of the polypeptide prestin. Prestin mediates outer otic hair cell motility by controlling the exchange of chloride and carbonate across the plasma membrane of outer otic hair cells. It is only found in the outer otic hair cells, not the inner otic hair cells. Accordingly, disclosed herein is the use of controlled release auris-compositions comprising otoprotectants (e.g. antioxidants) to prevent, ameliorate or lessen ototoxic effects of chemotherapy, including but not limited to cisplatin treatment, aminoglycoside or salicylic acid administration, or other ototoxic agents.

Endolymphatic Hydrops

Endolymphatic hydrops refers to an increase in the hydraulic pressure within the endolymphatic system of the inner ear. The endolymph and perilymph are separated by thin membranes which contain multiple nerves. Fluctuation in pressure stresses the membranes and the nerves they house. If the pressure is great enough, disruptions may form in these membranes. This results in a mixing of the fluids which can lead to a depolarization blockade and transient loss of function. Changes in the rate of vestibular nerve firing often leads to vertigo. Further, the organ of Corti may also be affected. Distortions of the basilar membrane and the inner and outer hair cells can lead to hearing loss and/or tinnitus.

Causes include metabolic disturbances, hormonal imbalances, autoimmune disease, and viral, bacterial, or fungal infections. Symptoms include hearing loss, vertigo, tinnitus, and aural fullness. Nystagmus may also be present. Treatment includes systemic administration of benzodiazepine, diuretics (to decrease the fluid pressure), corticosteroids, and/or anti-bacterial, anti-viral, or anti-fungal agents.

Labyrinthitis

Labyrinthitis is an inflammation of the labyrinths of the ear which contain the vestibular system of the inner ear. Causes include bacterial, viral, and fungal infections. It may also be caused by a head injury or allergies. Symptoms of labyrinthitis include difficulty maintaining balance, dizziness, vertigo, tinnitus, and hearing loss. Recovery may take one to six weeks; however, chronic symptoms may be present for years.

There are several treatments for labyrinthitis. Prochlorperazine is often prescribed as an antiemetic. Serotonin-reuptake inhibitors have been shown to stimulate new neural growth within the inner ear. Additionally, treatment with antibiotics is prescribed if the cause is a bacterial infection, and treatment with corticosteroids and antivirals is recommended if the condition is caused by a viral infection.

Meniere's Disease

Meniere's Disease is an idiopathic condition characterized by sudden attacks of vertigo, nausea and vomiting that may last for 3 to 24 hours, and may subside gradually. Progressive hearing loss, tinnitus and a sensation of pressure in the ears accompanies the disease through time. The cause of Meniere's disease is likely related to an imbalance of inner ear fluid homeostasis, including an increase in production or a decrease in reabsorption of inner ear fluid.

Studies of the vasopressin (VP)-mediated aquaporin 2 (AQP2) system in the inner ear suggest a role for VP in inducing endolymph production, thereby increasing pressure in the vestibular and cochlear structures. VP levels were found to be upregulated in endolymphatic hydrops (Meniere's Disease) cases, and chronic administration of VP in guinea pigs was found to induce endolymphatic hydrops. Treatment with VP antagonists, including infusion of OPC-31260 (a competitive antagonist of V2-R) into the scala tympani resulted in a marked reduction of Meniere's disease symptoms. Other VP antagonists include WAY-140288, CL-385004, tolvaptan, conivaptan, SR 121463A and VPA 985. (Sanghi et al. Eur. Heart J. (2005) 26:538-543; Palm et al. Nephrol. Dial Transplant (1999) 14:2559-2562).

Other studies suggest a role for estrogen-related receptor β/NR3B2 (ERR/Nr3b2) in regulating endolymph production, and therefore pressure in the vestibular/cochlear apparatus. Knock-out studies in mice demonstrate the role of the polypeptide product of the Nr3b2 gene in regulating endolymph fluid production. Nr3b2 expression has been localized in the endolymph-secreting strial marginal cells and vestibular dark cells of the cochlea and vestibular apparatus, respectively. Moreover, conditional knockout of the Nr3b2 gene results in deafness and diminished endolymphatic fluid volume. Treatment with antagonists to ERR/Nr3b2 may assist in reducing endolymphatic volume, and thus alter pressure in the auris interna structures.

Other treatments may be aimed at dealing with the immediate symptoms and prevention of recurrence. Low-sodium diets, avoidance of caffeine, alcohol, and tobacco have been advocated. Medications that may temporarily relieve vertigo attacks include antihistamines (including meclizine and other antihistamines), and central nervous system agents, including barbiturates and/or benzodiazepines, including lorazepam or diazepam. Other examples of drugs that may be useful in relieving symptoms include muscarinic antagonists, including scopolamine. Nausea and vomiting may be relieved by suppositories containing antipsychotic agents, including the phenothiazine agent prochlorperazine.

Surgical procedures that have been used to relieve symptoms include the destruction of vestibular and/or cochlear function to relieve vertigo symptoms. These procedures aim to either reduce fluid pressure in the inner ear and/or to destroy inner ear balance function. An endolymphatic shunt procedure, which relieves fluid pressure, may be placed in the inner ear to relieve symptoms of vestibular dysfunction. Other treatments include gentamicin application, which when injected into the eardrum destroys sensory hair cell function, thereby eradicating inner ear balance function. Severing of the vestibular nerve may also be employed, which while preserving hearing, may control vertigo. In some embodiments, an auris sensory cell modulator promotes growth of hair cells and allows a subject to regain inner ear balance function.

Meniere's Syndrome

Meniere's Syndrome, which displays similar symptoms as Meniere's disease, is attributed as a secondary affliction to another disease process, e.g. thyroid disease or inner ear inflammation due to syphilis infection. Meniere's syndrome, thus, are secondary effects to various process that interfere with normal production or resorption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Ramsay Hunt's Syndrome (Herpes Zoster Infection)

Ramsay Hunt's Syndrome is caused by a herpes zoster infection of the auditory nerve. The infection may cause severe ear pain, hearing loss, vertigo, as well as blisters on the outer ear, in the ear canal, as well as on the skin of the face or neck supplied by the nerves. Facial muscles may also become paralyzed if the facial nerves are compressed by the swelling. Hearing loss may be temporary or permanent, with vertigo symptoms usually lasting from several days to weeks.

Treatment of Ramsay Hunt's syndrome includes administration of antiviral agents, including acyclovir. Other antiviral agents include famciclovir and valacyclovir. Combination of antiviral and corticosteroid therapy may also be employed to ameliorate herpes zoster infection. Analgesics or narcotics may also be administered to relieve the pain, and diazepam or other central nervous system agents to suppress vertigo. Capsaicin, lidocaine patches and nerve blocks are optionally used. Surgery may also be performed on compressed facial nerves to relieve facial paralysis.

Microvascular Compression Syndrome

Microvascular compression syndrome (MCS), also called "vascular compression" or "neurovascular compression", is a disorder characterized by vertigo and tinnitus. It is caused by the irritation of Cranial Nerve VII by a blood vessel. Other symptoms found in subjects with MCS include, but are not limited to, severe motion intolerance, and neuralgic like "quick spins". MCS is treated with carbamazepine, TRILEPTAL®, and baclofen. It can also be surgically treated.

Vestibular Neuronitis

Vestibular neuronitis, or vestibular neuropathy, is an acute, sustained dysfunction of the peripheral vestibular system. It is theorized that vestibular neuronitis is caused by a disruption of afferent neuronal input from one or both of the vestibular apparatuses. Sources of this disruption include viral infection and acute localized ischemia of the vestibular nerve and/or labyrinth.

The most significant finding when diagnosing vestibular neuronitis is spontaneous, unidirectional, horizontal nystagmus. It is often accompanied by nausea, vomiting, and vertigo. It is, however, generally not accompanied by hearing loss or other auditory symptoms.

There are several treatments for vestibular neuronitis. H1-receptor antagonists, such as dimenhydrinate, diphenhydramine, meclizine, and promethazine, diminish vestibular stimulation and depress labyrinthine function through anticholinergic effects. Benzodiazepines, such as diazepam and lorazepam, are also used to inhibit vestibular responses due to their effects on the GABAA receptor. Anticholinergics, for example scopolamine, are also prescribed. They function by suppressing conduction in the vestibular cerebellar pathways. Finally, corticosteroids (i.e. prednisone) are prescribed to ameliorate the inflammation of the vestibular nerve and associated apparatus.

Pharmaceutical Agents

Provided herein are auris sensory cell modulating agent compositions or formulations that modulate the degeneration of auris sensory cells (e.g., neurons and/or hair cells of the auris). In some embodiments, auris sensory cell modulating agent compositions or formulations described herein reduce or delay or reverse the degeneration of auris sensory cells (e.g., neurons and/or hair cells of the auris). Also disclosed herein are controlled release compositions for treating or ameliorating hearing loss or reduction resulting from destroyed, stunted, malfunctioning, damaged, fragile or missing hairs in the inner ear. Additionally provided herein are auris sensory cell modulating agent compositions or formulations that promote the growth and/or regeneration of auris sensory cells (e.g., neurons and/or hair cells of the auris). In some embodiments, auris sensory cell modulating agent compositions or formulations destroy auris sensory cells (e.g., neurons and/or hair cells of the auris). In some embodiments, auris sensory cell modulating agents are otoprotectants and reduce, reverse or delay damage to auris sensory cells (e.g., neurons and/or hair cells of the auris).

Otic and vestibular disorders have causes and symptoms that are responsive to the pharmaceutical agents disclosed herein, or other pharmaceutical agents. Auris sensory cell modulating agents which are not disclosed herein but which ameliorate or eradicate otic disorders are expressly included and intended within the scope of the embodiments presented.

Moreover, pharmaceutical agents which have been previously shown to be toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways or through poor pK characteristics, are useful in some embodiments herein. Accordingly, pharmaceutical agents which have limited or no systemic release, systemic toxicity, poor pK characteristics or combinations thereof are contemplated within the scope of the embodiments disclosed herein.

The auris sensory cell modulating agent formulations disclosed herein are optionally targeted directly to otic structures where treatment is needed; for example, one embodiment contemplated is the direct application of the auris sensory cell modulating agent formulations disclosed herein onto the round window membrane or the crista fenestrae cochlea of the auris interna, allowing direct access and treatment of the auris interna, or inner ear components. In other embodiments, the auris sensory cell modulating agent formulation disclosed herein is applied directly to the oval window. In yet other embodiments, direct access is obtained through microinjection directly into the auris interna, for example, through cochlear microperfusion. Such embodiments also optionally comprise a drug delivery device, wherein the drug delivery device delivers the auris sensory cell modulating agent formulations through use of a needle and syringe, a pump, a microinjection device, an auris-acceptable in situ forming spongy material or any combination thereof.

Some pharmaceutical agents, either alone or in combination, are ototoxic. For example, some chemotherapeutic agents, including actinomycin, bleomycin, cisplatin, carboplatin and vincristine; and antibiotics, including erythromycin, gentamicin, streptomycin, dihydrostreptomycin, tobramycin, netilmicin, amikacin, neomycin, kanamycin, etiomycin, vancomycin, metronidizole, capreomycin, are mildly to very toxic, and affect the vestibular and cochlear structures differentially. However, in some instances, the combination of an ototoxic drug, for example cisplatin, gentamicin, in combination with an otoprotectant is lessens the ototoxic effects of the drug. Moreover, the localized application of the potentially ototoxic drug also lessens the toxic effects that would otherwise occur through systemic application through the use of lower amounts with maintained efficacy, or the use of targeted amounts for a shorter period of time.

In some embodiments, the auris sensory cell modulating agent formulations disclosed herein further comprise otoprotectants that reduce, inhibit or ameliorate the ototoxicity of agents such as chemotherapeutic agents and/or antibiotics as described herein, or reduce, inhibit or ameliorate the effects of other environmental factors, including excessive noise and the like. Examples of otoprotectants include, and are not limited to, otoprotectants described herein, thiols and/or thiol derivatives and/or pharmaceutically acceptable salts, or derivatives (e.g. prodrugs) thereof.

Otoprotectants allow for the administration of ototoxic agents and/or antibiotics at doses that are higher than maximal toxic doses; the ototoxic agents and/or antibiotics would otherwise be administered at lower doses due to ototoxicity. An otoprotectant, when optionally administered by itself, also allows for the amelioration, reduction or elimination of the effect of environmental factors that contribute to loss of hearing and attendant effects, including but not limited to noise-induced hearing loss and tinnitus.

The amount of otoprotectant in any formulation described herein on a mole:mole basis in relation to the ototoxic chemotherapeutic agent (e.g. cis platin) and/or an ototoxic antibiotic (e.g. gentamicin) is in the range of from about 5:1 to about 200:1, from about 5:1 to about 100:1, or from about 5:1 to about 20:1. The amount of otoprotectant in any formulation described herein on a molar basis in relation to the ototoxic chemotherapeutic agent (e.g. cis platin) and/or an ototoxic antibiotic (e.g. gentamicin) is about 50:1, about 20:1 or about 10:1. Any auris sensory cell modulating agent formulation described herein comprises from about 10 mg/ml to about 50 mg/ml, from about 20 mg/ml to about 30 mg/ml, or from 10 mg/mL to about 25 mg/ml of otoprotectant.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release auris sensory cell modulating agent formulation, it is advised to avoid or combine the appropriate excipients, diluents or carriers to lessen or eliminate potential ototoxic components from the formulation, or to decrease the amount of such excipients, diluents or carriers. Optionally, a controlled release auris sensory cell modulating agent formulation includes otoprotective agents, such as antioxidants, alpha lipoic acid, calcium, fosfomycin or iron chelators, to counteract potential ototoxic effects that may arise from the use of specific therapeutic agents or excipients, diluents or carriers.

Amifostine

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which rescue neurons and otic hair cells from cisplatin-induced ototoxicity.

Amifostine (also known as WR-2721, or ETHYOL®) is an otoprotective agent. In certain instances, it prevents or ameliorates the damage to neuron and otic hair cells caused by cisplatin. In certain instances, doses at or above 40 mg/kg are needed to protect against or ameliorate the ototoxic effects of cisplatin.

Salicylic Acid

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of salicylic acid. In certain instances, salicyclic acid is an antioxidant and when administered before treatment with an aminoglycoside, it protects otic hair cells and spiral ganglion neurons from aminoglycoside ototoxicity.

Modulation of Atoh/Math1

Contemplated for use with the formulations disclosed herein are agents that promote the growth and/or regeneration of neurons and/or otic hair cells. Atoh1 is a transcription factor which binds to an E-box. In certain instances, it is expressed during the development of the hair cells of the vestibular and auditory systems. In certain instances, mice with Atoh1 knocked-out did not develop otic hair cells. In certain instances, adenoviruses expressing Atoh1 stimulate the growth and/or regeneration of otic hair cells in guinea pigs treated with ototoxic antibiotics. Accordingly, some embodiments incorporate modulation of the Atoh1 gene.

In some embodiments, a subject is administered a vector engineered to carry the human Atoh1 gene (the "Atoh1 vector"). For disclosures of techniques for creating the Atoh1 vector see U.S. Pub. No. 2004/02475750, which is hereby incorporated by reference for those disclosures. In some embodiments, the Atoh1 vector is a retrovirus. In some embodiments, the Atoh1 vector is not a retrovirus (e.g. it is an adenovirus; a lentivirus; or a polymeric delivery system such as METAFECTENE, SUPERFECT®, EFFECTENE®, or MIRUS TRANSIT).

In some embodiments, the Atoh1 vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

In certain instances, after administration of the Atoh1 vector, the Atoh1 vector infects the cells at the site of administration (e.g. the cells of cochlea, organ of Corti, and/or the vestibular labyrinth). In certain instances the Atoh1 sequence is incorporated into the subject's genome (e.g. when the Atoh1 vector is a retrovirus). In certain instances the therapy will need to be periodically re-administered (e.g. when the Atoh1 vector is not a retrovirus). In some embodiments, the therapy is re-administered annually. In some embodiments, the therapy is re-administered semi-annually. In some embodiments, the therapy is re-administered when the subject's hearing loss is moderate (i.e. the subject cannot consistently hear frequencies less than 41 db to 55 dB) to profound (i.e. the subject cannot consistently hear frequencies less than 90 dB).

In some embodiments, a subject is administered the Atoh1 polypeptide. In some embodiments, the Atoh1 polypeptide is incorporated into controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is placed in contact with the round window membrane.

In some embodiments, a subject is administered a pharmaceutically acceptable agent which modulates the expression of the Atoh1 gene or activity of the Atoh1 polypeptide. In some embodiments, the expression of the Atoh1 gene or activity of the Atoh1 polypeptide is up-regulated. In some embodiments, the expression of the Atoh1 gene or activity of the Atoh1 polypeptide is down-regulated.

In certain instances, a compound which agonizes or antagonizes Atoh1 is identified (e.g. by use of a high throughput screen). In some embodiments, a construct is designed such that a reporter gene is placed downstream of an E-box sequence. In some embodiments, the reporter gene is luciferase, CAT, GFP, β-lactamase or β-galactosidase. In certain instances, the Atoh1 polypeptide binds to the E-box sequence and initiates transcription and expression of the reporter gene. In certain instances, an agonist of Atoh1 aids or facilitates the binding of Atoh1 to the E-box sequence, thus increasing transcription and expression of the reporter gene relative to a pre-determined baseline expression level. In certain instances, an antagonist of Atoh1 blocks the binding of Atoh1 to the E-box, thus decreasing transcription and expression of the reporter gene relative to a pre-determined baseline expression level.

BRN-3 Modulators

Contemplated for use with the formulations disclosed herein are agents that promote the growth and/or regeneration of neurons and/or otic hair cells. BRN-3 is a group of transcription factors that include, but are not limited to, BRN-3a, BRN-3b, and BRN-3c. In certain instances, they are expressed in postmitotic hair cells. In certain instances, the hair cells of mice with BRN-3c knocked-out did not develop stereocilia and/or underwent cell death. In certain instances, BRN3 genes regulate the differentiation of inner ear supporting cells into inner ear sensory cells. Accordingly, some embodiments incorporate modulation of the BRN3 genes, and/or polypeptides.

In some embodiments, a subject is administered a vector engineered to carry a human BRN-3 gene (the "BRN3 vector"). In some embodiments, the BRN3 vector is a retrovirus. In some embodiments, the BRN3 vector is not a retrovirus (e.g. it is an adenovirus; a lentivirus; or a polymeric delivery system such as METAFECTENE, SUPERFECT®, EFFECTENE®, or MIRUS TRANSIT).

In some embodiments, the subject is administered the BRN3 vector before, during, or after exposure to an ototoxic agent (e.g. an aminoglycoside or cisplatin), or a sound of sufficient loudness to induce acoustic trauma.

In some embodiments, the BRN3 vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

In certain instances, after administration of the BRN3 vector, the BRN3 vector infects the cells at the site of administration (e.g. the cells of cochlea, organ of Corti, and/or the vestibular labyrinth). In certain instances the BRN3 sequence is incorporated into the subject's genome (e.g. when the BRN3 vector is a retrovirus). In certain instances the therapy will need to be periodically re-administered (e.g. when the BRN3 vector is not a retrovirus).

In some embodiments, a subject is administered a BRN3 polypeptide. In some embodiments, the BRN3 polypeptide is incorporated into controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is placed in contact with the round window membrane.

In some embodiments, a subject is administered a pharmaceutically acceptable agent which modulates the expression of the BRN3 gene or activity of the BRN3 polypeptide. In some embodiments, the expression of the BRN3 gene or activity of the BRN3 polypeptide is up-regulated. In some embodiments, the expression of the BRN3 gene or activity of the BRN3 polypeptide is down-regulated.

In some embodiments, a compound which agonizes or antagonizes BRN3 is identified (e.g. by use of a high throughput screen). In some embodiments, a construct is designed such that a reporter gene is placed downstream of a BRN3 binding site. In some embodiments, the BRN3 binding site has the sequence ATGAATTAAT (SEQ ID NO: 1) (SBNR3). In some embodiments, the reporter gene is luciferase, CAT, GFP, β-lactamase or β-galactosidase. In certain instances, the BRN3 polypeptide binds to the SBNR3 sequence and initiates transcription and expression of the reporter gene. In certain instances, an agonist of BRN3 aids or facilitates the binding of BRN3 to the SBNR3 sequence, thus increasing transcription and expression of the reporter gene relative to a pre-determined baseline expression level. In certain instances, an antagonist of BRN3 blocks the binding of BRN3 to the SBNR3, thus decreasing transcription and expression of the reporter gene relative to a pre-determined baseline expression level.

Carbamates

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. In certain instances, carbamate compounds protect neurons and otic hair cells from glutamate-induced excitotoxicity. Accordingly, some embodiments incorporate the use of carbamate compounds. In some embodiments, the carbamate compounds are 2-phenyl-1,2-ethanediol monocarbomates and dicarbamates, derivatives thereof, and/or combinations thereof.

Gamma-Secretase Inhibitors

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which inhibit Notch1 signaling. Notch1 is a transmembrane polypeptide which participates in cell development. In some embodiments, the agents which inhibit Notch1 signaling are γ-secretase inhibitors. In certain instances, the inhibition of Notch1 by a γ-secretase inhibitor, following treatment with an ototoxic agent, results in the production/growth of otic hair cells. In some embodiments, the γ-secretase inhibitor is LY450139 (hydroxylvaleryl monobenzocaprolactam), L685458 (1S-benzyl-4R[1-[1-S-carbamoyl-2-phenethylcarbamoyl)-1S-3-methylbutylcarbamoyl]-2R-hydroxy-5-phenylpentyl}carbamic acid tert-butyl ester); LY411575 (N2-[(2S)-2-(3,5-difluorophenyl)-2-hydroxyethanoyl]-N1[(7S)-5-methyl-6-oxo-6,7-dihydro-5H-dibenzo[bid]azepin-7yl]-L-alaninamide), MK-0752 (Merck), tarenflurbil, and/or BMS-299897 (2-[(1R)-1-[[(4-chlorophenyl)sulfony](2,5-difluorophenyl)amino]ethyl]-5-fluorobenzenepropanoic acid).

Glutamate-Receptor Modulators

Provided herein are methods of treating an otic disorder characterized by the dysregulation (e.g., over-activation or over-stimulation) of a glutamate receptor. In some embodiments, a method disclosed herein comprises administering to an individual in need thereof a composition comprising a glutamate receptor antagonist. Glutamate receptor antagonists which are not disclosed herein but which are useful for the amelioration or eradication of otic disorders are expressly included and intended within the scope of the embodiments presented.

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which modulate glutamate receptors. In some embodiments, the glutamate receptor is the AMPA receptor, and/or a group II or III mGlu receptor. In some embodiments, the glutamate receptor is the NMDA receptor. In some embodiments, the glutamate receptor modulator is a glutamate receptor antagonist. In some embodiments, the glutamate receptor antagonist is a non-competitive antagonist. In some embodiments, the glutamate receptor antagonist is a small molecule.

In some embodiments, the agent that modulates the AMPA receptor is an AMPA receptor antagonist. In some embodiments, the agent which antagonizes the AMPA receptors is CNQX (6-cyano-7-nitroquinoxaline-2,3-dione); NBQX (2,3-dihydroxy-6-nitro-7-sulfamoyl-benzo[f]quinoxaline-2,3-dione); DNQX (6,7-dinitroquinoxaline-2,3-dione); kynurenic acid; 2,3-dihydroxy-6-nitro-7-sulfamoylbenzo-[f] quinoxaline; or combinations thereof.

In some embodiments, the glutamate receptor antagonist is an NMDA receptor antagonist. In some embodiments, the agent that modulates the NMDA receptor is an NMDA receptor antagonist. In some embodiments, the glutamate receptor antagonist 1-aminoadamantane; dextromethorphan; dextrorphan; ibogaine; ifenprodil; (S)-ketamine; (R)-ketamine; memantine; dizocilpine (MK-801); gacyclidine; AM-101; traxoprodil; D-2-amino-5-phosphonopentanoic acid (D-AP5); 3-((±)2-carboxypiperazin-4-yl)-propyl-1-phosphonic acid (CPP); conantokin; 7-chlorokynurenate (7-CK); licostinel; nitrous oxide; phencyclidine; riluzole; tiletamine; aptiganel; remacimide; DCKA (5; 7-dichlorokynurenic acid); kynurenic acid; 1-aminocyclopropanecarboxylic acid (ACPC); AP7 (2-amino-7-phosphonoheptanoic acid); APV (R-2-amino-5-phosphonopentanoate); CPPene (3-[(R)-2-carboxypiperazin-4-yl]-prop-2-enyl-1-phosphonic acid); (+)-(1S;2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; (1R*;2R*)-1-(4-hydroxy-3-methylphenyl)-2-(4-(4-fluoro-phenyl)-4-hydroxypiperidin-1-yl)-propan-1-ol-mesylate; or combinations thereof. In some embodiments, the NMDA receptor antagonist is an arylcycloalkylamine. In some embodiments, the NMDA receptor antagonist is (S)-ketamine or a salt thereof. In some embodiments, the NMDA receptor antagonist is a chinazoline. In some embodiments, the NMDA receptor antagonist is 7-CK or a salt thereof. In some embodiments, the NMDA receptor antagonist is AM-101 or a salt thereof.

In some embodiments, the glutamate receptor antagonist is a peptide. In some embodiments, the glutamate receptor antagonist is a fusion peptide comprising (a) a transporter peptide, and (b) a peptide inhibiting interaction of an NMDA receptor with NMDA receptor interacting proteins. As used herein, a "transporter peptide" means a peptide that promotes peptide penetration into cells and tissues. In some embodiments, a transporter peptide is TAT.

In some embodiments, the glutamate receptor antagonist is a fusion peptide comprising (a) a TAT peptide, and (b) a peptide inhibiting interaction of an NMDA receptor with NMDA receptor interacting proteins. In some embodiments, the glutamate receptor antagonist is a fusion peptide comprising (a) a (D)-TAT peptide, and (b) a peptide inhibiting interaction of an NMDA receptor with NMDA receptor interacting proteins. In some embodiments, the glutamate receptor antagonist is a fusion peptide comprising (a) a transporter peptide, and (b) an NR2B9c peptide. In some embodiments, the glutamate receptor antagonist is a fusion peptide comprising (a) a transporter peptide, and (b) a (D)-NR2B9c peptide. In some embodiments, the glutamate receptor antagonist is a fusion peptide comprising (a) a (D)-TAT peptide, and (b) a (D)-NR2B9c peptide. In some embodiments, the glutamate receptor antagonist is a fusion peptide comprising (a) a transporter peptide, and (b) a (L)-NR2B9c peptide.

In certain instances, the over-activation of the AMPA and NMDA glutamate receptors by the binding of excessive amounts of glutamate, results in the excessive opening of the ion channels under their control. In certain instances, this results in abnormally high levels of Ca2+ and Na+ entering the neuron. In certain instances, the influx of Ca2+ and Na+ into the neuron activates multiple enzymes including, but not limited to, phospholipases, endonucleases, and proteases. In certain instances, the over-activation of these enzymes results in damage to the cytoskeleton, plasma membrane, mitochondria, and DNA of the neuron. Further, in certain instances, the transcription of multiple pro-apoptotic genes and anti-apoptotic genes are controlled by Ca2+ levels.

The mGlu receptors, unlike the AMPA and NMDA receptors, do not directly control an ion channel. However, in certain instances, they indirectly control the opening of ion channels by the activation of biochemical cascades. The mGlu receptors are divided into three groups. In certain instances, the members of groups II and III reduce or inhibit post-synaptic potentials by preventing or decreasing the formation of cAMP. In certain instances, this causes a reduction in the release of neurotransmitters, especially glutamate. GRM7 is the gene which encodes the mGlu7 receptor, a group III receptor. In certain instances, the agonism of mGlu7 results in a decrease in synaptic concentrations of glutamate. This ameliorates glutamate excitotoxicity.

In some embodiments, the glutamate receptor is a group II mGlu receptor. In some embodiments, the agent which modulates the group II mGlu receptor is a group II mGlu receptor agonist. In some embodiments, the group II mGlu receptor agonist is LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate), (S)-3C4HPG ((S)-3-carboxy-4-hydroxyphenylglycine); (S)-4C3HPG ((S)-4-carboxy-3-hydroxyphenylglycine); L-CCG-I ((2S,1'S,2'S)-2-(carboxycyclopropyl)glycine); and/or combinations thereof.

In some embodiments, the mGlu receptor is a group III mGlu receptor. In some embodiments, the group III mglu receptor is mGlu7. In some embodiments, the agent which modulates the group III mglu receptor is a group III mglu receptor agonist. In some embodiments, the group III mGlu receptor agonist is ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (N'-bis(diphenylmethyl)-1,2-ethanediamine dihydrochloride); DCG-IV ((2S,2'R,3'R)-2-(2',3'-dicarboxycyclopropyl)glycine); and/or combinations thereof. In some embodiments, the mGlu receptor is mGlu7. In some embodiments, the agonist of mGlu7 is AMN082. In some embodiments, the mGlu receptor modulator is 3,5-Dimethylpyrrole-2,4-dicarboxylic acid 2-propyl ester 4-(1,2,2-trimethyl-propyl) ester (3,5-dimethyl PPP); 3,3'-difluorobenzaldazine (DFB), 3,3'-dimlethoxybenzaldazine (DMeOB), 3,3'-dichlorobenzaldazine (DCB) and other allosteric modulators of mGluR5 disclosed in Mol. Pharmacol. 2003, 64, 731-740; (E)-6-methyl-2-(phenyldiazenyl)pyridin-3-ol (SIB 1757); (E)-2-methyl-6-styrylpyridine (SIB 1893); 2-methyl-6-(phenylethynyl)pyridine (MPEP), 2-methyl-4-((6-methylpyridin-2-yl)ethynyl)thiazole (MTEP); 7-(Hydroxyimino)cyclopropa[b]chromen-1α-carboxylate ethyl ester (CPCCOEt), N-cyclohexyl-3-methylbenzo[d]thiazolo[3,2-a]imidazole-2-carboxamide (YM-298198), tricyclo [3.3.3.1]nonanyl quinoxaline-2-carboxamide (NPS 2390); 6-methoxy-N-(4-methoxyphenyl)quinazolin-4-amine (LY 456239); mGluR1 antagonists disclosed in WO2004/058754 and WO2005/009987; 2-(4-(2,3-dihydro-1H-inden-2-ylamino)-5,6,7,8-tetrahydroquinazolin-2-ylthio)ethanol; 3-(5-(pyridin-2-yl)-2H-tetrazol-2-yl)benzonitrile, 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 6-(3-methoxy-4-(pyridin-2-yl)phenyl)imidazo[2,1-b]thiazole; (S)-(4-fluorophenyl)(3-(3-(4-fluorophenyl)-1,2,4-oxadiazol-5-yl)piperidin-1-yl)methanone (ADX47273) and/or combinations thereof.

In some embodiments, a glutamate receptor modulator is a nootropic agent. Contemplated for use with the formulations disclosed herein are nootropic agents that modulate neuronal signalling by activating glutamate receptors. In some instances, nootropic agents treat or ameliorate hearing loss (e.g., NIHL) or tinnitus. Accordingly, some embodiments incorporate the use of nootropic agents including, and not limited to, piracetam, Oxiracetam, Aniracetam, Pramiracetam, Phenylpiracetam (Carphedon), Etiracetam, Levetiracetam, Nefiracetam, Nicoracetam, Rolziracetam, Nebracetam, Fasoracetam, Coluracetam, Dimiracetam, Brivaracetam, Seletracetam, and/or Rolipram for the treatment of NIHL or tinnitus.

Trophic Agents

Contemplated for use with the formulations disclosed herein are agents that reduce or delay the degeneration of neurons and/or hair cells of the auris. In some embodiments, contemplated for use with the compositions described herein are agents that are trophic agents, e.g., agents that promote the growth of tissue and/or neurons and/or hair cells of the auris. Also contemplated for use with the compositions described herein are agents for treating or ameliorating hearing loss or reduction resulting from destroyed, stunted, malfunctioning, damaged, fragile or missing hairs in the inner ear. Accordingly, some embodiments incorporate the use of trophic agents which promote the survival of neurons and otic hair cells, and/or the growth of neurons and otic hair cells. In some embodiments, the trophic agent which promotes the survival of otic hair cells is a growth factor. In some embodiments, the growth factor is a neurotroph. In certain instances, neurotrophs are growth factors which prevent cell death, prevent cell damage, repair damaged neurons and otic hair cells, and/or induce differentiation in progenitor cells. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, and/or combinations thereof. In some embodiments, the growth factor is a fibroblast growth factor (FGF), an insulin-like growth factor (IGF), an epidermal growth factor (EGF), a platelet-derived growth factor (PGF) and/or agonists thereof. In some embodiments, the growth factor is an agonist of the fibroblast growth factor (FGF) receptor, the insulin-like growth factor (IGF) receptor, the epidermal growth factor (EGF) receptor, and/or the platlet-derived growth factor. In some embodiments, the growth factor is hepatocyte growth factor.

In some embodiments, the trophic agent and/or neurotroph is BDNF. In some embodiments, the trophic agent and/or neurotroph is GDNF. In certain instances, BDNF and GDNF are neurotrophs that promote the survival of existing neurons (e.g. spiral ganglion neurons), and otic hair cells by repairing damaged cells, inhibiting the production of ROS, and/or inhibiting cell death. In certain instances, it also promotes the differentiation of neural and otic hair cell progenitors. Further, in certain instances, it protects the Cranial Nerve VII from degeneration. In some embodiments, BDNF is administered in conjunction with fibroblast growth factor.

In some embodiments, the neurotroph is neurotrophin-3. In certain instances, neurotrophin-3 promotes the survival of existing neurons and otic hair cells, and promotes the differentiation of neural and otic hair cell progenitors. Further, In certain instances, it protects the VII nerve from degeneration.

some embodiments, the neurotroph is CNTF. In certain instances, CNTF promotes the synthesis of neurotransmitters and the growth of neuritis. In some embodiments, CNTF is administered in conjunction with BDNF.

In some embodiments, the trophic agent and/or neurotroph is GDNF. In certain instances, GDNF expression is increased by treatment with ototoxic agents. Further, in certain instances, cells treated with exogenous GDNF have higher survival rates after trauma than untreated cells.

In some embodiments, the trophic agent and/or growth factor is an epidermal growth factor (EGF). In some embodiments, the EGF is heregulin (HRG). In certain instances, HRG stimulates the proliferation of utricular sensory epithelium. In certain instances, HRG-binding receptors are found in the vestibular and auditory sensory epithelium.

In some embodiments, the trophic agent and/or growth factor is an insulin-like growth factor (IGF). In some embodiments, the IGF is IGF-1. In some embodiments, the IGF-1 is mecasermin. In certain instances, IGF-1 attenuates the damage induced by exposure to an aminoglycoside. In certain instances, IGF-1 stimulates the differentiation and/or maturation of cochlear ganglion cells.

In some embodiments, the FGF receptor agonist is FGF-2. In some embodiments, the IGF receptor agonist is IGF-1. Both the FGF and IGF receptors are found in the cells comprising the utricle epithelium.

In some embodiments, the growth factor is hepatocyte growth factor (HGF). In some instances, HGF protects cochlear hair cells from noise-induced damage and reduces noise-exposure-caused ABR threshold shifts.

Also contemplated for use in the otic formulations described herein are growth factors including Erythropoietin (EPO), Granulocyte-colony stimulating factor (G-CSF), Granulocyte-macrophage colony stimulating factor (GM-CSF), Growth differentiation factor-9 (GDF9), Insulin-like growth factor (IGF), Myostatin (GDF-8), Platelet-derived growth factor (PDGF), Thrombopoietin (TPO), Transforming growth factor alpha (TGF-α), Transforming growth factor beta (TGF-β), Vascular endothelial growth factor (VEGF) or combinations thereof. Also contemplated for use in the otic compositions described herein are trophic factors including antioxidants and/or vitamins that are described herein.

Anti-Intercellular Adhesion Molecule-1 Antibody

Contemplated for use with the formulations disclosed herein are antibodies to anti-intercellular adhesion molecule (ICAM). In some instances, ICAM blocks the cascade of reactive oxygen species associated with exposure to noise. In some instances modulation of the cascade of reactive oxygen species associated with exposure to noise ameliorates or reduces the degeneration of neurons and/or hair cells of the auris. Accordingly, some embodiments incorporate the use of agents that are antibodies to ICAMs (e.g., anti-ICAM-1 Ab, anti-ICAM-2 Ab or the like).

Otoprotectants

Contemplated for use with the formulations disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of otoprotectants. In some embodiments, an otoprotectant is a glutamate receptor antagonist as described herein. In some embodiments, an otoprotectant is a corticosteroid as described herein. In some embodiments, otoprotectants are agents that modulate glutathione peroxidase (GPx). The enzyme GPx reduces reactive oxygen species (ROS) in the cohclea and maintains the health of neurons and/or hair cells in the inner ear. Modulators of GPx include and are not limited to glutathione peroxidase mimics such as 2-phenyl-1,2-benzoisoselenazol-3 (2H)-one (ebselen, SPI-1005), 6A,6B-diseleninic acid-6A',6B'-selenium bridged β-cyclodextrin (6-diSeCD), and 2,2'-diseleno-bis-β-cyclodextrin (2-diSeCD).

In some embodiments, the use of otoprotectants reduces or ameliorates hearing loss or reduction in hearing resulting from destroyed, stunted, malfunctioning, damaged, fragile or missing hairs in the inner ear. Otoprotectants include, but are not limited to, D-methionine, L-methionine, ethionine, hydroxyl methionine, methioninol, amifostine, mesna (sodium 2-sulfanylethanesulfonate), a mixture of D and L methionine, N-acetyl methionine (NAM), normethionine, homomethionine, S-adenosyl-L-methionine, diethyldithiocarbamate, ebselen (2-phenyl-1,2-benzisoselenazol-3(2H)-one), sodium thiosulfate, AM-111 (a cell permeable JNK inhibitor, (Laboratories Auris SAS)), N-acetyl-DL-methionine, S-adenosylmethionine, cysteine, homocysteine, cysteamine, N-acetylcysteine (NAC), glutathione, glutathione ethylester, glutathione diethylester, glutathione triethylester, cysteamine, cystathione, N,N'-diacetyl-L-cystine (DiNAC), 2(R,S)-D-ribo-(1',2',3',4'-tetrahydroxybutyl)-thiazolidine-4 (R)-carboxylic acid (RibCys), 2-alkylthiazolidine 2(R,S)-D-ribo-(1',2',3',4'-tetrahydroxybutyl)thiazolidine (RibCyst), and 2-oxo-L-thiazolidine-4-carboxylic acid (OTCA), salicylic acid, leucovorin, leucovorin calcium, dexrazoxane, piracetam, Oxiracetam, Aniracetam, Pramiracetam, Phenylpiracetam (Carphedon), Etiracetam, Levetiracetam, Nefiracetam, Nicoracetam, Rolziracetam, Nebracetam, Fasoracetam, Coluracetam, Dimiracetam, Brivaracetam, Seletracetam, Rolipramand or combinations thereof.

In some embodiments, otoprotectants include xanthine oxidase inhibitors. Non-limiting examples of xanthine odixase inhibitors include allopurinol; 1-methylallopurinol; 2-methylallopurinol; 5-methylallopurinol; 7-methylallopurinol; 1,5-dimethylallopurinol; 2,5-dimethylallopurinol; 1,7-dimethylallopurinol; 2,7-dimethylallopurinol; 5,7-dimethylallopurinol; 2,5,7-trimethylallopurinol; 1-ethoxycarbonylallopurinol; and 1-ethoxycarbonyl-5-methylallopurinol.

In some embodiments, otoprotectants are used in combination with toxicants.

Modulators of Hair Cell Regeneration

Contemplated for use with the formulations disclosed herein are agents that modulate the regeneration of neurons and/or hair cells of the auris, and agents for treating or ameliorating hearing loss or reduction resulting from destroyed, stunted, malfunctioning, damaged, fragile or missing hairs in the inner ear. In some embodiments, an auris sensory cell modulator allows for proliferation and/or regeneration of auris hair cells and/or supporting cells. Accordingly, some embodiments incorporate the use of cyclin-dependent kinase (CDK) modulators. In some embodiments, CDK modulators are p27Kip1 modulators. p27Kip1 mediates sensory hair cell regeneration in the organ of Corti. In some instances, sensory hair cells (e.g., short hair cells) of the inner ear are regenerated by stimulation of proliferation of supporting cells (e.g. Hansen's cells, Deiter's cells and/or Pillar's cells or the like). In some instances modulators of the cyclin-dependent kinase p27Kip1 are antisense molecules (e.g., siRNA molecules) or peptide molecules (e.g., endogenous ligands for p27Kip1) that modulate the activity of p27Kip1.

In some embodiments, a formulation described herein comprises a nucleic acid and/or transcription factor (e.g., POU4F1, POU4F2, POU4F3, Brn3a, Brn3b and/or Brn3c or the like) capable of stimulating the formation of inner ear sensory hair cells or inner ear support cells. Non-limiting examples of such nucleic acid molecules and/or transcription factors include and are not limited to molecules described in US Appl. Pub. Nos. 20070041957 and 20030203482, which disclosure described therein is incorporated herein by reference.

Immune System Cells

Contemplated for use with the formulations disclosed herein are agents that reduce, reverse or delay the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of cells which participate in the repair of otic hair cells and neurons. In some embodiments, the cells which participate in the repair of otic hair cells and neurons are macrophages, microglia, and/or microglia-like cells. In certain instances, the concentration of macrophages and microglia increase in ears damaged by treatment with ototoxic agents. In certain instances, microglia-like cells eliminate waste from ototoxic antibiotic neomycin.

Ototoxic Agents and Toxicants

Contemplated for use with the formulations disclosed herein are agents that destroy neurons and/or otic hair cells. Accordingly, some embodiments incorporate the use of agents which fatally damage and/or induce death in the neurons and/or otic hair cells of the auris. In some embodiments, death of auris sensory cells (e.g., hair cells) treats symptoms (e.g., vertigo) associated with any otic disease or condition described herein. In some embodiments, toxicants induce chemical lesions in the ear that alleviate symptoms such as, by way of example, vertigo. In some embodiments, the agents which fatally damage and/or induce death in the neurons and/or otic hair cells of the auris are the aminoglycoside antibiotics (e.g. gentamicin, and amikacin), the macrolide antibiotics (e.g. erythromycin), the glycopeptide antibiotics (e.g. vancomycin), the loop diuretics (e.g. furosemide), nicotine, 6-hydroxy dopamine (6-OH DPAT), 6,7-dinitroquinoxaline-2,3-dione (DNQX) or the like. In some embodiments, a composition described herein comprises a toxicant that is used to treat vertigo by selectively destroying hair cells in the ear. In some of such embodiments, an otic composition comprising a toxicant is advantageous; such a composition provides therapeutic benefit for treatment of vertigo because it is administered non-systemically to the ear and does not cause side effects associated with systemic administration of a toxicant.

In some embodiments, a composition described herein is useful in pre-clinical animal studies (e.g., animal guinea pig model studies). In some instances, a composition described herein comprising a toxicant is used for induction of chemical lesions in the ear of an animal. In some instances, such an animal is used for testing therapeutic efficacy of compositions described herein in animal models.

Retinoblastoma Protein Modulation

Contemplated for use with the formulations disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Further contemplated herein are agents that destroy neurons and/or otic hair cells. Accordingly, some embodiments incorporate the use of agents that modulate retinoblastoma protein (pRB). pRB is a member of the pocket protein family. It is encoded by the RB1 gene. In certain instances, it inhibits transition from G1 to S phase by binding to and inactivating the E2f family of transcription factors. In certain instances, it also regulates differentiation, and survival of hair cells. In certain instances, pRB knock-out mice demonstrate increased proliferation of hair cells.

In some embodiments, the agent that modulates one or more of the pRB is an agonist of pRB. In some embodiments, the agent that modulates one or more of the pRB is an antagonist of pRB. In certain instances, a compound which agonizes or antagonizes pRB is identified (e.g. by use of a high throughput screen). In some embodiments, a construct is designed such that a reporter gene is placed downstream of an E2F binding sequence. In some embodiments, the binding sequence is TTTCGCGC. In some embodiments, the reporter gene is luciferase, CAT, GFP, β-lactamase or β-galactosidase. In certain instances, E2f binds to the binding sequence causing the transcription and expression of the reporter gene. In certain instances, an agonist of pRB causes an increase in the binding of pRB to E2f. In certain instances, the increase in binding of pRB and E2f results in a decrease in the transcription and expression of the reporter gene. In certain instances, an antagonist of pRB causes a decrease in the binding of pRB to E2f. In certain instances, the decrease in binding of pRB and E2f results in a increase in the transcription and expression of the reporter gene.

In some embodiments, the agent that modulates pRB is an siRNA molecule. In certain instances, the siRNA molecule inhibits the transcription of an RB1 gene by RNA interference (RNAi). In some embodiments, a double stranded RNA (dsRNA) molecule with sequences complementary to an RB1 mRNA sequence is generated (e.g. by PCR). In some embodiments, a 20-25 bp siRNA molecule with sequences complementary to an RB1 mRNA is generated. In some embodiments, the 20-25 bp siRNA molecule has 2-5 bp overhangs on the 3' end of each strand, and a 5' phosphate terminus and a 3' hydroxyl terminus. In some embodiments, the 20-25 bp siRNA molecule has blunt ends. For techniques for generating RNA sequences see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, the dsRNA or siRNA molecule is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

In certain instances, after administration of the dsRNA or siRNA molecule, cells at the site of administration (e.g. the cells of cochlea, organ of Corti, and/or the vestibular labyrinth) are transformed with the dsRNA or siRNA molecule. In certain instances following transformation, the dsRNA molecule is cleaved into multiple fragments of about 20-25 bp to yield siRNA molecules. In certain instances, the fragments have about 2 bp overhangs on the 3' end of each strand.

In certain instances, an siRNA molecule is divided into two strands (the guide strand and the anti-guide strand) by an RNA-induced Silencing Complex (RISC). In certain instances, the guide strand is incorporated into the catalytic component of the RISC (i.e. argonaute). In certain instances, the guide strand binds to a complementary RB1 mRNA sequence. In certain instances, the RISC cleaves the RB1 mRNA. In certain instances, the expression of the RB1 gene is down-regulated.

In some embodiments, a sequence complementary to RB1 mRNA is incorporated into a vector. In some embodiments, the sequence is placed between two promoters. In some embodiments, the promoters are orientated in opposite directions. In some embodiments, the vector is contacted with a cell. In certain instances, a cell is transformed with the vector. In certain instances following transformation, sense and anti-sense strands of the sequence are generated. In certain instances, the sense and anti-sense strands hybridize to form a dsRNA molecule which is cleaved into siRNA molecules. In certain instances, the strands hybridize to form an siRNA molecule. In some embodiments, the vector is a plasmid (e.g. pSUPER; pSUPER.neo; pSUPER.neo+gfp).

In some embodiments, the vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

Thyroid Hormone Receptor Modulation

Contemplated for use with the formulations disclosed herein are agents that reduce or reverse the degeneration of neurons and/or hair cells of the auris, and/or promote the growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents that modulate Thyroid Hormone (TH) receptors. The TH receptors are a family of nuclear hormone receptors. The family includes, but is not limited to TRα1 and TRβ. In certain instances, TRβ knockout mice demonstrate a decreased responsiveness to auditory stimuli, and a decrease in K+ current in hair cells.

In some embodiments, the agent that modulates one or more of the TH receptors is an agonist of the one or more TH receptors. In some embodiments, the agonist of one or more of the TH receptors is T3 (3,5,3'-triiodo-L-thyronine); KB-141 (3,5-dichloro-4-(4-hydroxy-3-isopropylphenoxy) phenylacetic acid); GC-1 (3,5-dimethyl-4-(4'-hydroxy-3'-isopropylbenzyl)-phenoxy acetic acid); GC-24 (3,5-dimethyl-4-(4'-hydroxy-3'-benzyl)benzylphenoxyacetic acid); sobetirome (QRX-431); 4-OH-PCB106 (4-OH-2',3,3',4',5'-pentachlorobiphenyl); MB07811 ((2R,4S)-4-(3-chlorophenyl)-2-[(3,5-dimethyl-4-(4-hydroxy-3-isopropylbenzyl)phenoxy)methyl]-2-oxido-[1,3,2]-dioxaphosphonane); MB07344 (3,5-dimethyl-4-(4-hydroxy-3-isopropylbenzyl) phenoxy)methylphosphonic acid); and combinations thereof. In certain instances, KB-141; GC-1; sobetirome; and GC-24 are selective for TRβ.

TRPV Modulation

Contemplated for use with the formulations disclosed herein are agents that modulate the degeneration of neurons and hair cells, and agents for treating or ameliorating hearing loss or reduction resulting from destroyed, stunted, malfunctioning, damaged, fragile or missing hairs in the inner ear. Accordingly, some embodiments incorporate the use of agents that modulate TRPV receptors. The TRPV (Transient Receptor Potential Channel Vanilloid) receptors are a family of non-selective ion channels permeable to calcium, amongst other ions. There are six members of the family: TRPV1-6. In certain instances, following treatment with kanamycin, TRPV 1 is upregulated. Additionally, in certain instances, antagonism of the TRPV 4 receptor makes mice vulnerable to acoustic trauma. Further, in certain instances, capsaicin, an agonist of TRPV 1, prevents hyperlocomotion following an ischemic event.

In some embodiments, the agent that modulates one or more of the TRPV receptors is an agonist of the one or more TRPV receptors. In some embodiments, the agonist of one or more of the TRPV receptors is capsaicin, resiniferatoxin, or combinations thereof. In some embodiments, administration of an auris sensory cell modulating composition comprising a TRPV agonist reduces or reverses degeneration of neurons and hair cells.

Sodium Channel Blockers

Contemplated for use with the formulations disclosed herein are agents that modulate the degeneration of neurons and hair cells, and agents for treating or ameliorating hearing loss or reduction resulting from destroyed, stunted, malfunctioning, damaged, fragile or missing hairs in the inner ear. In certain instances, excitotoxicity causes the excessive opening of Na+ channels. In certain instances, this results in excess Na+ ions entering the neuron. In certain instances, the excess influx of Na+ ions into the neuron causes the neuron to fire more often. In certain instances, this increased firing yields a rapid buildup of free radicals and inflammatory compounds. In certain instances, the free radicals damage the mitochondria, depleting the cell's energy stores. Further, in certain instances, excess levels of Na+ ions activate excess levels of enzymes including, but not limited to, phospholipases, endonucleases, and proteases. In certain instances, the over-activation of these enzymes results in damage to the cytoskeleton, plasma membrane, mitochondria, and DNA of the neuron. Accordingly, some embodiments incorporate the use of agents which antagonize the opening of Na+ channels and reduce or reverse auris hair cell death and/or auris hair cell damage.

In some embodiments, the Na+ channel blocker is vinpocetine ((3a,16a)-Eburnamenine-14-carboxylic acid ethyl ester); sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarbox amide hydrochloride); carbamazepine (5H-dibenzo[b,f] azepine-5-carboxamide); TTX (octahydro-12-(hydroxymethyl)-2-imino-5,9:7,10a-dimethano-10aH-[1,3]dioxocino [6,5-d]pyrimidine-4,7,10,11,12-pentol); RS100642 (1-(2,6-dimethyl-phenoxy)-2-ethylaminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenytoin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl) pyrimidine-2,4-1.1 ethanesulphonate); QX-222 (2-[(2,6-dimethylphenyl)amino]-N,N,N-trimethyl-2-oxoethaniminium chloride); ambroxol (trans-4-[[(2-Amino-3,5-dibromophenyl)methyl]amino]cyclo hexanol hydrochloride); R56865 (N-[1-(4-(4-fluorophenoxy)butyl]-4-piperidinyl-N-methyl-2-benzo-thiazolamine); lubeluzole; ajmaline ((17R,21 alpha)-ajmalan-17,21-diol); procainamide (4-amino-N-(2-diethylaminoethyl)benzamide hydrochloride); flecainide; riluzoleor; or combinations thereof.

Corticosteroids

Contemplated for use with the compositions and formulations disclosed herein are agents that reduce, reverse or delay the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which protect otic hair cells from ototoxins. In some embodiments, the agent which protects otic hair cells from ototoxins is a steroid. In some embodiments, the steroid which protects otic hair cells from ototoxins is a corticosteroid. In some embodiments, the corticosteroid is triamicinolone actenoide and/or dexamethasone. In certain instances, triamicinolone actenoide and dexamethasone protect otic hair cells from damage caused by the naturally occurring toxin 4-hydroxy-2,3-nonenal (HNE), which is produced in the inner ear in response to oxidative stress. Other corticosteroids include, and are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, or triamcinolone hexacetonide, or phosphate prodrug or ester prodrug thereof.

Stem Cells and Differentiated Auris Sensory Cells

Contemplated for use with the formulations disclosed herein are transplants of cells that supplement and/or replace the pre-existing neurons and/or hair cells of the auris. In some embodiments, the agent is a stem cell. In some embodiments, the agent is a partially or fully differentiated auris sensory cell. In some embodiments, the differentiated auris sensory cell is derived from a human donor. In some embodiments, the differentiated auris sensory cell is derived from a stem cell, the differentiation of which was induced under artificial (e.g. laboratory) conditions.

Stem cells are cells that possess the capacity to differentiate into multiple cell types. Totipotent stem cells can differentiate into embryonic cells or extraembryonic cells. Pluripotent cells can differentiate into cells of any of endoderm, mesoderm, or ectoderm origin. Multipotent cells can differentiate into closely related cells (e.g. hematopoietic stem cells). Unipotent cells can differentiate into only one type of cell, but like other stem cells have the characteristic of self-renewal. In some embodiments, the stem cell is totipotent, pluripotent, multipotent, or unipotent. Further, stem cells can undergo mitotic division without themselves differentiating (i.e. self-renewal).

Embryonic stem (ES) cells are stem cells derived from the epiblast tissue of the inner cell mass of a blastocyst or earlier stage embryo. ES cells are pluripotent. In some embodiments, the stem cell is an ES cell. Adult stem cells (also known as somatic cells or germline cells) are cells isolated from a developed organism wherein the cells possess the characteristic of self-renewal, and the ability to differentiate into multiple cell types. Adult stem cells are pluripotent (for example, stem cells found in umbilical cord blood), multipotent or unipotent. In some embodiments, the stem cell is an adult stem cell.

In some embodiments, a stem cell and/or a differentiated auris sensory cell is administered in combination with a differentiation stimulating agent. In some embodiments, the differentiation stimulating agent is a growth factor. In some embodiments, the growth factor is a neurotrophin (e.g. nerve growth factor (NGF), brain-derived neurotrophic factor (BDNF), neurotrophin-3 (NT-3), neurotrophin-4 (NT-4), or novel neurotrophin-1 (NNT1). In some embodiments, the growth factor is FGF, EGF, IGF, PGF, or combinations thereof.

In some embodiments, a stem cell and/or a differentiated auris sensory cell is administered to a subject in need thereof as a controlled release agent. In some embodiments, a stem cell and/or a differentiated auris sensory cell is administered to a subject in need thereof as an immediate release agent (e.g. in a cell suspension) in combination with a controlled release auris sensory cell modulating agent. In some embodiments, a controlled release auris sensory cell modulating agent is a vector comprising an Atoh1 or BRN3 gene, an siRNA sequence targeting RB1, a growth factor, or combinations thereof.

In some embodiments, a stem cell and/or a differentiated auris sensory cell is administered to the cochlea or vestibular labyrinth. In some embodiments, a stem cell and/or a differentiated auris sensory cell is administered by via intratympanic injection, and/or a post-auricular incision. In some embodiments, a stem cell and/or a differentiated auris sensory cell is contacted with the organ of Corti, vestibulocochlear nerve, and/or crista ampullaris.

Immediate Release Agents

In some embodiments, the composition further comprises a modulator of neuron and/or hair cells of the auris as an immediate release agent wherein the immediate release modulator of neuron and/or hair cells of the auris is the same agent as the controlled-release agent, a different modulator of neuron and/or hair cells of the auris, an additional therapeutic agent, or a combination thereof. In some embodiments, the immediate release agent is a stem cell, a differentiated auris sensory cell, an immune system cell, a vector carrying a copy of an Atoh1 gene, a vector carrying a copy of a BRN3 gene, an siRNA sequence, an miRNA sequence, or combinations thereof.

Direct Injection

In some embodiments, one of the agents is directly injected into the auris interna, including through the round window membrane, while a second agent is administered in the auris media, on or in contact with the round window membrane such that the second agent is in the form of a controlled release formulation. In one embodiment, the directly-administered agent is a stem cell, a differentiated auris sensory cell, an immune system cell, a vector carrying a copy of an Atoh1 gene, a vector carrying a copy of a BRN3 gene, an siRNA sequence, an miRNA sequence, or combinations thereof.

Concentration of Active Agent

In some embodiments, the compositions described herein have a concentration of active pharmaceutical ingredient between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the active ingredient, or pharmaceutically acceptable prodrug or salt thereof, by weight of the composition. In some embodiments, the compositions described herein have a concentration of active pharmaceutical agent between about 1% to about 50%, between about 5% to about 50%, between about 10% to about 40%, or between about 10% to about 30%, of the active ingredient, or pharmaceutically acceptable prodrug or salt thereof, by weight of the composition. In some embodiments, formulations described herein comprise about 70% by weight of an auris sensory cell modulating agent by weight of the formulation. In some embodiments, formulations described herein comprise about 60% by weight of an auris sensory cell modulating agent by weight of the formulation. In some embodiments, formulations described herein comprise about 50% by weight of an auris sensory cell modulating agent by weight of the formulation. In some embodiments, formulations described herein comprise about 40% by weight of an auris sensory cell modulating agent by weight of the formulation. In some embodiments, formulations described herein comprise about 30% by weight of an auris sensory cell modulating agent by weight of the formulation. In some embodiments, formulations described herein comprise about 20% by weight of an auris sensory cell modulating agent by weight of the formulation. In some embodiments, formulations described herein comprise about 15% by weight of an auris sensory cell modulating agent, or pharmaceutically acceptable prodrug or salt thereof, by weight of the formulation. In some embodiments, formulations described herein comprise about 10% by weight of an auris sensory cell modulating agent by weight of the formulation. In some embodiments, formulations described herein comprise about 5% by weight of an auris sensory cell modulating agent, or pharmaceutically acceptable prodrug or salt thereof, by weight of the formulation. In some embodiments, formulations described herein comprise about 2.5% by weight of an auris sensory cell modulating agent, or pharmaceutically acceptable prodrug or salt thereof, by weight of the formulation. In some embodiments, formulations described herein comprise about 1% by weight of an auris sensory cell modulating agent, or pharmaceutically acceptable prodrug or salt thereof, by weight of the formulation. In some embodiments, formulations described herein comprise about 0.5% by weight of an auris sensory cell modulating agent, or pharmaceutically acceptable prodrug or salt thereof, by weight of the formulation. In some embodiments, formulations described herein comprise about 0.1% by weight of an auris sensory cell modulating agent, or pharmaceutically acceptable prodrug or salt thereof, by weight of the formulation. In some embodiments, formulations described herein comprise about 0.01% by weight of an auris sensory cell modulating agent, or pharmaceutically acceptable prodrug or salt thereof, by weight of the formulation. In some embodiments, the formulations described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the formulation.

Combination Therapy

In some embodiments, any composition or device described herein comprises one or more active agents and/or a second therapeutic agent including but not limited to antiemetic agents, antimicrobial agents, antioxidants, anti-septic agents or the like.

Anti-Emetic Agents

Anti-Emetic agents are optionally used in combination with the formulations disclosed herein. Anti-emetic agents include promethazine, prochlorperazine, trimethobenzamide, and triethylperazine. Other anti-emetic agents include 5HT3 antagonists such as dolasetron, granisetron, ondansetron, tropisetron, and palonosetron; and neuroleptics such as droperidol. Further anti-emetic agents include antihistamines, such as meclizine; phenothiazines such as perphenazine, and thiethylperazine; dopamine antagonists, including domperidone, properidol, haloperidol, chlorpromazine, promethazine, prochlorperazine, metoclopramide and combinations thereof; cannabinoids, including dronabinol, nabilone, sativex, and combinations thereof; anticholinergics, including scopolamine; and steroids, including dexamethasone; trimethobenzamine, emetrol, propofol, muscimol, and combinations thereof.

Antimicrobial Agents

Antimicrobial agents are also contemplated as useful with the formulations disclosed herein. Antimicrobial agents include agents that act to inhibit or eradicate microbes, including bacteria, fungi or parasites. Specific antimicrobial agents may be used to combat specific microbes. Accordingly, a skilled practitioner would know which antimicrobial agent would be relevant or useful depending on the microbe identified, or the symptoms displayed. Antimicrobial agents include antibiotics, antiviral agents, antifungal agents, and antiparasitic agents.

Antibiotics may include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

Antiviral agents may include acyclovir, famciclovir and valacyclovir. Other antiviral agents include abacavir, aciclovir, adfovir, amantadine, amprenavir, arbidol., atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents may include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, and combinations thereof. Antiparasitic agents may include amitraz, amoscanate, avermectin, carbadox, diethylcarbamizine, dimetridazole, diminazene, ivermectin, macrofilaricide, malathion, mitaban, oxaminiquine, permethrin, praziquantel, prantel pamoate, selamectin, sodium stibogluconate, thiabendazole, and combinations thereof.

Antioxidants

Antioxidants are optionally used in combination with the compositions described herein. Antioxidants are also contemplated as being useful with the formulations disclosed herein as agents that modulate the degeneration of neurons and/or hair cells of the auris. Accordingly, some embodiments incorporate the use of antioxidants. In some embodiments, the antioxidant is vitamin C, N-acetylcysteine, vitamin E, Ebselen (2-phenyl-1,2-benzisoselenazol-3(2H)-one (also called PZ 51 or DR3305), L-methionine, Idebenone (2-(10-hydroxydecyl)-5,6-dimethoxy-3-methyl-cyclohexa-2,5-diene-1,4-dione). In some embodiments, antioxidants are trophic agents and promote growth of healthy cells.

Anti-Septic Agents

Anti-septic agents are optionally used in combination with the compositions described herein. Anti-septic agents are also contemplated as useful with the formulations disclosed herein. Anti-septic agents include, but are not limited to, acetic acid, boric acid, gentian violet, hydrogen peroxide, carbamide peroxide, chlorhexidine, saline, mercurochrome, povidone iodine, polyhyroxine iodine, cresylate and aluminum acetate, and mixtures thereof.

Other agents are optionally used in any composition or device described herein. In some embodiments, a monoamine oxidase inhibitor (e.g., Rasagiline, R(+)—N-propargyl-1-aminoindan) is used in any composition or device described herein. In some embodiments, an adenosine antagonist (e.g., R—N6-Phenylisopropyl adenosine, 1-2-oxothiazolidine-4-carboxylic acid (Procysteine)) is used in any composition or device described herein. Any combination of active agents and/or second therapeutic agent is compatible with the compositions described herein.

Otic Surgery and Implants

In some embodiments, the pharmaceutical formulations, compositions or devices described herein are used in combination with (e.g., implantation, short-term use, long-term use, or removal of) implants (e.g., cochlear implants). As used herein, implants include auris-interna or auris-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. In some instances, the implants are used in conjunction with a patient experiencing hearing loss. In some instances, the hearing loss is present at birth. In some instances, the hearing loss is associated with conditions such as AIED, bacterial meningitis or the like that lead to osteoneogenesis and/or nerve damage with rapid obliteration of cochlear structures and profound hearing loss.

In some instances, an implant is an immune cell or a stem cell transplant in the ear. In some instances, an implant is a small electronic device that has an external portion placed behind the ear, and a second portion that is surgically placed under the skin that helps provide a sense of sound to a person who is profoundly deaf or severely hard-of-hearing. By way of example, such cochlear medical device implants bypass damaged portions of the ear and directly stimulate the auditory nerve. In some instances cochlear implants are used in single sided deafness. In some instances cochlear implants are used for deafness in both ears.

In some embodiments, administration of an auris sensory cell modulator composition or device described herein in combination with an otic intervention (e.g., an intratympanic injection, a stapedectomy, a medical device implant or a cell-based transplant) delays or prevents collateral damage to auris structures, e.g., irritation, cell damage, cell death, osteoneogenesis and/or further neuronal degeneration, caused by the external otic intervention (e.g., installation of an external device and/or cells in the ear). In some embodiments, administration of an auris sensory cell modulator composition or device described herein in combination with an implant allows for a more effective restoration of hearing loss compared to an implant alone.

In some embodiments, administration of an auris sensory cell modulator composition or device described herein reduces damage to cochlear structures caused by underlying conditions (e.g., bacterial meningitis, autoimmune ear disease (AIED)) allowing for successful cochlear device implantation. In some embodiments, administration of a composition or device described herein, in conjunction with otic surgery, medical device implantation and/or cell transplantation, reduces or prevents cell damage and/or death (e.g., auris sensory hair cell death and/or damage) associated with otic surgery, medical device implantation and/or cell transplantation.

In some embodiments, administration of an auris sensory cell modulator composition or device described herein (e.g., a composition or device comprising a growth factor) in conjunction with a cochlear implant or stem cell transplant has a trophic effect (e.g., promotes healthy growth of cells and/or healing of tissue in the area of an implant or transplant). In some embodiments, a trophic effect is desirable during otic surgery or during intratympanic injection procedures. In some embodiments, a trophic effect is desirable after installation of a medical device or after a cell transplant. In some of such embodiments, the auris sensory cell modulator compositions or devices described herein are administered via direct cochlear injection, through a chochleostomy or via deposition on the round window.

In some embodiments, administration of an anti-inflammatory or immunosuppressant composition (e.g., a composition comprising an immunosuppressant such as a corticosteroid) reduces inflammation and/or infections associated with otic surgery, implantation of a medical device or a cell transplant. In some instances, perfusion of a surgical area with an auris sensory cell modulator formulation described herein reduces or eliminates post-surgical and/or post-implantation complications (e.g., inflammation, hair cell damage, neuronal degeneration, osteoneogenesis or the like). In some instances, perfusion of a surgical area with a formulation described herein reduces post-surgery or post-implantation recuperation time. In some embodiments, a medical device is coated with a composition described herein prior to implantation in the ear.

In one aspect, the formulations described herein, and modes of administration thereof, are applicable to methods of direct perfusion of the inner ear compartments. Thus, the formulations described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, endolymphatic sacculotomy, tympanostomy or the like. In some embodiments, the inner ear compartments are perfused with a formulation described herein prior to otic intervention, during otic intervention, or after otic intervention, or a combination thereof.

In some embodiments, when perfusion is carried out in combination with otic intervention, the auris sensory cell compositions are immediate release compositions. In some of such embodiments, the immediate release formulations described herein are non-thickened compositions and are substantially free of extended release components (e.g., gelling components such as polyoxyethylene-polyoxypropylene copolymers). In some of such embodiments, the compositions contain less than 5% of the extended release components (e.g., gelling components such as polyoxyethylene-polyoxypropylene triblock copolymers) by weight of the formulation. In some of such embodiments, the compositions contain less than 2% of the extended release components (e.g., gelling components such as polyoxyethylene-polyoxypropylene triblock copolymers) by weight of the formulation. In some of such embodiments, the compositions contain less than 1% of the extended release components (e.g., gelling components such as polyoxyethylene-polyoxypropylene triblock copolymers) by weight of the formulation. In some of such embodiments, a composition described herein that is used for perfusion of a surgical area contains substantially no gelling component and is an immediate release composition.

In other embodiments, a composition described herein is administered after an otic intervention (e.g., after implantation of a medical device or a cell-based therapeutic). In some of such embodiments, a composition described herein that is administered after the otic intervention is an intermediate release or extended release composition and contains gelling components as described herein.

Presented below (Table 1) are examples of active agents contemplated for use with the formulations and devices disclosed herein. One or more active agents are used in any of the formulations or devices described herein.

Active Agents (including pharmaceutically acceptable salts of these active agents) for use with the Formulations Disclosed Herein

TABLE 1

| Auris Condition | Therapeutic Agent |
| --- | --- |
| Benign Paroxysmal Positional Vertigo | Diphenhydramine |
| Benign Paroxysmal Positional Vertigo | Lorazepam |
| Benign Paroxysmal Positional Vertigo | Meclizine |
| Benign Paroxysmal Positional Vertigo | Oldansetron |
| Hearing Loss | Estrogen |
| Vertigo | DNQX |
| Vertigo | 6-OH Dopamine |
| Tinnitus | (S)-Ketamine |
| Hearing Loss | Estrogen and progesterone (E + P) |
| Hearing Loss | Folic acid |
| Hearing Loss | Lactated Ringer's with 0.03% Ofloxacin |
| Hearing Loss | Methotrexate |
| Hearing Loss | N-acetyl cysteine |
| Meniere's Disease | Betahistine |
| Meniere's Disease | Sildenafil |
| Meniere's Disease | conivaptan |
| Middle Ear Effusion | Pneumonococcal vaccine |
| Otitis Externa | Diclofenac sodium; dexotc |
| Otitis Externa, Acute | AL-15469A/AL-38905 |
| Otitis Media | Amoxicillin/clavulanate |
| Otitis Media | Dornase alfa |
| Otitis Media | *Echinacea purpurea* |
| Otitis Media | Faropenem medoxomil |
| Otitis Media | Levofloxacin |
| Otitis Media | PNCRM9 |
| Otitis Media | Pneumococcal vaccine |
| Otitis Media | Telithromycin |
| Otitis Media | Zmax |
| Otitis Media with Effusion | Lansoprazole |
| Otitis Media, Acute | AL-15469A; AL-38905 |
| Otitis Media, Acute | Amoxicillin |
| Otitis Media, Acute | Amoxicillin-clavulanate |
| Otitis Media, Acute | Azithromycin |
| Otitis Media, Acute | Azithromycin SR |
| Otitis Media, Acute | Cefdinir |
| Otitis Media, Acute | Hyland's earache drops |
| Otitis Media, Acute | Montelukast |
| Otitis Media, Acute | Pneumonococcal vaccine |
| Otitis Media, Acute with Typanostomy Tubes | AL-15469A/AL38905 |
| Otitis Media, Chronic | Sulfamethoxazole-trimethoprim |
| Otitis Media, Suppurative | Azithromycin |
| Otitis Media, Suppurative | Telithromycin |
| Otosclerosis | Acetylcysteine |
| Ototoxicity | Aspirin |

TABLE 1-continued

| Auris Condition | Therapeutic Agent |
| --- | --- |
| Tinnitus | Acamprosate |
| Tinnitus | Gabapentin |
| Tinnitus | Modafinil |
| Tinnitus | Neramexane |
| Tinnitus | Neramexane mesylate |
| Tinnitus | Piribedil |
| Tinnitus | Vardenafil |
| Tinnitus | Vestipitant + Paroxetine |
| Tinnitus | Vestiplitant |
| Tinnitus | Zinc sulfate |

General Methods of Sterilization

Provided herein are otic compositions that ameliorate or lessen otic disorders described herein. Further provided herein are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U.S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave. In some embodiments, the formulations described herein comprise micronized auris sensory cell modulating agents (e.g., micro-ketamine powder) that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2): 144-50) are amenable to sterilization by filtration through 0.22 µm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size.

In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., ketamine) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma radiation). In some instances, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the formulation. In some instances, sterilization of an auris formulation by filtration through membranes (e.g., 0.2 μM membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The bioburden (e.g., microbial limit) and/or sterility (e.g., endotoxin level) is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP) <71> Sterility Tests (23rd edition, 1995). The rabbit pyrogen test and the *Limulus amebocyte* lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the *Limulus amebocyte* lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

pH and Practical Osmolarity

As used herein, "practical osmolarity" means the osmolarity of a formulation that is measured by including the active agent and all excipients except the gelling and/or the thickening agent (e.g., polyoxyethylene-polyoxypropylene copolymers, carboxymethylcellulose or the like). The practical osmolarity of a formulation described herein is measured by any suitable method, e.g., a freezing point depression method as described in Viegas et. al., *Int. J. Pharm.*, 1998, 160, 157-162. In some instances, the practical osmolarity of a composition described herein is measured by vapor pressure osmometry (e.g., vapor pressure depression method) that allows for determination of the osmolarity of a composition at higher temperatures. In some instances, vapor pressure depression method allows for determination of the osmolarity of a formulation comprising a gelling agent (e.g., a thermoreversible polymer) at a higher temperature wherein the gelling agent is in the form of a gel. The practical osmolality of an otic formulation described herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, the osmolarity at a target site of action (e.g., the perilymph) is about the same as the delivered osmolarity (i.e., osmolarity of materials that cross or penetrate the round window membrane) of any formulation described herein. In some embodiments, the formulations described herein have a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0. In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g., by filtration or aseptic mixing or heat treatment and/or autoclaving (e.g., terminal sterilization) of a gel formulation without degradation of the pharmaceutical agent (e.g., auris sensory cell modulating agent) or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for terminal sterilization (e.g., by heat treatment and/or autoclaving) of a gel formulation without degradation of the pharmaceutical agent (e.g., auris sensory cell modulating agent) or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g., by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g., by filtration or aseptic mixing or heat treatment and/or autoclaving (e.g., terminal sterilization)) of any composition described herein.

In some embodiments, the formulations have a pH as described herein, and include a thickening agent (e.g., a viscosity enhancing agent) such as, by way of non-limiting example, a cellulose based thickening agent described herein. In some instances, the addition of a secondary polymer (e.g., a thickening agent) and a pH of formulation as described herein, allows for sterilization of a formulation described herein without any substantial degradation of the otic agent and/or the polymer components in the otic formulation. In some embodiments, the ratio of a thermoreversible poloxamer to a thickening agent in a formulation that has a pH as described herein, is about 40:1, about 35:1, about 30:1, about 25:1, about 20:1, about 15:1 about 10:1, or about 5:1. For example, in certain embodiments, a sustained and/or extended release formulation described herein comprises a combination of poloxamer 407 (pluronic F127) and carboxymethylcellulose (CMC) in a ratio of about 40:1, about 35:1, about 30:1, about 25:1, about 20:1, about 15:1, about 10:1 or about 5:1.

In some embodiments, the amount of thermoreversible polymer in any formulation described herein is about 10%, about 15%, about 20%, about 25%, about 30%, about 35% or about 40% of the total weight of the formulation. In some embodiments, the amount of thermoreversible polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermoreversible polymer (e.g., pluronic F127) in any formulation described herein is about 7.5% of the total weight of the formulation. In some embodiments, the amount of thermoreversible polymer (e.g., pluronic F127) in any formulation described herein is about 10% of the total weight of the formulation. In some embodiments, the amount of thermoreversible polymer (e.g., pluronic F127) in any formulation described herein is about 11% of the total weight of the formulation. In some embodiments, the amount of thermoreversible polymer (e.g., pluronic F127) in any formulation described herein is about 12% of the total weight of the formulation. In some embodiments, the amount of thermoreversible polymer (e.g., pluronic F127) in any formulation described herein is about 13% of the total weight of the formulation. In some embodiments, the amount of thermoreversible polymer (e.g., pluronic F127) in any formulation described herein is about 14% of the total weight of the formulation. In some embodiments, the amount of thermoreversible polymer (e.g., pluronic F127) in any formulation described herein is about 15% of the total weight of the formulation. In some embodiments, the amount of thermoreversible polymer (e.g., pluronic F127) in any formulation described herein is about 16% of the total weight of the formulation. In some embodiments, the amount of thermoreversible polymer (e.g., pluronic F127) in any formulation described herein is about 17% of the total weight of the formulation. In some embodiments, the amount of thermoreversible polymer (e.g., pluronic F127) in any formulation described herein is about 18% of the total weight of the formulation. In some embodiments, the amount of thermoreversible polymer (e.g., pluronic F127) in any formulation described herein is about 19% of the total weight of the formulation. In some embodiments, the amount of thermoreversible polymer (e.g., pluronic F127) in any formulation described herein is about 20% of the total weight of the formulation. In some embodiments, the amount of thermoreversible polymer (e.g., pluronic F127) in any formulation described herein is about 21% of the total weight of the formulation. In some embodiments, the amount of thermoreversible polymer (e.g., pluronic F127) in any formulation described herein is about 23% of the total weight of the formulation. In some embodiments, the amount of thermoreversible polymer (e.g., pluronic F127) in any formulation described herein is about 25% of the total weight of the formulation.

In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any formulation described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L; and preferably about 270 to about 320 mOsm/L. In specific embodiments, auris compositions described herein are formulated to provide a delivered perilymph-suitable osmolarity at the target site of action of about 250 to about 320 mOsm/kg $H_2O$; or an osmolality of about 270 to about 320 mOsm/kg $H_2O$. In specific embodiments, the deliverable osmolarity/osmolality of the formulations (i.e., the osmolarity/osmolality of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., perilymph) that causes minimal disturbance to the environment of the inner ear and causes minimum discomfort (e.g., vertigo and/or nausea) to a mammal upon administration.

In some embodiments, any formulation described herein is isotonic with the perilymph and/or endolymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the formulations described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and/or practical osmolarity as described herein, and have a concentration of active pharmaceutical ingredient between about 0.01%-about 20%, between about 0.01%-about 10%., between about 0.01%-about 7.5%, between about 0.01%-6%, between about 0.01-5%, between about 0.1-about 10%, or between about 0.1-about 6% of the active ingredient by weight of the formulation. In some embodiments, the formulations described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation. In some embodiments, the formulations described herein have a pH and/or practical osmolarity as described herein, and have a concentration of active pharmaceutical ingredient between about 1 µg/mL and about 500 µg/mL, between about 1 µg/mL and about 250 µg/mL, between about 1 µg and about 100 µg/mL, between about 1

μg/mL and about 50 μg/mL, or between about 1 μg/mL and about 20 μg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e., the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 μm to about 500 μm. In some embodiments, the average diameter of particles in a micronized solid is from about 1 μm to about 200 μm. In some embodiments, the average diameter of particles in a micronized solid is from about 2 μm to about 100 μm. In some embodiments, the average diameter of particles in a micronized solid is from about 3 μm to about 50 μm. In some embodiments, a particulate micronized solid comprises particle sizes of less than about 5 microns, less than about 20 microns and/or less than about 100 microns. In some embodiments, the use of particulates (e.g., micronized particles) of auris sensory cell modulating agent allows for extended and/or sustained release of the auris sensory cell modulating agent from any formulation described herein compared to a formulation comprising non-multiparticulate (e.g., non-micronized) auris sensory cell modulating agent. In some instances, formulations containing multiparticulate (e.g. micronized) auris sensory cell modulating agent are ejected from a 1 mL syringe adapted with a 27 G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

In some embodiments, a formulation described herein comprises one or more auris sensory cell modulating agents wherein the auris sensory cell modulating agent comprises nanoparticulates. In some embodiments, a formulation described herein comprises auris sensory cell modulating agent beads (e.g., dextromethorphan beads) that are optionally coated with controlled release excipients. In some embodiments, a formulation described herein comprises an auris sensory cell modulating agent that is granulated and/or reduced in size and coated with controlled release excipients; the granulated coated auris sensory cell modulating agent particulates are then optionally micronized and/or formulated in any of the compositions described herein.

In some instances, a combination of an auris sensory cell modulating agent as a neutral molecule, free acid or free base and a salt of the auris sensory cell modulating agent is used to prepare pulsed release otic agent formulations using the procedures described herein. In some formulations, a combination of a micronized auris sensory cell modulating agent (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the auris sensory cell modulating agent (e.g., micronized auris sensory cell modulating agent, free base, free acid or salt or prodrug thereof; multiparticulate auris sensory cell modulating agent, free base, free acid or salt or prodrug thereof) with the aid of cyclodextrins, surfactants (e.g., poloxamers (407, 338, 188), tween (80, 60, 20, 81), PEG-hydrogenated castor oil, cosolvents like N-methyl-2-Pyrrolidone or the like and preparing pulsed release formulations using any procedure described herein.

In specific embodiments, any auris-compatible formulation described herein comprises one or more micronized pharmaceutical agents (e.g., auris sensory cell modulating agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises an auris sensory cell modulating agent as a neutral molecule, a free acid, a free base, a salt, a prodrug or any combination thereof. In certain embodiments, a pharmaceutical composition described herein comprises an auris sensory cell modulating agent as a micronized powder. In certain embodiments, a pharmaceutical composition described herein comprises an auris sensory cell modulating agent in the form of a micro-auris sensory cell modulating agent powder.

The multiparticulates and/or micronized auris sensory cell modulating agents described herein are delivered to an auris structure (e.g., inner ear) by means of any type of matrix including solid, liquid or gel matrices. In some embodiments, the multiparticulates and/or micronized auris sensory cell modulating agents described herein are delivered to an auris structure (e.g., inner ear) by means of any type of matrix including solid, liquid or gel matrices via intratympanic injection.

Tunable Release Characteristics

The release of active agent from any formulation, composition or device described herein is optionally tunable to the desired release characteristics. In some embodiments, a composition described herein is a solution that is substantially free of gelling components. In such instances, the composition provides essentially immediate release of an active agent. In some of such embodiments, the composition is useful in perfusion of otic structures, e.g., during surgery.

In some embodiments, a composition described herein is a solution that is substantially free of gelling components and comprises micronized otic agent (e.g., a corticosteroid). In some of such embodiments, the composition provides release of an active agent from about 2 days to about 4 days. In some embodiments, a composition described herein comprises a gelling agent (e.g., poloxamer 407) and provides release of an active agent over a period of from about 1 day to about 3 days. In some embodiments, a composition described herein comprises a gelling agent (e.g., poloxamer 407) and provides release of an active agent over a period of from about 1 day to about 5 days. In some embodiments, a composition described herein comprises a gelling agent (e.g., poloxamer 407) and provides release of an active agent over a period of from about 2 days to about 7 days.

In some embodiments, a composition described herein comprises a gelling agent (e.g., poloxamer 407) in combination with micronized otic agent and provides extended sustained release over a longer period of time. In some embodiments, a composition described herein comprises about 14-17% of a gelling agent (e.g., poloxamer 407) and micronized otic agent, and provides extended sustained release over a period of from about 1 week to about 3 weeks. In some embodiments, a composition described herein comprises about 18-21% of a gelling agent (e.g., poloxamer 407) and micronized otic agent, and provides extended sustained release over a period of from about 3 weeks to about 6 weeks.

Accordingly, the amount of gelling agent in a composition, and the particle size of an otic agent are tunable to the desired release profile of an otic agent from the composition.

As described herein, compositions comprising micronized otic agents provide extended release over a longer period of time compared to compositions comprising non-micronized otic agents. In some instances, the micronized otic agent provides a steady supply (e.g., +/−20%) of active agent via slow degradation and serves as a depot for the active agent; such a depot effect increases residence time of the otic agent in the ear. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

In some embodiments, the viscosity of any formulation described herein is designed to provide a suitable rate of release from an auris compatible gel. In some embodiments, the concentration of a thickening agent (e.g., gelling components such as polyoxyethylene-polyoxypropylene copolymers) allows for a tunable mean dissolution time (MDT). The MDT is inversely proportional to the release rate of an active agent from a composition or device described herein. Experimentally, the released otic agent is optionally fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is optionally calculated by:

$$MDT = \frac{nk^{-1/n}}{n+1}$$

For example, a linear relationship between the mean dissolution time (MDT) of a composition or device and the concentration of the gelling agent (e.g., poloxamer) indicates that the otic agent is released due to the erosion of the polymer gel (e.g., poloxamer) and not via diffusion. In another example, a non-linear relationship indicates release of otic agent via a combination of diffusion and/or polymer gel degradation. In another example, a faster gel elimination time course of a composition or device (a faster release of active agent) indicates lower mean dissolution time (MDT). The concentration of gelling components and/or active agent in a composition are tested to determine suitable parameters for MDT. In some embodiments, injection volumes are also tested to determine suitable parameters for preclinical and clinical studies. The gel strength and concentration of the active agent affects release kinetics of an otic agent from the composition. At low poloxamer concentration, elimination rate is accelerated (MDT is lower). An increase in otic agent concentration in the composition or device prolongs residence time and/or MDT of the otic agent in the ear.

In some embodiments, the MDT for poloxamer from a composition or device described herein is at least 6 hours. In some embodiments, the MDT for poloxamer from a composition or device described herein is at least 10 hours.

In some embodiments, the MDT for an active agent from a composition or device described herein is from about 30 hours to about 48 hours. In some embodiments, the MDT for an active agent from a composition or device described herein is from about 30 hours to about 96 hours. In some embodiments, the MDT for an active agent from a composition or device described herein is from about 30 hours to about 1 week. In some embodiments, the MDT for an active agent from a composition or device described herein is from about 1 week to about 6 weeks.

In certain embodiments, any controlled release otic formulation described herein increases the exposure of an otic agent and increases the Area Under the Curve (AUC) in otic fluids (e.g., endolymph and/or perilymph) by about 30%, about 40%, about 50%, about 60%, about 70%, about 80% or about 90% compared to a formulation that is not a controlled release otic formulation. In certain embodiments, any controlled release otic formulation described herein increases the exposure time of an otic agent and decreases the $C_{max}$ in otic fluids (e.g., endolymph and/or perilymph) by about 40%, about 30%, about 20%, or about 10%, compared to a formulation that is not a controlled release otic formulation. In certain embodiments, any controlled release otic formulation described herein alters (e.g. reduces) the ratio of $C_{max}$ to $C_{min}$ compared to a formulation that is not a controlled release otic formulation. In certain embodiments, any controlled release otic formulation described herein increases the exposure of an otic agent and increases the length of time that the concentration of an otic agent is above $C_{min}$ by about 30%, about 40%, about 50%, about 60%, about 70%, about 80% or about 90% compared to a formulation that is not a controlled release otic formulation. In certain instances, controlled release formulations described herein delay the time to $C_{max}$. In certain instances, the controlled steady release of a drug prolongs the time the concentration of the drug will stay above the $C_{min}$. In some embodiments, auris compositions described herein prolong the residence time of a drug in the inner ear and provide a stable drug exposure profile. In some instances, an increase in concentration of an active agent in the composition saturates the clearance process and allows for a more rapid and stable steady state to be reached.

Figure 5:
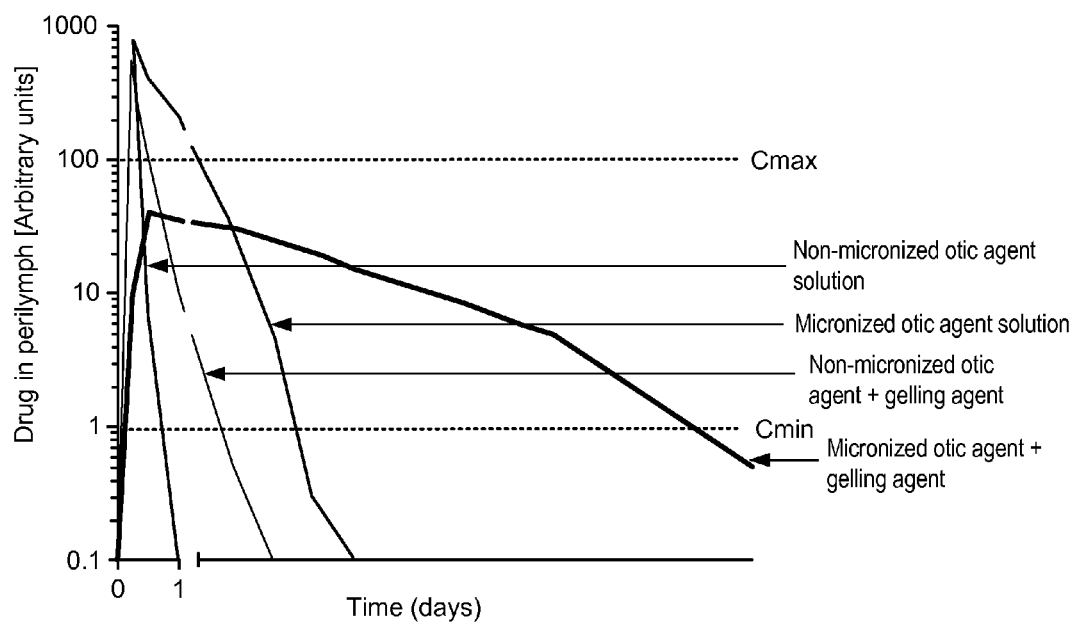
FIG. 5 shows predicted tunable release characteristics from four compositions

In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, or 1 week, 3 weeks, 6 weeks, 2 months). In some embodiments, the steady state concentration of active agent released from a controlled release formulation described herein is about 20 to about 50 times the steady state concentration of an active agent released from a formulation that is not a controlled release formulation. FIG. 5 shows predicted tunable release of an active agent from four compositions Pharmaceutical Formulations Provided herein are pharmaceutical compositions or devices that include at least one auris sensory cell modulating agent and a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

In some embodiments, the compositions or devices described herein include a dye to help enhance the visualization of the gel when applied. In some embodiments, dyes that are compatible with the auris-acceptable compositions or devices described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g., FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MRI dyes, iodine-base dyes, barium-based dyes or the like are also contemplated for use with any otic formulation described herein. Other dyes that are compatible with any formulation or composition described herein are listed in the Sigma-Aldrich catalog under dyes (which is included herein by reference for such disclosure).

In some embodiments, mechanical or imaging devices are used to monitor or survey the hearing, balance or other auris disorder. For example, magnetic resonance imaging (MRI) devices are specifically contemplated within the scope of the embodiments, wherein the MRI devices (for example, 3 Tesla MRI devices) are capable of evaluating Meniere Disease progression, and subsequent treatment with the pharmaceutical formulations disclosed herein. Gadolinium-based dyes, iodine-base dyes, barium-based dyes or the like are also contemplated for use with any auris-compatible composition or device described herein and/or with any mechanical or imaging devices described herein. In certain embodiments, gadolinium hydrate is used in combination with MRI and/or any pharmaceutical composition or device described herein to evaluate disease severity (e.g., size of endolymphatic hydrops), formulation penetration into the inner ear, and/or therapeutic effectiveness of the pharmaceutical formulations/devices in the otic diseases described herein (e.g., Meniere's disease).

Any pharmaceutical composition or device described herein is administered by locating the composition or device in contact with the crista fenestrae cochlea, the round window, the tympanic cavity, the tympanic membrane, the auris media or the auris externa.

In one specific embodiment of the auris-acceptable controlled release auris sensory cell modulating agent pharmaceutical formulations described herein, the auris sensory cell modulating agent is provided in a gel matrix, also referred to herein as "auris acceptable gel formulations," "auris interna-acceptable gel formulations," "auris media-acceptable gel formulations," "auris externa-acceptable gel formulations", "auris gel formulations" or variations thereof. All of the components of the gel formulation must be compatible with the targeted auris structure. Further, the gel formulations provide controlled release of the auris sensory cell modulating agent to the desired site within the targeted auris structure; in some embodiments, the gel formulation also has an immediate or rapid release component for delivery of the auris sensory cell modulating agent to the desired target site. In other embodiments, the gel formulation has a sustained release component for delivery of the auris sensory cell modulating agent. In some embodiments, the gel formulation comprises a multi-particulate (e.g., micronized) auris sensory cell modulating agent. In some embodiments, the auris gel formulations are biodegradable. In other embodiments, the auris gel formulations include a mucoadhesive excipient to allow adhesion to the external mucous layer of the round window membrane. In yet other embodiments, the auris gel formulations include a penetration enhancer excipient; in further embodiments, the auris gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel formulation contains a viscosity enhancing agent sufficient to provide a viscosity of between about 50,0000 and 1,000,000 centipoise.

In some embodiments, the compositions or devices described herein are low viscosity compositions or devices at body temperature. In some embodiments, low viscosity compositions or devices contain from about 1% to about 10% of a viscosity enhancing agent (e.g., gelling components such as polyoxyethylene-polyoxypropylene copolymers). In some embodiments, low viscosity compositions or devices contain from about 2% to about 10% of a viscosity enhancing agent (e.g., gelling components such as polyoxyethylene-polyoxypropylene copolymers). In some embodiments, low viscosity compositions or devices contain from about 5% to about 10% of a viscosity enhancing agent (e.g., gelling components such as polyoxyethylene-polyoxypropylene copolymers). In some embodiments, low viscosity compositions or devices are substantially free of a viscosity enhancing agent (e.g., gelling components such as polyoxyethylene-polyoxypropylene copolymers). In some embodiments, a low viscosity auris sensory cell modulator composition or device described herein provides an apparent viscosity of from about 100 cP to about 10,000 cP. In some embodiments, a low viscosity auris sensory cell modulator composition or device described herein provides an apparent viscosity of from about 500 cP to about 10,000 cP. In some embodiments, a low viscosity auris sensory cell modulator composition or device described herein provides an apparent viscosity of from about 1000 cP to about 10,000 cP. In some of such embodiments, a low viscosity auris sensory cell modulator composition or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy or the like. In some of such embodiments, a low viscosity auris sensory cell modulator composition or device is administered during an otic intervention. In other such embodiments, a low viscosity auris sensory cell modulator composition or device is administered before the otic intervention.

In some embodiments, the compositions or devices described herein are high viscosity compositions or devices at body temperature. In some embodiments, high viscosity compositions or devices contain from about 10% to about 25% of a viscosity enhancing agent (e.g., gelling components such as polyoxyethylene-polyoxypropylene copolymers). In some embodiments, high viscosity compositions or devices contain from about 14% to about 22% of a viscosity enhancing agent (e.g., gelling components such as polyoxyethylene-polyoxypropylene copolymers). In some embodiments, high viscosity compositions or devices contain from about 15% to about 21% of a viscosity enhancing agent (e.g., gelling components such as polyoxyethylene-polyoxypropylene copolymers). In some embodiments, a high viscosity auris sensory cell modulator composition or device described herein provides an apparent viscosity of from about 100,000 cP to about 1,000,000 cP. In some embodiments, a high viscosity auris sensory cell modulator composition or device described herein provides an apparent viscosity of from about 150,000 cP to about 500,000 cP. In some embodiments, a high viscosity auris sensory cell modulator composition or device described herein provides an apparent viscosity of from about 250,000 cP to about 500,000 cP. In some of such embodiments, a high viscosity composition or device is a liquid at room temperature and gels at about between room temperature and body temperature (including an individual with a serious fever, e.g., up to about 42° C.). In some embodiments, an auris sensory cell modulator high viscosity composition or device is administered as monotherapy for treatment of an otic disease or condition described herein. In some embodiments, an auris sensory cell modulator high viscosity composition or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy or the like. In some of such embodiments, a high viscosity auris sensory cell modulator composition or device is administered after the otic intervention. In other such embodiments, a high viscosity auris sensory cell modulator composition or device is administered before the otic intervention.

In other embodiments, the auris interna pharmaceutical formulations described herein further provide an auris-acceptable hydrogel; in yet other embodiments, the auris pharmaceutical formulations provide an auris-acceptable microsphere or microparticle; in still other embodiments, the auris pharmaceutical formulations provide an auris-acceptable liposome. In some embodiments, the auris pharmaceutical formulations provide an auris-acceptable foam; in yet other embodiments, the auris pharmaceutical formulations provide an auris-acceptable paint; in still further embodiments, the auris pharmaceutical formulations provide an auris-acceptable in situ forming spongy material. In some embodiments, the auris pharmaceutical formulations provide an auris-acceptable solvent release gel. In some embodiments, the auris pharmaceutical formulations provide an actinic radiation curable gel. Further embodiments include a thermoreversible gel in the auris pharmaceutical formulation, such that upon preparation of the gel at room temperature or below, the formulation is a fluid, but upon application of the gel into or near the auris interna and/or auris media target site, including the tympanic cavity, round window membrane or the crista fenestrae cochleae, the auris-pharmaceutical formulation stiffens or hardens into a gel-like substance.

In further or alternative embodiments, the auris gel formulations are capable of being administered on or near the round window membrane via intratympanic injection. In other embodiments, the auris gel formulations are administered on or near the round window or the crista fenestrae cochleae through entry via a post-auricular incision and surgical manipulation into or near the round window or the crista fenestrae cochleae area. Alternatively, the auris gel formulation is applied via syringe and needle, wherein the needle is inserted through the tympanic membrane and guided to the area of the round window or crista fenestrae cochleae. The auris gel formulations are then deposited on or near the round window or crista fenestrae cochleae for localized treatment of autoimmune otic disorders. In other embodiments, the auris gel formulations are applied via microcathethers implanted into the patient, and in yet further embodiments the formulations are administered via a pump device onto or near the round window membrane. In still further embodiments, the auris gel formulations are applied at or near the round window membrane via a microinjection device. In yet other embodiments, the auris gel formulations are applied in the tympanic cavity. In some embodiments, the auris gel formulations are applied on the tympanic membrane. In still other embodiments, the auris gel formulations are applied onto or in the auditory canal.

In further specific embodiments, any pharmaceutical composition or device described herein comprises a multiparticulate auris sensory cell modulating agent in a liquid matrix (e.g., a liquid composition for intratympanic injection, or otic drops). In certain embodiments, any pharmaceutical composition described herein comprises a multiparticulate auris sensory cell modulating agent in a solid matrix.

Controlled Release Formulations

In general, controlled release drug formulations impart control over the release of drug with respect to site of release and time of release within the body. As discussed herein, controlled release refers to immediate release, delayed release, sustained release, extended release, variable release, pulsatile release and bi-modal release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Accordingly, one aspect of the embodiments disclosed herein is to provide a controlled release auris sensory cell modulating agent auris-acceptable composition or device for the treatment of autoimmune disorders and/or inflammatory disorders. The controlled release aspect of the compositions and/or formulations and/or devices disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable gel, an auris-acceptable paint, an auris-acceptable foam, an auris-acceptable xerogel, an auris-acceptable microsphere or microparticle, an auris-acceptable hydrogel, an auris-acceptable in situ forming spongy material, an auris-acceptable actinic radiation curable gel, an auris-acceptable solvent release gel, an auris-acceptable liposome, an auris-acceptable nanocapsule or nanosphere, an auris-acceptable thermoreversible gel, or combinations thereof.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

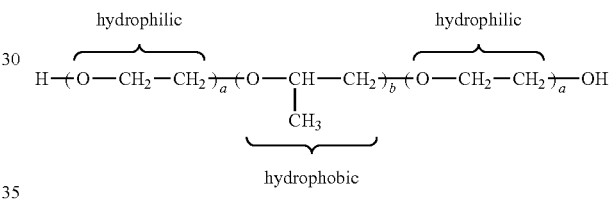

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117949, 6,201,072, and 6,287,588. It also includes biodegradable polymeric drug carriers disclosed in pending U.S. patent application Ser. Nos. 09/906, 041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly (orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, $\epsilon$-caprolactone, $\epsilon$-hydroxyhexanoic acid, $\gamma$-butyrolactone, $\gamma$-hydroxybutyric acid, $\delta$-valerolactone, $\delta$-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The auris sensory cell modulating agent and various additives such as buffers, salts, and preservatives are subsequently added and dissolved. In some instances the auris sensory cell modulating agent and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of which is incorporated herein by reference for such disclosure).

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising an auris sensory cell modulating agent and a pharmaceutically acceptable buffer. In another embodiment, the pharmaceutically acceptable excipient or carrier is a gelling agent.

In other embodiments, useful auris sensory cell modulating agent auris-acceptable pharmaceutical formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris media or auris interna's natural buffering system, or does not interfere with the natural pH of the endolymph or perilymph: depending on where in the cochlea the auris sensory cell modulating agent formulation is targeted. In some embodiments, from about 10 µM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris(hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled release formulations or devices comprising an auris sensory cell modulating agent and a viscosity enhancing agent. Suitable viscosity-enhancing agents include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the auris-acceptable viscosity agent include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the auris sensory cell modulating agents disclosed herein acts as a controlled release formulation, restricting the diffusion of the auris sensory cell modulating agents from the formulation. Moreover, the combination of carboxymethylated chitosan and alginate is optionally used to assist in increasing the permeability of the auris sensory cell modulating agents through the round window membrane.

In some embodiments is an enhanced viscosity formulation, comprising from about 0.1 mM and about 100 mM of an auris sensory cell modulating agent, a pharmaceutically acceptable viscosity agent, and water for injection, the concentration of the viscosity agent in the water being sufficient to provide a enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the auris sensory cell modulating agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the auris sensory cell modulating agent.

In some embodiments, the viscosity of the gel formulations presented herein are measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable formulation comprises at least one auris sensory cell modulating agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the otic therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* which is hereby incorporated with respect to this subject matter. The paints contemplated for use herein, are flexible such that they do not interfere with the propagation of pressure waves through the ear. Further, the paints may be applied as a liquid (i.e. solution, suspension, or emulsion), a semisolid (i.e. a gel, foam, paste, or jelly) or an aerosol.

In some embodiments, the otic therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic sidechains, cellulose and derivatives thereof, agar and derivatives thereof, such as agar stabilised with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

In some embodiments, other gel formulations are useful depending upon the particular auris sensory cell modulating agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the auris sensory cell modulating agent formulations described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable formulations disclosed and described herein.

In some formulations developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous formulation is needed. In a further embodiment, when slightly less viscous, or slightly more fluid auris-acceptable pharmaceutical gel formulations are desired, the biocompatible gel portion of the formulation comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in which the gel or matrix component of the mixture comprises not more than about 50% by weight, not more than about 40% by weight, not more than about 30% by weight, or even those than comprise not more than about 15% or about 20% by weight of the composition.

Auris-Acceptable Suspending Agents

In one embodiment, at least one auris sensory cell modulating agent is included in a pharmaceutically acceptable enhanced viscosity formulation wherein the formulation further comprises at least one suspending agent, wherein the suspending agent assists in imparting controlled release characteristics to the formulation. In some embodiments, suspending agents also serve to increase the viscosity of the auris-acceptable auris sensory cell modulating agent formulations and compositions.

Suspending agents include, by way of example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), sodium carboxymethylcellulose, methylcellulose, hydroxypropylmethylcellulose (hypromellose), hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In one embodiment, the present disclosure provides auris-acceptable gel compositions comprising a therapeutically effective amount of an auris sensory cell modulating agent in a hydroxyethyl cellulose gel. Hydroxyethyl cellulose (HEC) is obtained as a dry powder which is reconstituted in water or an aqueous buffer solution to give the desired viscosity (generally about 200 cps to about 30,000 cps, corresponding to about 0.2 to about 10% HEC). In one embodiment the concentration of HEC is between about 1% and about 15%, about 1% and about 2%, or about 1.5% to about 2%.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Auris-Acceptable Actinic Radiation Curable Gel

In other embodiments, the gel is an actinic radiation curable gel, such that following administration to or near the targeted auris structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

Auris-Acceptable Solvent Release Gel

In some embodiments, the gel is a solvent release gel such that the desired gel properties are formed after administration to or near the targeted auris structure, that is, as the solvent in the injected gel formulation diffuses out the gel, a gel having the desired gel properties is formed. For example, a formulation that comprises sucrose acetate isobutyrate, a pharmaceutically acceptable solvent, one or more additives, and the auris sensory cell modulating agent is administered at or near the round window membrane: diffusion of the solvent out of the injected formulation provides a depot having the desired gel properties. For example, use of a water soluble solvent provides a high viscosity depot when the solvent diffuses rapidly out of the injected formulation. On the other hand, use of a hydrophobic solvent (e.g., benzyl benzoate) provides a less viscous depot. One example of an auris-acceptable solvent release gel formulation is the SABER™ Delivery System marketed by DURECT Corporation.

Auris-Acceptable In Situ Forming Spongy Material

Also contemplated within the scope of the embodiments is the use of a spongy material, formed in situ in the auris interna or auris media. In some embodiments, the spongy material is formed from hyaluronic acid or its derivatives. The spongy material is impregnated with a desired auris sensory cell modulating agent and placed within the auris media so as to provide controlled release of the auris sensory cell modulating agent within the auris media, or in contact with the round window membrane so as to provide controlled release of the auris sensory cell modulating agent into the auris interna. In some embodiments, the spongy material is biodegradable.

Round Window Membrane Mucoadhesives

Also contemplated within the scope of the embodiments is the addition of a round window membrane mucoadhesive with the auris sensory cell modulating agent formulations and compositions and devices disclosed herein. The term 'mucoadhesion' is used for materials that bind to the mucin layer of a biological membrane, such as the external membrane of the 3-layered round window membrane. To serve as round window membrane mucoadhesive polymers, the polymers possess some general physiochemical features such as predominantly anionic hydrophilicity with numerous hydrogen bond forming groups, suitable surface property for wetting mucus/mucosal tissue surfaces or sufficient flexibility to penetrate the mucus network.

Round window membrane mucoadhesive agents that are used with the auris-acceptable formulations include, but are not limited to, at least one soluble polyvinylpyrrolidone polymer (PVP); a water-swellable, but water-insoluble, fibrous, cross-linked carboxy-functional polymer; a crosslinked poly (acrylic acid) (e.g. Carbopol® 947P); a carbomer homopolymer; a carbomer copolymer; a hydrophilic polysaccharide gum, maltodextrin, a cross-linked alginate gum gel, a water-dispersible polycarboxylated vinyl polymer, at least two particulate components selected from the group consisting of titanium dioxide, silicon dioxide, and clay, or a mixture thereof. The round window membrane mucoadhesive agent is optionally used in combination with an auris-acceptable viscosity increasing excipient, or used alone to increase the interaction of the composition with the mucosal layer target otic component. In one non-limiting example, the mucoadhesive agent is maltodextrin. In some embodiments, the mucoadhesive agent is an alginate gum. When used, the round window membrane mucoadhesive character imparted to the composition is at a level that is sufficient to deliver an effective amount of the auris sensory cell modulating agent composition to, for example, the mucosal layer of round window membrane or the crista fenestrae cochleae in an amount that coats the mucosal membrane, and thereafter deliver the composition to the affected areas, including by way of example only, the vestibular and/or cochlear structures of the auris interna. When used, the mucoadhesive characteristics of the compositions provided herein are determined, and using this information (along with the other teachings provided herein), the appropriate amounts are determined. One method for determining sufficient mucoadhesiveness includes monitoring changes in the interaction of the composition with a mucosal layer, including but not limited to measuring changes in residence or retention time of the composition in the absence and presence of the mucoadhesive excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of which is hereby incorporated by reference for such disclosure.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, includes fumed silicon dioxide, precipitated silicon dioxide, coacervated silicon dioxide, gel silicon dioxide, and mixtures thereof. Clay, if present, includes kaolin minerals, serpentine minerals, smectites, illite or a mixture thereof. For example, clay includes laponite, bentonite, hectorite, saponite, montmorillonites or a mixture thereof.

In one non-limiting example, the round window membrane mucoadhesive agent is maltodextrin. Maltodextrin is a carbohydrate produced by the hydrolysis of starch that is optionally derived from corn, potato, wheat or other plant products. Maltodextrin is optionally used either alone or in combination with other round window membrane mucoadhesive agents to impart mucoadhesive characteristics on the compositions disclosed herein. In one embodiment, a combination of maltodextrin and a carbopol polymer are used to increase the round window membrane mucoadhesive characteristics of the compositions or devices disclosed herein.

In another embodiment, the round window membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; dodecyl maltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β3-amino-alkyl ethers. In some embodiments, the round window membrane mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the round window membrane mucoadhesive agent is an alkyl-glycoside wherein the alkyl glycoside is dodecylmaltoside, tridecylmaltoside, and tetradecylmaltoside.

In some embodiments, the round window membrane mucoadhesive agent is an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the round window membrane mucoadhesive agent is an alkyl-glycoside wherein the alkyl-glycoside has a critical miscelle concentration (CMC) of less than about 1 mM in pure water or in aqueous solutions. In some embodiments, the round window membrane mucoadhesive agent is an alkyl-glycoside wherein an oxygen atom within the alkyl-glycoside is substituted with a sulfur atom. In some embodiments, the round window membrane mucoadhesive agent is an alkyl-glycoside wherein the alkylglycoside is the β anomer. In some embodiments, the round window membrane mucoadhesive agent is an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

Auris-Acceptable Controlled Release Particles

Auris sensory cell modulating agents and/or other pharmaceutical agents disclosed herein are optionally incorporated within controlled release particles, lipid complexes, liposomes, nanoparticles, microparticles, microspheres, coacervates, nanocapsules or other agents which enhance or facilitate the localized delivery of the auris sensory cell modulating agent. In some embodiments, a single enhanced viscosity formulation is used, in which at least one auris sensory cell modulating agent is present, while in other embodiments, a pharmaceutical formulation that comprises a mixture of two or more distinct enhanced viscosity formulations is used, in which at least one auris sensory cell modulating agent is present. In some embodiments, combinations of sols, gels and/or biocompatible matrices is also employed to provide desirable characteristics of the controlled release auris sensory cell modulating agent compositions or formulations. In certain embodiments, the controlled release auris sensory cell modulating agent formulations or compositions are cross-linked by one or more agents to alter or improve the properties of the composition.

Examples of microspheres relevant to the pharmaceutical formulations disclosed herein include: Luzzi, L. A., J. Pharm. Psy. 59:1367 (1970); U.S. Pat. No. 4,530,840; Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. No. 4,758,435; U.S. Pat. No. 3,773,919; U.S. Pat. No. 4,474,572. Examples of protein therapeutics formulated as microspheres include: U.S. Pat. No. 6,458,387; U.S. Pat. No. 6,268,053; U.S. Pat. No. 6,090,925; U.S. Pat. No. 5,981,719; and U.S. Pat. No. 5,578,709, and are herein incorporated by reference for such disclosure.

Microspheres usually have a spherical shape, although irregularly-shaped microparticles are possible. Microspheres may vary in size, ranging from submicron to 1000 micron diameters. Microspheres suitable for use with the auris-acceptable formulations disclosed herein are submicron to 250 micron diameter microspheres, allowing administration by injection with a standard gauge needle. The auris-acceptable microspheres are prepared by any method which produces microspheres in a size range acceptable for use in an injectable composition. Injection is optionally accomplished with standard gauge needles used for administering liquid compositions.

Suitable examples of polymeric matrix materials for use in the auris-acceptable controlled release particles herein include poly(glycolic acid), poly-d,l-lactic acid, poly-l-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) are optionally used in the method disclosed herein. For example, poly (d,l-lactic-co-glycolic acid) is commercially available from Boehringer-Ingelheim as RESOMER RG 503H. This product has a mole percent composition of 50% lactide and 50% glycolide. These copolymers are available in a wide range of molecular weights and ratios of lactic acid to glycolic acid. One embodiment includes the use of the polymer poly(d,l-lactide-co-glycolide). The molar ratio of lactide to glycolide in such a copolymer includes the range of from about 95:5 to about 50:50.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials a microsphere formulation is made such that the resulting microspheres exhibit both diffusional release and biodegradation release properties. This is useful in affording multiphasic release patterns.

A variety of methods are known by which compounds are encapsulated in microspheres. In these methods, the auris sensory cell modulating agent is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled release auris sensory cell modulating agent formulations are made through the incorporation of the auris sensory cell modulating agents and/or other pharmaceutical agents into ethylene-vinyl acetate copolymer matrices. (See U.S. Pat. No. 6,083,534, incorporated herein for such disclosure). In another embodiment, auris sensory cell modulating agents are incorporated into poly (lactic-glycolic acid) or poly-L-lactic acid microspheres. Id. In yet another embodiment, the auris sensory cell modulating agents are encapsulated into alginate microspheres. (See U.S. Pat. No. 6,036,978, incorporated herein for such disclosure). Biocompatible methacrylate-based polymers to encapsulate the auris sensory cell modulating agent compounds or compositions are optionally used in the formulations and methods disclosed herein. A wide range of methacrylate-based polymer systems are commercially available, such as the EUDRAGIT polymers marketed by Evonik.

One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic formulations (Naha et al, Journal of Microencapsulation 4 Feb., 2008 (online publication)). In one embodiment, the enhanced viscosity auris-acceptable formulations described herein comprises auris sensory cell modulating agent microspheres wherein the microspheres are formed from a methacrylate polymer or copolymer. In an additional embodiment, the enhanced viscosity formulation described herein comprises auris sensory cell modulating agent microspheres wherein the microspheres are mucoadhesive. Other controlled release systems, including incorporation or deposit of polymeric materials or matrices onto solid or hollow spheres containing auris sensory cell modulating agents, are also explicitly contemplated within the embodiments disclosed herein. The types of controlled release systems available without significantly losing activity of the auris sensory cell modulating agent are determined using the teachings, examples, and principles disclosed herein An example of a conventional microencapsulation process for pharmaceutical preparations is shown in U.S. Pat. No. 3,737,337, incorporated herein by reference for such disclosure. The auris sensory cell modulating agent substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of auris sensory cell modulating agents, the microspheres form when the solvent containing an active agent and a polymer is emulsified or dispersed in an immiscible solution by stirring, agitating, vibrating, or some other dynamic mixing technique, often for a relatively long period of time.

Methods for the construction of microspheres are also described in U.S. Pat. No. 4,389,330, and U.S. Pat. No. 4,530,840, incorporated herein by reference for such disclosure. The desired auris sensory cell modulating agent is dissolved or dispersed in an appropriate solvent. To the agent-containing medium is added the polymeric matrix material in an amount relative to the active ingredient which gives a product of the desired loading of active agent. Optionally, all of the ingredients of the auris sensory cell modulating agent microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and includes water although nonaqueous media such as xylene and toluene and synthetic oils and natural oils are optionally used. Optionally, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion is optionally formed by adding small drops of the active agent-wall forming material solution to the continuous phase processing medium. The temperature during the formation of the emulsion is not especially critical but influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature which maintains stable operating conditions, which preferred temperature being about 15° C. to 60° C., depending upon the drug and excipient selected.

The dispersion which is formed is a stable emulsion and from this dispersion the organic solvent immiscible fluid is optionally partially removed in the first step of the solvent removal process. The solvent is removed by techniques such as heating, the application of a reduced pressure or a combination of both. The temperature employed to evaporate solvent from the microdroplets is not critical, but should not be that high that it degrades the auris sensory cell modulating agent employed in the preparation of a given microparticle, nor should it be so high as to evaporate solvent at such a rapid rate to cause defects in the wall forming material. Generally, from 5 to 75%, of the solvent is removed in the first solvent removal step.

After the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

Following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. The rate of extraction medium replenishment of a given process is a variable which is determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the auris sensory cell modulating agent since core loadings of up to 80 wt. %, preferably up to 60 wt. % are obtained.

Alternatively, controlled release microspheres containing an auris sensory cell modulating agent is prepared through the use of static mixers. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer is optionally used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an auris sensory cell modulating agent using a static mixer process, an organic phase and an aqueous phase are combined. The organic and aqueous phases are largely or substantially immiscible, with the aqueous phase constituting the continuous phase of the emulsion. The organic phase includes an auris sensory cell modulating agent as well as a wall-forming polymer or polymeric matrix material. The organic phase is prepared by dissolving an auris sensory cell modulating agent in an organic or other suitable solvent, or by forming a dispersion or an emulsion containing the auris sensory cell modulating agent. The organic phase and the aqueous phase are pumped so that the two phases flow simultaneously through a static mixer, thereby forming an emulsion which comprises microspheres containing the auris sensory cell modulating agent encapsulated in the polymeric matrix material. The organic and aqueous phases are pumped through the static mixer into a large volume of quench liquid to extract or remove the organic solvent. Organic solvent is optionally removed from the microspheres while they are washing or being stirred in the quench liquid. After the microspheres are washed in a quench liquid, they are isolated, as through a sieve, and dried.

In one embodiment, microspheres are prepared using a static mixer. The process is not limited to the solvent extraction technique discussed above, but is used with other encapsulation techniques. For example, the process is optionally used with a phase separation encapsulation technique. To do so, an organic phase is prepared that comprises an auris sensory cell modulating agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference for such disclosure. An alternative process involves the use of a static mixer with co-solvents. In this process, biodegradable microspheres comprising a biodegradable polymeric binder and an auris sensory cell modulating agent are prepared, which comprises a blend of at least two substantially non-toxic solvents, free of halogenated hydrocarbons to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. This process has the advantage that less extraction medium is required because the solubility of one solvent in water is substantially independent of the other and solvent selection is increased, especially with solvents that are particularly difficult to extract.

Nanoparticles are also contemplated for use with the auris sensory cell modulating agents disclosed herein. Nanoparticles are material structures of about 100 nm or less in size. One use of nanoparticles in pharmaceutical formulations is the formation of suspensions as the interaction of the particle surface with solvent is strong enough to overcome differences in density. Nanoparticle suspensions are sterilized as the nanoparticles are small enough to be subjected to sterilizing filtration (see, e.g., U.S. Pat. No. 6,139,870, herein incorporated by reference for such disclosure). Nanoparticles comprise at least one hydrophobic, water-insoluble and water-indispersible polymer or copolymer emulsified in a solution or aqueous dispersion of surfactants, phospholipids or fatty acids. The auris sensory cell modulating agent is optionally introduced with the polymer or the copolymer into the nanoparticles.

Lipid nanocapsules as controlled release structures, as well for penetrating the round window membrane and reaching auris interna and/or auris media targets, is also contemplated herein. Lipid nanocapsules are optionally formed by emulsifying capric and caprylic acid triglycerides (Labrafac WL 1349; avg. mw 512), soybean lecithin (LIPOID® S75-3; 69% phosphatidylcholine and other phospholipids), surfactant (for example, Solutol HS15), a mixture of polyethylene glycol 660 hydroxystearate and free polyethylene glycol 660; NaCl and water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate the auris sensory cell modulating agents, the agent is optionally added just prior to the dilution with cold water.

Auris sensory cell modulating agents are also inserted into the lipid nanocapsules by incubation for 90 minutes with an aqueous micellar solution of the auris active agent. The suspension is then vortexed every 15 minutes, and then quenched in an ice bath for 1 minute.

Suitable auris-acceptable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) are optionally used to prepare nanoparticles.

The auris-acceptable phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

Fatty acids for use with the auris-acceptable formulations are chosen from, by way of example, lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable auris-acceptable surfactants are selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination.

Representative examples of auris-acceptable surfactants include cetyl pyridinium chloride, gelatin, casein, lecithin (phosphatides), dextran, glycerol, gum acacia, cholesterol, tragacanth, stearic acid, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers, poloxamines, a charged phospholipid such as dimyristoyl phophatidyl glycerol, dioctylsulfosuccinate (DOSS); Tetronic® 1508, dialkylesters of sodium sulfosuccinic acid, Duponol P, Tritons X-200, Crodestas F-110, p-isononylphenoxypoly-(glycidol), Crodestas SL-40 (Croda, Inc.); and SA9OHCO, which is $C_{18}H_{37}CH_2$ $(CON(CH_3))$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like. Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference for such disclosure.

The hydrophobic, water-insoluble and water-indispersible polymer or copolymer may be chosen from biocompatible and biodegradable polymers, for example lactic or glycolic acid polymers and copolymers thereof, or polylactic/polyethylene (or polypropylene) oxide copolymers, preferably with molecular weights of between 1000 and 200,000, polyhydroxybutyric acid polymers, polylactones of fatty acids containing at least 12 carbon atoms, or polyanhydrides.

The nanoparticles may be obtained by coacervation, or by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are optionally employed to fabricate the auris sensory cell modulating agent nanoparticles that are within the scope of the embodiments. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is optionally used to prepare nanoparticles has been described (Hansen et al J Phys Chem 92, 2189-96, 1988). In other embodiments, ultrasonic devices, flow through homogenizers or supercritical CO2 devices may be used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound auris sensory cell modulating agent or other pharmaceutical compound from free auris sensory cell modulating agent or other pharmaceutical compound, or to select a suitable size range of auris sensory cell modulating agent-containing nanoparticles. Various SEC media, such as Superdex 200, Superose 6, Sephacryl 1000 are commercially available and are employed for the size-based fractionation of such mixtures. Additionally, nanoparticles are optionally purified by centrifugation, membrane filtration and by use of other molecular sieving devices, crosslinked gels/materials and membranes.

Auris-Acceptable Cyclodextrin and Other Stabilizing Formulations

In a specific embodiment, the auris-acceptable formulations alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

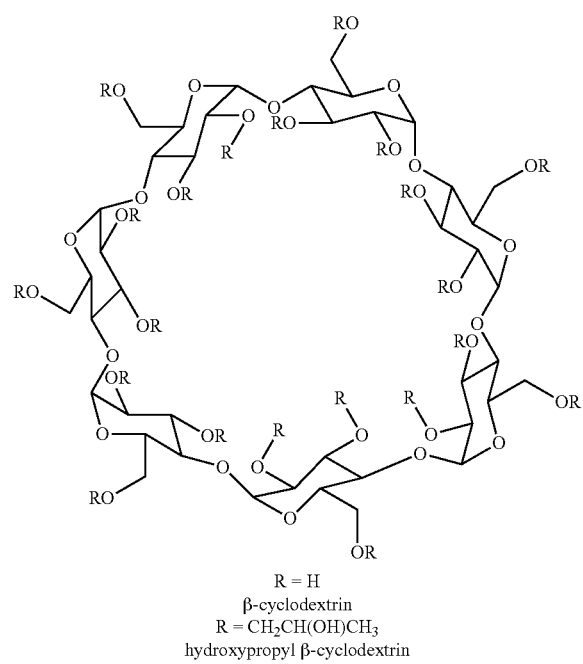

R = H
β-cyclodextrin
R = CH₂CH(OH)CH₃
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HP-βCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the auris-acceptable auris sensory cell modulating agents within the formulations described herein. In other embodiments, cyclodextrins in addition serve as controlled release excipients within the formulations described herein.

By way of example only, cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, formulation considerations, or other factors associated with the therapeutically active agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the auris sensory cell modulating agent and/or function as a controlled release excipient in any of the formulations described herein is selected using the principles, examples, and teachings described herein.

Other stabilizers that are useful in the auris-acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation (e.g., oleic acid, waxes), or improves the mixing of various components in the formulation (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In other embodiments, stabilizers are present in sufficient amounts to inhibit the degradation of the auris sensory cell modulating agent. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Additional useful auris sensory cell modulating agent auris-acceptable formulations include one or more anti-aggregation additives to enhance stability of auris sensory cell modulating agent formulations by reducing the rate of protein aggregation. The anti-aggregation additive selected depends upon the nature of the conditions to which the auris sensory cell modulating agents, for example auris sensory cell modulating agent antibodies are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more auris-acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more auris-acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the auris-acceptable pharmaceutical formulations described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months. In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof, b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the auris-acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

In one embodiment, diluents are also used to stabilize the auris sensory cell modulating agent or other pharmaceutical compounds because they provide a more stable environment. Salts dissolved in buffered solutions (which also can provide pH control or maintenance) are utilized as diluents, including, but not limited to a phosphate buffered saline solution. In other embodiments, the gel formulation is isotonic with the endolymph or the perilymph: depending on the portion of the cochlea that the auris sensory cell modulating agent formulation is targeted. Isotonic formulations are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/kg to about 400 mOsm/kg, from about 280 mOsm/kg to about 320 mOsm/kg. The amount of tonicity agents will depend on the target structure of the pharmaceutical formulation, as described herein.

Useful tonicity compositions also include one or more salts in an amount required to bring osmolality of the composition into an acceptable range for the perilymph or the endolymph. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the auris-acceptable gel formulations disclosed herein alternatively or additionally contains preservatives to prevent microbial growth. Suitable auris-acceptable preservatives for use in the enhanced viscosity formulations described herein include, but are not limited to benzoic acid, boric acid, p-hydroxybenzoates, alcohols, quarternary compounds, stabilized chlorine dioxide, mercurials, such as merfen and thiomersal, mixtures of the foregoing and the like.

In a further embodiment, the preservative is, by way of example only, an antimicrobial agent, within the auris-acceptable formulations presented herein. In one embodiment, the formulation includes a preservative such as by way of example only, methyl paraben, sodium bisulfite, sodium thiosulfate, ascorbate, chorobutanol, thimerosal, parabens, benzyl alcohol, phenylethanol and others. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the auris sensory cell modulating agent disclosed herein.

Suitable auris-acceptable water soluble preservatives which are employed in the drug delivery vehicle include sodium bisulfite, sodium thiosulfate, ascorbate, chorobutanol, thimerosal, parabens, benzyl alcohol, Butylated hydroxytoluene (BHT), phenylethanol and others. These agents are present, generally, in amounts of about 0.001% to about 5% by weight and, preferably, in the amount of about 0.01 to about 2% by weight. In some embodiments, auris-compatible formulations described herein are free of preservatives.

Round Window Membrane Penetration Enhancers

In another embodiment, the formulation further comprises one or more round window membrane penetration enhancers. Penetration across the round window membrane is enhanced by the presence of round window membrane penetration enhancers. Round window membrane penetration enhancers are chemical entities that facilitate transport of coadministered substances across the round window membrane. Round window membrane penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween® 80, nonylphenoxypolyethylene (NP-POE), polysorbates and the like, function as round window membrane penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, glycerol, propanediol and the like) also function as round window membrane penetration enhancers.

In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl glycoside is dodecyl-maltoside. In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)). In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions.

Round Window Membrane Permeable Liposomes

Liposomes or lipid particles may also be employed to encapsulate the auris sensory cell modulating agent formulations or compositions. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as auris sensory cell modulating agents or other pharmaceutical agent carriers. They are biologically inert, biodegradable, non-toxic and non-antigenic. Liposomes are formed in various sizes and with varying compositions and surface properties. Additionally, they are able to entrap a wide variety of agents and release the agent at the site of liposome collapse.

Suitable phospholipids for use in auris-acceptable liposomes here are, for example, phosphatidyl cholines, ethanolamines and serines, sphingomyelins, cardiolipins, plasmalogens, phosphatidic acids and cerebrosides, in particular those which are soluble together with the auris sensory cell modulating agents herein in non-toxic, pharmaceutically acceptable organic solvents. Preferred phospholipids are, for example, phosphatidyl choline, phosphatidyl ethanolamine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation range from about 10 to about 30%, preferably from about 15 to about 25% and in particular is about 20%.

Lipophilic additives may be employed advantageously to modify selectively the characteristics of the liposomes. Examples of such additives include by way of example only, stearylamine, phosphatidic acid, tocopherol, cholesterol, cholesterol hemisuccinate and lanolin extracts. The amount of lipophilic additive used range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the auris sensory cell modulating agent and other pharmaceutical compounds are employed in conjunction with a non-toxic, pharmaceutically acceptable organic solvent system which dissolve said ingredients. Said solvent system not only must dissolve the auris sensory cell modulating agent completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol range from about 2:1 to about 1:3, in particular from about 1:1 to about 1:2.5 and preferably is about 1:2. The amount of tetraglycol in the final composition thus vary from 5 to 20%, in particular from 5 to 15% and preferably is approximately 10%. The amount of dimethylisosorbide in the final composition thus range from 3 to 10%, in particular from 3 to 7% and preferably is approximately 5%.

The term "organic component" as used hereinafter refers to mixtures comprising said phospholipid, lipophilic additives and organic solvents. The auris sensory cell modulating agent may be dissolved in the organic component, or other means to maintain full activity of the agent. The amount of auris sensory cell modulating agent in the final formulation may range from 0.1 to 5.0%. In addition, other ingredients such as antioxidants may be added to the organic component. Examples include tocopherol, butylated hydroxyanisole, butylated hydroxytoluene, ascorbyl palmitate, ascorbyl oleate and the like.

Liposomal formulations are alternatively prepared, for auris sensory cell modulating agents or other pharmaceutical agents that are moderately heat-resistant, by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, for example, a high-shear mixer; and (d) adding a viscosity enhancing agent to the resulting mixture while further homogenizing. The aqueous component is optionally placed in a suitable vessel which is equipped with a homogenizer and homogenization is effected by creating turbulence during the injection of the organic component. Any mixing means or homogenizer which exerts high shear forces on the mixture may be employed. Generally, a mixer capable of speeds from about 1,500 to 20,000 rpm, in particular from about 3,000 to about 6,000 rpm may be employed. Suitable viscosity enhancing agents for use in process step (d) are for example, xanthan gum, hydroxypropyl cellulose, hydroxypropyl methylcellulose or mixtures thereof. The amount of viscosity enhancing agent depends on the nature and the concentration of the other ingredients and in general ranges from about 0.5 to 2.0%, or approximately 1.5%. In order to prevent degradation of the materials used during the preparation of the liposomal formulation, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Suitable carriers for use in an auris-acceptable formulation described herein include, but are not limited to, any pharmaceutically acceptable solvent compatible with the targeted auris structure's physiological environment. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based auris-acceptable enhanced viscosity formulations utilized in the preparation of pharmaceutical delivery vehicles comprise at least one auris sensory cell modulating agent containing at least about 0.1% of the water-soluble glycerin compound or more. In some embodiments, the percentage of auris sensory cell modulating agent is varied between about 1% and about 95%, between about 5% and about 80%, between about 10% and about 60% or more of the weight or volume of the total pharmaceutical formulation. In some embodiments, the amount of the compound(s) in each therapeutically useful auris sensory cell modulating agent formulation is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the auris-acceptable pharmaceutical gels also contain co-solvents, preservatives, cosolvents, ionic strength and osmolality adjustors and other excipients in addition to buffering agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition.

Cosolvents are used to enhance auris sensory cell modulating agent solubility, however, some auris sensory cell modulating agents or other pharmaceutical compounds are insoluble. These are often suspended in the polymer vehicle with the aid of suitable suspending or viscosity enhancing agents.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release auris sensory cell modulating agent formulation, it is advised to avoid or combine the appropriate excipients, diluents or carriers to lessen or eliminate potential ototoxic components from the formulation, or to decrease the amount of such excipients, diluents or carriers. Optionally, a controlled release auris sensory cell modulating agent formulation includes otoprotective agents, such as antioxidants, alpha lipoic acid, calcium, fosfomycin or iron chelators, to counteract potential ototoxic effects that may arise from the use of specific therapeutic agents or excipients, diluents or carriers.

Thof therapeutically acceptable otic formulations:

| Example Formulation | Example Characteristics |
|---|---|
| Chitosan glycerophosphate (CGP) | tunable degradation of matrix in vitro<br>tunable TACE inhibitor release in vitro: e.g., ~50% of drug released after 24 hrs<br>biodegradable<br>compatible with drug delivery to the inner ear<br>suitable for macromolecules and hydrophobic drugs |
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks |

-continued

| Example Formulation | Example Characteristics |
| --- | --- |
| PEO-PPO-PEO triblock copolymers (e.g., Pluronic or Poloxameres) (e.g., F127) | biodegradable<br>subcutaneous injection of solution: e.g., gel forms within seconds and is intact after 1 month<br>Tunable sol-gel transition temperature: e.g., decreases with increasing F127 concentration |
| Chitosan glycerophosphate with drug-loaded liposomes | CGP formulation tolerates liposomes: e.g., up to 15 uM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

The formulations disclosed herein alternatively encompass an otoprotectant agent in addition to the at least one active agent and/or excipients, including but not limited to such agents as antioxidants, alpha lipoic acid, calcium, fosfomycin or iron chelators, to counteract potential ototoxic effects that may arise from the use of specific therapeutic agents or excipients, diluents or carriers.

Modes of Treatment

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the auris sensory cell modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the auris sensory cell modulating agent compositions or formulations, the gauge level of the syringe or hypodermic needle may be varied accordingly. In another embodiment, the internal diameter of the needle can be increased by reducing the wall thickness of the needle (commonly referred as thin wall or extra thin wall needles) to reduce the possibility of needle clogging while maintaining an adequate needle gauge.

In another embodiment, the needle is a hypodermic needle used for instant delivery of the gel formulation. The hypodermic needle may be a single use needle or a disposable needle. In some embodiments, a syringe may be used for delivery of the pharmaceutically acceptable gel-based auris sensory cell modulating agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the auris sensory cell modulating agent pharmaceutically acceptable gel-based compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the auris sensory cell modulating agent or other pharmaceutical compounds contained therein.

In some embodiments, the syringe comprises a cylindrical syringe body wherein the body is compartmentalized in that each compartment is able to store at least one component of the auris-acceptable auris sensory cell modulating agent gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises an auris sensory cell modulating agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The auris-acceptable compositions or formulations containing the auris sensory cell modulating agent compound(s) described herein are administered for prophylactic and/or therapeutic treatments. In therapeutic applications, the auris sensory cell modulating agent compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

Frequency of Administration

In some embodiments, a composition disclosed herein is administered to an individual in need thereof once. In some embodiments, a composition disclosed herein is administered to an individual in need thereof more than once. In some embodiments, a first administration of a composition disclosed herein is followed by a second administration of a composition disclosed herein. In some embodiments, a first administration of a composition disclosed herein is followed by a second and third administration of a composition disclosed herein. In some embodiments, a first administration of a composition disclosed herein is followed by a second, third, and fourth administration of a composition disclosed herein. In some embodiments, a first administration of a composition disclosed herein is followed by a second, third, fourth, and fifth administration of a composition disclosed herein. In some embodiments, a first administration of a composition disclosed herein is followed by a drug holiday.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an auris sensory cell modulator may be administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the auris sensory cell modulating agent compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the auris sensory cell modulating agent compounds may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's otic conditions has occurred, a maintenance auris sensory cell modulating agent dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of auris sensory cell modulating agent that will correspond to such an amount will vary depending upon factors such as the particular compound, disease condition and its severity, according to the particular circumstances surrounding the case, including, e.g., the specific auris sensory cell modulating agent being administered, the route of administration, the autoimmune condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

In some embodiments, the initial administration is a particular auris sensory cell modulating agent and the subsequent administration a different formulation or auris sensory cell modulating agent.

Pharmacokinetics of Controlled Release Formulations

In one embodiment, the formulations disclosed herein additionally provides an immediate release of an auris sensory cell modulating agent from the composition, or within 1 minute, or within 5 minutes, or within 10 minutes, or within 15 minutes, or within 30 minutes, or within 60 minutes or within 90 minutes. In other embodiments, a therapeutically effective amount of at least one auris sensory cell modulating agent is released from the composition immediately, or within 1 minute, or within 5 minutes, or within 10 minutes, or within 15 minutes, or within 30 minutes, or within 60 minutes or within 90 minutes. In certain embodiments the composition comprises an auris-pharmaceutically acceptable gel formulation providing immediate release of at least one auris sensory cell modulating agent. Additional embodiments of the formulation may also include an agent that enhances the viscosity of the formulations included herein.

In other or further embodiments, the formulation provides an extended release formulation of at least one auris sensory cell modulating agent. In certain embodiments, diffusion of at least one auris sensory cell modulating agent from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one auris sensory cell modulating agent is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an auris sensory cell modulating agent. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first auris sensory cell modulating agent and an extended release of a second auris sensory cell modulating agent or other therapeutic agent. In yet other embodiments, the formulation provides an immediate release and extended release formulation of at least one auris sensory cell modulating agent, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first auris sensory cell modulating agent and second therapeutic agent, respectively.

In a specific embodiment the formulation provides a therapeutically effective amount of at least one auris sensory cell modulating agent at the site of disease with essentially no systemic exposure. In an additional embodiment the formulation provides a therapeutically effective amount of at least one auris sensory cell modulating agent at the site of disease with essentially no detectable systemic exposure. In other embodiments, the formulation provides a therapeutically effective amount of at least one auris sensory cell modulating agent at the site of disease with little or no detectable systemic exposure.

The combination of immediate release, delayed release and/or extended release auris sensory cell modulating agent compositions or formulations may be combined with other pharmaceutical agents, as well as the excipients, diluents, stabilizers, tonicity agents and other components disclosed herein. As such, depending upon the auris sensory cell modulating agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the auris sensory cell modulating agent formulations described herein are determined by injecting the formulation on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a formulation over a 1 week period), the test animal is euthanized and a 5 mL sample of the perilymph fluid is tested. The inner ear removed and tested for the presence of the auris sensory cell modulating agent. As needed, the level of auris sensory cell modulating agent is measured in other organs. In addition, the systemic level of the auris sensory cell modulating agent is measured by withdrawing a blood sample from the test animal. In order to determine whether the formulation impedes hearing, the hearing of the test animal is optionally tested.

Alternatively, an inner ear is provided (as removed from a test animal) and the migration of the auris sensory cell modulating agent is measured. As yet another alternative, an in vitro model of a round window membrane is provided and the migration of the auris sensory cell modulating agent is measured.

Kits/Articles of Manufacture

The disclosure also provides kits for preventing, treating or ameliorating the symptoms of a disease or disorder in a mammal. Such kits generally will comprise one or more of the auris sensory cell modulating agent controlled-release compositions or devices disclosed herein, and instructions for using the kit. The disclosure also contemplates the use of one or more of the auris sensory cell modulating agent controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of auris sensory cell modulating agent formulations compositions provided herein are contemplated as are a variety of treatments for any disease, disorder, or condition that would benefit by controlled release administration of an auris sensory cell modulating agent to the inner ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1

Preparation of a Thermoreversible Gel AMN082 Formulation

| Ingredient | Quantity (mg/g of formulation) |
|---|---|
| AMN082 | 3.0 |
| Methylparaben | 0.3 |
| Hypromellose | 3.0 |
| Poloxamer 407 | 54 |
| TRIS HCl buffer (0.1M) | 239.7 |

AMN082 is supplied as a solid. It is rehydrated in water to a final molarity of 10 mM.

A 10-g batch of gel formulation containing 1.0% of AMN082 is prepared by first suspending Poloxamer 407 (BASF Corp.) in TRIS HCl buffer (0.1 M). The Poloxamer 407 and TRIS are mixed under agitation overnight at 4° C. to ensure complete dissolution of the Poloxamer 407 in the TRIS. The hypromellose, methylparaben and additional TRIS HCl buffer (0.1 M) is added. The composition is stirred until dissolution is observed. A solution of AMN082 is added and the composition is mixed until a homogenous gel is produced. The mixture is maintained below room temperature until use.

Example 2

Preparation of a Mucoadhesive, Thermoreversible Gel AMN082 Formulation

| Ingredient | Quantity (mg/g of formulation) |
|---|---|
| AMN082 | 3.0 |
| methylparaben | 0.3 |
| Hypromellose | 3.0 |
| Carbopol 934P | 0.6 |
| Poloxamer 407 | 54 |
| TRIS HCl buffer (0.1M) | 239.1 |

AMN082 is supplied as a solid. It is rehydrated in water to a final molarity of 10 mM.

A 10-g batch of mucoadhesive gel formulation containing 1.0% of AMN082 is prepared by first suspending Poloxamer 407 (BASF Corp.) and Carbopol 934P in TRIS HCl buffer (0.1 M). The Poloxamer 407, Carbopol 934P and TRIS are mixed under agitation overnight at 4° C. to ensure complete dissolution of the Poloxamer 407 and Carbopol 934P in the TRIS. The hypromellose, methylparaben and additional TRIS HCl buffer (0.1 M) is added. The composition is stirred until dissolution is observed. The AMN082 solution is added and the composition is mixed until a homogenous gel is produced. The mixture is maintained below room temperature until use.

Example 3

Preparation of a Hydrogel-Based CNQX Formulation

| Ingredient | Quantity (mg/g of formulation) |
|---|---|
| CNQX | 15.0 |
| paraffin oil | 300.0 |
| trihydroxystearate | 15.0 |
| cetyl dimethicon copolyol | 45.0 |
| water | qs ad 1000 |
| phosphate buffer pH 7.4 | qs pH 7.4 |

The cream-type formulation is first prepared by gently mixing CNQX with water until the CNQX is dissolved. Then, the oil base is prepared by mixing paraffin oil, trihydroxystearate and cetyl dimethicon copolyol at temperatures up to 60° C. The oil base is cooled to room temperature and the CNQX solution is added. The two phases are mixed until a homogenous, monophasic hydrogel is formed.

Example 4

Preparation of a Gel Carbamazepine Formulation

| Ingredient | Quantity (mg/g of formulation) |
|---|---|
| Carbamazepine | 6.4 |
| chitosan | 3.2 |
| Glycerophosphate disodium | 12.8 |
| water | 134.4 |

A 5 ml solution of acetic acid is titrated to a pH of about 4.0. The chitosan is added to achieve a pH of about 5.5. The carbamazepine is then dissolved in the chitosan solution. This solution is sterilized by filtration. A 5 ml aqueous solution of glycerophosphate disodium is also prepared and sterilized. The two solutions are mixed and within 2 h at 37° C., the desired gel is formed.

Example 5

Preparation of a Mucoadhesive, Thermoreversible Gel D-Methionine Formulation

| Ingredient | Quantity (mg/g of formulation) |
|---|---|
| D-Methionine | 3.0 |
| Benzyl alcohol | 0.3 |

-continued

| Ingredient | Quantity (mg/g of formulation) |
|---|---|
| Hypromellose | 3.0 |
| Carbopol 934P | 0.6 |
| Poloxamer 407 | 54 |
| Phosphate buffer, pH 7.4 | qs to grams |

D-Methionine is dissolved in phosphate buffer. A 10-g batch of mucoadhesive gel formulation containing D-methionine is prepared by first suspending Poloxamer 407 (BASF Corp.) and Carbopol 934P in phosphate buffer. The Poloxamer 407, Carbopol 934P and phosphate buffer are mixed under agitation overnight at 4° C. to ensure complete dissolution of the Poloxamer 407 and Carbopol 934P in the buffer. The hypromellose, benzyl alcohol and additional phosphate buffer is added to the mixture. The composition is stirred until dissolution is observed. The D-methionine solution is added and the composition is mixed until a homogenous gel is produced. The mixture is maintained below room temperature until use.

Example 6

Preparation of a Liposomal AMN082 Formulation

| Ingredient | Quantity (mg/g) |
|---|---|
| AMN082 | 3.0 |
| soya lecithin | 200.0 |
| cholesterol | 20.0 |
| tetraglycol | 100.0 |
| dimethylisosorbide | 50.0 |
| methylparaben | 2.0 |
| propylparaben | 0.2 |
| BHT | 0.1 |
| sodium chloride | 1.0 |
| HPMC | 15.0 |
| sodium hydroxide | 0.6 |
| citric acid | 1.0 |
| purified water, USP | 603.6 |

AMN082 is supplied as a solid. It is rehydrated in water to a final molarity of 10 mM.

Heat the soya lecithin, tetraglycol and dimethyl isosorbide to about 70-75° C. Dissolve the cholesterol and butylated hydroxytoluene in the heated mixture. Stir until complete dissolution is obtained. Heat about one third of the water to 80-95° C. in a separate vessel and dissolve the preservatives methylparaben and propylparaben in the heated water while stirring. Allow the solution to cool to about 25° C. and then add the AMN082, disodium edetate, sodium chloride, sodium hydroxide and citric acid. Add the remainder of the water and stir to obtain a complete solution. Transfer the organic mixture into the aqueous mixture by means of a vacuum, while homogenizing the combination with a high-shear mixer until a homogeneous product is obtained. Add the hydroxypropyl methylcellulose into the biphasic mixture by means of a vacuum while homogenizing with a mixer. Single bilayered liposomes are formed.

Example 7

Preparation of a Thermoreversible Gel Comprising (S)-Ketamine

| Ingredient | Quantity (mg/g of formulation) |
|---|---|
| (S)-ketamine | 21.0 |
| methylparaben | 2.1 |
| Hypromellose | 21.0 |
| Poloxamer 407 | 378 |
| TRIS HCl buffer (0.1M) | 1677.9 |

A 10-g batch of gel formulation containing 1.0% of (S)-ketamine is prepared by first suspending Poloxamer 407 (BASF Corp.) in TRIS HCl buffer (0.1 M). The Poloxamer 407 and TRIS are mixed under agitation overnight at 4° C. to ensure complete dissolution of the Poloxamer 407 in the TRIS. The hypromellose, methylparaben and additional TRIS HCl buffer (0.1 M) is added. The composition is stirred until dissolution is observed. A solution of (S)-ketamine is added and the composition is mixed until a homogenous gel is produced. The mixture is maintained below room temperature until use.

Example 8

Preparation of a Thermoreversible Gel (S)-Ketamine Composition Comprising Micronized (S)-Ketamine Powder

| Ingredient | Quantity (mg/g of formulation) |
|---|---|
| (S)-Ketamine | 20.0 |
| BHT | 0.002 |
| Poloxamer 407 | 160.0 |
| PBS buffer (0.1M) | 9.0 |

A 10-g batch of gel formulation containing 2.0% of micronized (S)-Ketamine, 13.8 mg of sodium phosphate dibasic dihydrate USP (Fisher Scientific.)+3.1 mg of sodium phosphate monobasic monohydrate USP (Fisher Scientific.)+74 mg of sodium chloride USP (Fisher Scientific.) is dissolved with 8.2 g of sterile filtered DI water and the pH is adjusted to 7.4 with 1 M NaOH. The buffer solution is chilled down and 1.6 g of poloxamer 407 (BASF Corp., containing approximately 100 ppm of BHT) is sprinkled into the chilled PBS solution while mixing, solution is mixed until all the poloxamer is dissolved. The poloxamer is sterile filtered using a 33 mm PVDF 0.22 µm sterile syringe filter (Millipore Corp.) and delivered to 2 mL sterile glass vials (Wheaton) in an aseptic environment, the vials are closed with sterile butyl rubber stoppers (Kimble) and crimped sealed with 13 mm Al seals (Kimble). 20 mg of micronized (S)-ketamine is placed in separate clean depyrogenated vials, the vials are closed with sterile butyl rubber stoppers (Kimble) and crimped sealed with 13 mm Al seals (Kimble), vials are dry heat sterilized (Fisher Scientific Isotemp oven) for 7 hours at 140° C. Before administration for the experiments described herein, 1 mL of the cold poloxamer solution is delivered to a vial containing 20 mg of sterile micronized (S)-ketamine using a 21 G needle (Becton Dickinson) attached to a 1 mL sterile syringe (Becton Dickinson), suspension mixed well by shaking to ensure homogeneity of the suspension. The suspension is then withdrawn with the 21 G syringe and the needle is switched to a 27 G needle for administration.

Example 9

Preparation of a Thermoreversible Gel Micronized AM-101 Composition Comprising a Penetration Enhancer

| Ingredient | Quantity (mg/g of formulation) |
|---|---|
| AM-101 | 20.0 |
| methylparaben | 1.0 |
| Dodecyl maltoside (A3) | 1.0 |
| HPMC | 10.0 |
| Poloxamer 407 | 180.0 |
| TRIS HCl buffer (0.1M) | 789.0 |

A 10-g batch of gel formulation containing 2.0% of micronized AM-101 is prepared by suspending 1.80 g of Poloxamer 407 (BASF Corp.) in 5.00 g of TRIS HCl buffer (0.1 M) and the components are mixed under agitation overnight at 4° C. to ensure complete dissolution. (S)-Ketamine (200.0 mg), hydroxypropylmethylcellulose (100.0 mg), methylparaben (10 mg) and dodecyl maltoside (10 mg) and additional TRIS HCl buffer (0.1 M) (2.89 g) is added and further stirring allowed until complete dissolution is observed. The mixture is maintained below room temperature until use.

Example 10

Effect of pH on Degradation Products for Autoclaved 17% Poloxamer 407NF/2% Otic Agent in PBS Buffer A stock solution of a 17% poloxamer 407/2% otic agent is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% poloxamer 407/2% otic agent in PBS pH of 5.3.

Take an aliquot (approximately 30 mL) of the above solution and adjust the pH to 5.3 by the addition of 1 M HCl.

17% poloxamer 407/2% otic agent in PBS pH of 8.0.

Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of an otic agent in PBS pH 7.3 is prepared by dissolving an appropriate amount of the otic agent in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolved with 1.5 mL of a 1:1 acetonitrile water mixture. Purity of the otic agent in the autoclaved samples is recorded.

Formulations comprising DNQX, D-methionine, micronized AM-101 or micronized (S)-ketamine, prepared according to the procedure above, are tested using the above procedure to determine the effect of pH on degradation during the autoclaving step.

Example 11

Effect of Autoclaving on the Release Profile and Viscosity of a 17% Poloxamer 407NF/2% Otic Agent in PBS An aliquot of a sample (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 μm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 20 μL of the sample is mixed with 1980 μL of a 15 mM cobalt thiocyanate solution and absorbance measured at 625 nm, using a Evolution 160 UV/Vis spectrophotometer (Thermo Scientific).

The released otic agent is fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{-1/n}}{n+1}$$

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Formulations comprising DNQX, D-methionine, micronized AM-101 or micronized (S)-ketamine, prepared according to the procedures described above, are tested using the procedure described above to determine Tgel.

Example 12

Effect of Addition of a Secondary Polymer on the Degradation Products and Viscosity of a Formulation Containing 2% Otic Agent and 17% Poloxamer 407NF after Heat Sterilization (Autoclaving)

Solution A.

A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP @ 2%) is sprinkled into the buffer solution and heated to aid dissolution, and the solution is then cooled down.

A solution of pH 7.0 comprising 17% poloxamer 407NF/1% CMC/2% otic agent in PBS buffer is made by cooling down 8.1 g of solution A in a ice chilled water bath and then adding an appropriate amount of an otic agent followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

Precipitation or discoloration are observed after autoclaving. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolving with 1.5 mL of a 1:1 acetonitrile water mixture. Purity of the otic agent in the autoclaved samples is recorded.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Dissolution is performed at 37° C. for the non-autoclaved sample in snapwells (6.5 mm diameter polycarbonate membrane with a pore size of 0.4 μm), 0.2 mL of gel is placed into snapwell and left to harden, then 0.5 mL is placed into reservoir and shaken using a Labline orbit shaker at 70 rpm. Samples are taken every hour (0.1 mL withdrawn and replaced with warm buffer). Samples are analyzed for otic agent concentration by UV at 245 nm, against an external calibration standard curve.

Formulations comprising DNQX, D-methionine, micronized AM-101 or micronized (S)-ketamine, are tested using the above procedure to determine the effect addition of a secondary polymer on the degradation products and viscosity of a formulation containing 2% otic agent and 17% poloxamer 407NF after heat sterilization (autoclaving).

Example 13

Effect of Buffer Type on the Degradation Products for Formulations Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in TRIS Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved.

A series of formulations is prepared with the above stock solution. An appropriate amount of otic agent (or salt or prodrug thereof) and/or otic agent as micronized/coated/liposomal particles (or salt or prodrug thereof) is used for all experiments.

Stock Solution (pH 7.3) Containing 25% Poloxamer 407 Solution in PBS Buffer:

PBS buffer described above is used. Dissolve 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved.

A series of formulations is prepared with the above stock solution. An appropriate amount of otic agent (or salt or prodrug thereof) and/or otic agent as micronized/coated/liposomal particles (or salt or prodrug thereof) is used for all experiments.

Tables 2 and 3 list samples prepared using the procedures described above. An appropriate amount of otic agent is added to each sample to provide a final concentration of 2% otic agent in the sample.

TABLE 2

Preparation of samples containing TRIS buffer

| Sample | pH | 25% Stock Solution (g) | TRIS Buffer (g) |
| --- | --- | --- | --- |
| 20% P407/2% otic agent/TRIS | 7.45 | 8.01 | 1.82 |
| 18% P407/2% otic agent/TRIS | 7.45 | 7.22 | 2.61 |
| 16% P407/2% otic agent/TRIS | 7.45 | 6.47 | 3.42 |
| 18% P407/2% otic agent/TRIS | 7.4 | 7.18 | 2.64 |
| 4% otic agent/TRIS | 7.5 | — | 9.7 |

TABLE 2-continued

Preparation of samples containing TRIS buffer

| Sample | pH | 25% Stock Solution (g) | TRIS Buffer (g) |
|---|---|---|---|
| 2% otic agent/TRIS | 7.43 | — | 5 |
| 1% otic agent/TRIS | 7.35 | — | 5 |
| 2% otic agent/TRIS (suspension) | 7.4 | — | 4.9 |

TABLE 3

Preparation of samples containing PBS buffer (pH of 7.3)

| Sample | 25% Stock Solution in PBS (g) | PBS Buffer (g) |
|---|---|---|
| 20% P407/2% otic agent/PBS | 8.03 | 1.82 |
| 18% P407/2% otic agent/PBS | 7.1 | 2.63 |
| 16% P407/2% otic agent/PBS | 6.45 | 3.44 |
| 18% P407/2% otic agent/PBS | — | 2.63 |
| 2% otic agent/PBS | — | 4.9 |

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolving with 1.5 mL of a 1:1 acetonitrile water mixture. Purity of the otic agent in the autoclaved samples is recorded. The stability of formulations in TRIS and PBS buffers is compared.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition. Only formulations that show no change after autoclaving are analyzed.

Formulations comprising DNQX, D-methionine, micronized AM-101 or micronized (S)-ketamine, are tested using the above procedure to determine the effect addition of a secondary polymer on the degradation products and viscosity of a formulation containing 2% otic agent and 17% poloxamer 407NF after heat sterilization (autoclaving). Stability of formulations containing micronized otic agent is compared to non-micronized otic agent formulation counterparts.

Example 14

Pulsed Release Otic Formulations

A combination of D-methionine and D-methionine hydrochloride (ratio of 1:1) is used to prepare a pulsed release otic agent formulation using the procedures described herein. 20% of the delivered dose of D-methione is solubilized in a 17% poloxamer solution of example 10 with the aid of beta-cyclodextrins. The remaining 80% of the otic agent is then added to the mixture and the final formulation is prepared using any procedure described herein.

Pulsed release formulations comprising DNQX, D-methionine, micronized AM-101 or micronized (S)-ketamine, prepared according to the procedures and examples described above, are tested using procedures described herein to determine pulse release profiles.

Example 15

Preparation of a 17% Poloxamer 407/2% Otic Agent/78 ppm Evans Blue in PBS

A Stock solution of Evans Blue (5.9 mg/mL) in PBS buffer is prepared by dissolving 5.9 mg of Evans Blue (Sigma Chemical Co) with 1 mL of PBS buffer (from example 10).

A Stock solution containing 25% Poloxamer 407 solution in PBS buffer is used in this study. An appropriate amount of an otic agent is added to the stock solution to prepare formulations comprising 2% of an otic agent (Table 4).

TABLE 4

Preparation of poloxamer 407 samples containing Evans Blue

| Sample ID | 25% P407 in PBS (g) | PBS Buffer (g) | Evans Blue Solution (μL) |
|---|---|---|---|
| 17% P407/2% otic agent/EB | 13.6 | 6 | 265 |
| 20% P407/2% otic agent/EB | 16.019 | 3.62 | 265 |
| 25% P407/2% otic agent/EB | 19.63 | — | 265 |

Formulations comprising DNQX, D-methionine, micronized AM-101 or micronized (S)-ketamine, are prepared according to the procedures described above and are sterile filtered through 0.22 μm PVDF syringe filters (Millipore corporation), and autoclaved.

The above formulations are dosed to guinea pigs in the middle ear by procedures described herein and the ability of formulations to gel upon contact and the location of the gel is identified after dosing and at 24 hours after dosing.

Example 16

Terminal Sterilization of Poloxamer 407 Formulations with and without a Visualization Dye 17% poloxamer 407/2% otic agent/in phosphate buffer, pH 7.3:

Dissolve 709 mg of sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of an otic agent with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved.

17% poloxamer 407/2% otic agent/59 ppm Evans blue in phosphate buffer:

Take two mL of the 17% poloxamer 407/2% otic agent/in phosphate buffer solution and add 2 mL of a 5.9 mg/mL Evans blue (Sigma-Aldrich chemical Co) solution in PBS buffer.

25% poloxamer 407/2% otic agent/in phosphate buffer:

Dissolve 330.5 mg of sodium chloride (Fisher Scientific), 334.5 mg of sodium phosphate dibasic dehydrate USP (Fisher Scientific), 125.9 mg of sodium phosphate monobasic monohydrate USP (Fisher Scientific) and an appropriate amount of an otic agent with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved.

25% poloxamer 407/2% otic agent/59 ppm Evans blue in phosphate buffer:

Take two mL of the 25% poloxamer 407/2% otic agent/in phosphate buffer solution and add 2 mL of a 5.9 mg/mL Evans blue (Sigma-Aldrich chemical Co) solution in PBS buffer.

Place 2 mL of formulation into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed using an Agilent 1200 equipped with a Luna C18(2) 3 µm, 100 Å, 250×4.6 mm column) using a 30-95 methanol:acetate buffer pH 4 gradient (1-6 min), then isocratic for 11 minutes, for a total run of 22 minutes. Samples are diluted by taking 30 µL of sample and dissolved with 0.97 mL of water. The main peaks are recorded in the table below. Purity before autoclaving is always greater than 99% using this method.

Viscosity measurements are performed using a Brookfield viscometer RVDV-II+P with a CPE-51 spindle rotated at 0.08 rpm (shear rate of 0.31 $s^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Formulations comprising DNQX, D-methionine, micronized AM-101 or micronized (S)-ketamine, prepared according to the procedures described herein, are tested using the above procedures to determine stability of the formulations.

Example 17

In Vitro Comparison of Release Profile

Dissolution is performed at 37° C. in snapwells (6.5 mm diameter polycarbonate membrane with a pore size of 0.4 µm), 0.2 mL of a gel formulation described herein is placed into snapwell and left to harden, then 0.5 mL buffer is placed into reservoir and shaken using a Labline orbit shaker at 70 rpm. Samples are taken every hour (0.1 mL withdrawn and replace with warm buffer). Samples are analyzed for otic agent concentration by UV at 245 nm against an external calibration standard curve. Pluronic concentration is analyzed at 624 nm using the cobalt thiocyanate method. Relative rank-order of mean dissolution time (MDT) as a function of % P407 is determined. A linear relationship between the formulations mean dissolution time (MDT) and the P407 concentration indicates that the otic agent is released due to the erosion of the polymer gel (poloxamer) and not via diffusion. A non-linear relationship indicates release of otic agent via a combination of diffusion and/or polymer gel degradation.

Alternatively, samples are analyzed using the method described by Li Xin-Yu paper [Acta Pharmaceutica Sinica 2008, 43(2):208-203] and Rank-order of mean dissolution time (MDT) as a function of % P407 is determined.

Formulations comprising DNQX, D-methionine, micronized AM-101 or micronized (S)-ketamine, prepared according to the procedures described herein, are tested using the above procedure to determine the release profile of the otic agents.

Example 18

In Vitro Comparison of Gelation Temperature

The effect of Poloxamer 188 and an otic agent on the gelation temperature and viscosity of Poloxamer 407 formulations is evaluated with the purpose of manipulating the gelation temperature.

A 25% Poloxamer 407 stock solution in PBS buffer and the PBS solution described above are used. Poloxamer 188NF from BASF is used. An appropriate amount of otic agent is added to the solutions described in Table 5 to provide a 2% formulation of the otic agent.

TABLE 5

Preparation of samples containing poloxamer 407/poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time, viscosity and gel temperature of the above formulations are measured using procedures described herein.

An equation is fitted to the data obtained and can be utilized to estimate the gelation temperature of F127/F68 mixtures (for 17-20% F127 and 0-10% F68).

$$T_{gel} = -1.8(\%F127) + 1.3(\%F68) + 53$$

An equation is fitted to the data obtained and can be utilized to estimate the Mean Dissolution Time (hr) based on the gelation temperature of F127/F68 mixtures (for 17-25% F127 and 0-10% F68), using results obtained in examples above.

$$MDT = -0.2(T_{gel}) + 8$$

Formulations comprising DNQX, D-methionine, micronized AM-101 or micronized (S)-ketamine, are prepared by addition of an appropriate amount of otic agents to the solutions described in Table 5. The gel temperature of the formulations is determined using the procedure described above.

Example 19

Determination of Temperature Range for Sterile Filtration

The viscosity at low temperatures is measured to help guide the temperature range at which the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 $s^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic formulation is estimated by:

$$\Delta T_{gel} = 0.93[\% \text{ otic agent}]$$

Formulations comprising DNQX, D-methionine, micronized AM-101 or micronized (S)-ketamine, prepared according to procedures described herein, are tested using the above procedure to determine the temperature range for sterile filtration. The effect of addition of increased amounts of otic agent on the Tgel, and the apparent viscosity of the formulations is recorded.

Example 20

Determination of Manufacturing Conditions

TABLE 6

Viscosity of potential formulations at manufacturing/filtration conditions.

| | Apparent Viscosity$^a$ (cP) | | |
|---|---|---|---|
| Sample | 5° C. below Tgel | 20° C. | Temperature @ 100 cP |
| Placebo | 52 cP @ 17° C. | 120 cP | 19° C. |
| 17% P407/2% otic agent | 90 cP @ 18° C. | 147 cP | 18.5° C. |
| 17% P407/6% otic agent | 142 cP @ 22° C. | 105 cP | 19.7° C. |

$^a$Viscosity measured at a shear rate of 37.5 s$^{-1}$

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank is taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20 @ 1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm² are evaluated at 20 psi and 14° C. of solution
1) Sartopore 2, 0.2 µm 5445307HS-FF (PES), flow rate of 16 mL/min
2) Sartobran P, 0.2 µm 5235307HS-FF (cellulose ester), flow rate of 12 mL/min
3) Sartopore 2 XLI, 0.2 µm 5445307IS-FF (PES), flow rate of 15 mL/min Sartopore 2 filter 5441307H4-SS is used, filtration is carried out at the solution temperature using a 0.45, 0.2 µm Sartopore 2 150 sterile capsule (Sartorius Stedim) with a surface area of 0.015 m² at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 7

Predicted filtration time for a 17% poloxamer 407 placebo at a solution temperature range of 6.5-14° C. using Sartopore 2, 0.2 µm filters at a pressure of 16 psi of pressure.

| Filter | Size (m²) | Estimated flow rate (mL/min) | Time to filter 8 L (estimated) |
|---|---|---|---|
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption is check before filtration evaluation. Pluronic UV/Vis spectra are obtained by a Evolution 160 UV/Vis (Thermo Scientific). A peak in the range of 250-300 nm is attributed to BHT stabilizer present in the raw material (poloxamer). Table 8 lists physicochemical properties of the above solutions before and after filtration.

TABLE 8

Physicochemical properties of 17% poloxamer 407 placebo solution before and after filtration

| Sample | Tgel (° C.) | Viscosity$^a$ @ 19° C. (cP) | Absorbance @ 274 nm |
|---|---|---|---|
| Before filtration | 22 | 100 | 0.3181 |
| After filtration | 22 | 100 | 0.3081 |

$^a$Viscosity measured at a shear rate of 37.5 s$^{-1}$

The above process is applicable for manufacture of 17% P407 formulations, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 21

In Vitro Release of Otic Agent from an Autoclaved Micronized Sample

17% poloxamer 407/1.5% otic agent in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and an appropriate amount of micronized otic agent is suspended and dispersed well. 2 mL of the formulation is transferred into a 2 mL glass vial (Wheaton serum glass vial) and sealed with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4

μm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance otic agent solubility]. Samples are analyzed for otic agent concentration by UV at 245 nm against an external calibration standard curve. The release rate is compared to other formulations disclosed herein. MDT time is calculated for each sample.

Solubilization of otic agent in the 17% poloxamer system is evaluated by measuring the concentration of the otic agent in the supernatant after centrifuging samples at 15,000 rpm for 10 minutes using an eppendorf centrifuge 5424. Otic agent concentration in the supernatant is measured by UV at 245 nm against an external calibration standard curve.

Formulations comprising DNQX, D-methionine, micronized AM-101 or micronized (S)-ketamine, prepared according to the procedures described herein, are tested using the above procedures to determine release rate of the otic agent from each formulation.

Example 22

Release Rate or MDT and Viscosity of Formulation Containing Sodium Carboxymethyl Cellulose 17% poloxamer 407/2% otic agent/1% CMC (Hercules Blanose 7M):

A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP @ 2%) is sprinkled into the buffer solution and heated to ease solution, solution is then cooled down and 17.08 g poloxamer 407NF (Spectrum Chemicals) is sprinkled into the cold solution while mixing. A formulation comprising 17% poloxamer 407NF/1% CMC/2% otic agent in PBS buffer is made adding/dissolving an appropriate amount of otic agent to 9.8 g of the above solution, and mixing until all the otic agent is completely dissolved.

17% poloxamer 407/2% otic agent/0.5% CMC (Blanose 7M65):

A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP @ 2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 g of the above solution, and mixing until the otic agent is completely dissolved.

17% poloxamer 407/2% otic agent/0.5% CMC (Blanose 7H9):

A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H9 CMC (Hercules, viscosity of 5600 cP @ 1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 of the above solution, and mixing until the otic agent is completely dissolved.

Viscosity measurements are performed using a Brookfield viscometer RVDV-II+P with a CPE-40 spindle rotated at 0.08 rpm (shear rate of 0.6 s$^{-1}$), equipped with a water jacketed temperature control unit (temperature ramped from 10-34° C. at 1.6° C./min). Tgel is defined as the inflection point of the curve where the increase in viscosity occurs due to the sol-gel transition.

Dissolution is performed at 37° C. in snapwells (6.5 mm diameter polycarbonate membrane with a pore size of 0.4 μm). 0.2 mL of gel is placed into snapwell and left to harden, then 0.5 mL PBS buffer is placed into reservoir and shaken using a Labline orbit shaker at 70 rpm. Samples are taken every hour, 0.1 mL withdrawn and replaced with warm PBS buffer. Samples are analyzed for otic agent concentration by UV at 245 nm against an external calibration standard curve. The release rate is compared to the formulations disclosed in above examples, and MDT time is calculated for each of the above formulations.

Formulations comprising DNQX, D-methionine, micronized AM-101 or micronized (S)-ketamine, prepared according to procedures described above, are tested using the above procedures to determine relationship between release rate and/or mean dissolution time and viscosity of formulation containing sodium carboxymethyl cellulose. Any correlation between the mean dissolution time (MDT) and the apparent viscosity (measured at 2° C. below the gelation temperature) is recorded.

Example 23

Effect of Poloxamer Concentration and Otic Agent Concentration on Release Kinetics A series of compositions comprising varying concentrations of a gelling agent and micronized dexamethasone was prepared using procedures described above. The mean dissolution time (MDT) for each composition in Table 9 was determined using procedures described above.

TABLE 9

Preparation of poloxamer/otic agent compositions

| Sample | pH | MDT |
| --- | --- | --- |
| 15.5% P407/1.5% dexamethasone/PBS | 7.4 | 46 h |
| 16% P407/1.5% dexamethasone/PBS | 7.4 | 40 h |
| 17% P407/1.5% dexamethasone/PBS | 7.4 | 39 h |
| 15.5% P407/4.5% dexamethasone/PBS | 7.4 | >7 days |
| 16% P407/4.5% dexamethasone/PBS | 7.4 | >7 days |
| 17% P407/4.5% dexamethasone/PBS | 7.4 | >7 days |

The effect of gel strength and otic agent concentration on release kinetics of an otic agent from the composition or device was determined by measurement of the MDT for poloxamer, and measurement of MDT for otic agent. The half life of the otic agent and mean residence time of the otic agent was also determined for each formulation by measurement of concentration of the otic agent in the perilymph.

The apparent viscosity of each composition was measured as described above. A thermoreversible polymer gel concentration of about 15.5% in a composition or device described above provided an apparent viscosity of about 270,000 cP. A thermoreversible polymer gel concentration of about 16% in a composition or device described above provided an apparent viscosity of about 360,000 cP. A thermoreversible polymer gel concentration of about 17% in a composition or device described above provided an apparent viscosity of about 480,000 cP.

Compositions comprising micronized DNQX, D-methionine, micronized AM-101 or micronized (S)-ketamine, prepared according to the procedures described above, are tested using the above procedure to determine release rate of the otic agent from each composition.

Example 24

Application of an Enhanced Viscosity Auris Sensory Cell Modulating Agent Formulation onto the Round Window Membrane A formulation comprising AM-101 prepared according to Example 8 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the auris sensory cell modulating agent formulation applied directly onto the round-window membrane.

Example 25

In Vivo Testing of Intratympanic Injection of Auris Sensory Cell Modulating Agent Formulation in a Guinea Pig A cohort of 21 guinea pigs (Charles River, females weighing 200-300 g) is intratympanically injected with 50 µL of different P407-otic agent formulations described herein, containing 0 to 50% otic agent. The gel elimination time course for each formulation is determined. A faster gel elimination time course of a formulation indicates lower mean dissolution time (MDT). Thus the injection volume and the concentration of an auris sensory cell modulating agent in a formulation are tested to determine optimal parameters for preclinical and clinical studies.

Example 26

In Vivo Extended Release Kinetics

A cohort of 21 guinea pigs (Charles River, females weighing 200-300 g) is intratympanically injected with 50 µL 17% Pluronic F-127 formulation buffered at 280 mOsm/kg and containing 1.5% to 35% auris sensory cell modulating agent by weight of the formulation. Animals are dosed on day 1. The release profile for the formulations is determined based on analysis of the perilymph.

Example 27

Evaluation of (S)-Ketamine in a Tinnitus Mouse Model

Twelve Harlan Sprague-Dawley mice weighing 20 to 24 g are used. Each mouse is trained to drink from a water dispenser during periods no sound, but to refrain from drinking in the presence of sound. Each mouse is administered 350 mg of aspirin per kilogram of body weight (mg/kg).

The control group (n=10) are administered saline following administration of the aspirin. The experimental group (n=10) are administered (S)-ketamine (400 mg/kg of body weight) following administration of the aspirin. Administration occurs via an intra-tympanic injection.

Following administration of (S)-ketamine whether the mice drink in the absence of external sound is monitored.

Example 28

Evaluation of N-Acetylcysteine (NAC) in a Cisplatin-Induced Ototoxicity Mouse Model Methods and Materials
Induction of Ototoxicity
Twelve Harlan Sprague-Dawley mice weighing 20 to 24 g are used. Baseline auditory brainstem response (ABR) at 4-20 mHz is measured. The mice are treated with cisplatin (6 mg/kg of body weight). The cisplatin is delivered to the aorta by IV infusion.
Treatment
The control group (n=10) are administered saline following administration of the cisplatin. The experimental group (n=10) are administered NAC (400 mg/kg of body weight) following administration of the cisplatin.
Analysis of Results
Electrophysiologic Testing
The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 29

Clinical Trial of (S)-Ketamine as a Treatment for Tinnitus

Active Ingredient: (S)-ketamine
Dosage: 10 ng delivered in 10 µL of a thermoreversible gel. Release of (S)-ketamine is controlled release and occurs over thirty (30) days.
Route of Administration: Intratympanic injection
Treatment Duration: 12 weeks
Methodology
Monocentric
Prospective Randomized
Double-blind
Placebo-controlled
Parallel group
Adaptive
Inclusion Criteria
  Male and female subjects between the 18 and 64 years of age.
  Subjects experiencing subjective tinnitus.
  Duration of tinnitus is greater than 3 months.
  No treatment of tinnitus within 4 weeks.
Evaluation Criteria
  Efficacy (Primary)
    1. Total score of the Tinnitus Questionnaire
  Efficacy (Secondary)
    1. Audiometric measurements (mode, frequency, loudness of the tinnitus, pure tone audiogram, speech audiogram)
    2. Quality of Life questionnaire
  Safety
    1. Treatment groups were compared with respect to incidence rates of premature termination, treatment-emergent adverse events, laboratory abnormalities, and ECG abnormalities.
Study Design
  Subjects are divided into three treatment groups. The first group is the safety sample. The second group is the intent-to-treat (ITT) sample. The third group is the valid for efficacy (VfE) group.
  For each group, one half of subjects to be given (S)-ketamine and the remainder to be given placebo.
Statistical Methods
  The primary efficacy analysis is based on the total score of the Tinnitus Questionnaire in the ITT sample. The statistical analysis is based on an analysis of covariance (ANCOVA) with baseline as covariant and the last observation carried forward value as dependent variable. Factor is "treatment." The homogeneity of regression slopes is tested. The analysis is repeated for the VfE sample.
  Audiometric measurements (mode, frequency, loudness of the tinnitus, pure tone audiogram, speech audiogram) as well as quality of life are also analyzed via the aforementioned model. The appropriateness of the model is not tested. P values are exploratory and are not adjusted for multiplicity.

Example 30

Evaluation of AMN082 on Cisplatin-Induced Ototoxicity

Study Objective
  The primary objective of this study will be to assess the safety and efficacy of AMN082 (100 mg) compared with that of placebo in preventing Cisplatin-induced ototoxicity.
Methods
  Study Design
  This will be a phase 3, multicentre, double-blind, randomised, placebo-controlled, parallel group study comparing AMN082 (100 mg) to placebo in the treatment of Cisplatin-induced ototoxicity. Approximately 140 subjects will be enrolled in this study, and randomised (1:1) to 1 of 2 treatment groups based on a randomisation sequence prepared by sponsor. Each group will receive either AMN082 100 mg or placebo.
  Subjects who do not complete the study will not be replaced. Patients will receive weekly chemotherapy (cisplatin at a dose of 70 mg/m$^2$ for 7 weeks and daily radiation. Following chemotherapy, patients will receive the study drug (AMN082 500 mg or matching placebo) administered as a gel formulation directly onto the subjects' round window membrane for 8 weeks.
  Each patient will receive a hearing evaluation before each treatment with Cisplatin. Two to four weeks after the final dose of Cisplatin, each patient will receive a hearing evaluation. Pre-treatment audiogram will be compared with the post treatment audiogram to determine the degree of cisplatin-induced ototoxicity. Patients will thereafter receive a hearing evaluation at 4-week intervals concomitant with the AMN082 treatment.
  Main Criteria for Inclusion
  Male or female outpatients aged between 18 and 75 years receiving chemotherapy with Cisplatin. Patients expected to receive a minimum of 3 rounds of chemotherapy. If a subject becomes pregnant during the study, she will be immediately withdrawn and no study medication will be administered.
  Exclusion Criteria
  Patients who have had middle ear surgery. Patients who have active external or middle ear disease. Patients who have preceding pure tone average of >40 dB HL.

Example 31

Clinical Trial of AM-101 as a Treatment for Noise Induced Hearing Loss

Active Ingredient: AM-101
Dosage: A composition comprising 4% by weight of micronized AM-101 delivered in 10 µL dose of a thermoreversible gel. Release of AM-101 is controlled release and occurs over 3 weeks.
Route of Administration: Intratympanic injection
Treatment Duration: 12 weeks, one injection every 3 weeks
Methodology
  Monocentric
  Prospective
  Randomized
  Double-blind
  Placebo-controlled
  Parallel group
  Adaptive
Inclusion Criteria
  Male and female subjects between the 18 and 64 years of age.
  Acoustic trauma followed by hearing loss that is documented by audiogram and medical report with an inner ear hearing loss of at least 15 dB
  Acute tinnitus that has persisted for at least 3 months.
  No prior treatment of tinnitus within 4 weeks.
Evaluation Criteria
  Efficacy (Primary)
    1. Total score of the Tinnitus Questionnaire
  Efficacy (Secondary)
    1. Audiometric measurements (mode, frequency, loudness of the tinnitus, pure tone audiogram, speech audiogram)
    2. Quality of Life questionnaire
  Safety
    1. Treatment groups were compared with respect to incidence rates of premature termination, treatment-emergent adverse events, laboratory abnormalities, and ECG abnormalities.
Study Design
  Subjects are divided into three treatment groups. The first group is the safety sample. The second group is the intent-to-treat (ITT) sample. The third group is the valid for efficacy (VfE) group.

For each group, one half of subjects to be given AM-101 and the remainder to be given placebo.

Statistical Methods

The primary efficacy analysis is based on the total score of the Tinnitus Questionnaire in the ITT sample. The statistical analysis is based on an analysis of covariance (ANCOVA) with baseline as covariant and the last observation carried forward value as dependent variable. Factor is "treatment." The homogeneity of regression slopes is tested. The analysis is repeated for the VfE sample.

Audiometric measurements (mode, frequency, loudness of the tinnitus, pure tone audiogram, speech audiogram) as well as quality of life are also analyzed via the aforementioned model. The appropriateness of the model is not tested. P values are exploratory and are not adjusted for multiplicity.

Example 32

Clinical Trial of (S)-Ketamine as a Treatment in Combination with Implantation of a Cochlear Hearing Device Active Ingredient: (S)-ketamine in combination with dexamethasone Dosage: A composition comprising micronized (S)-ketamine and micronized dexamethasone, used as a pre-surgical irrigation solution and a post-surgical irrigation solution. Release of (S)-ketamine and dexamethasone is immediate release.

Study Design

Twenty patients will be enrolled in the study. Ten patients will be in the control group and ten patients will be in the treatment group.

Eligibility Criteria having severe to profound sensorineural hearing impairment in both ears having a functioning auditory nerve having lived at least a short amount of time without hearing (approximately 70+ decibel hearing loss, on average)

having good speech, language, and communication skills, or in the case of infants and young children, having a family willing to work toward speech and language skills with therapy not benefiting enough from other kinds of hearing aids having no medical reason to avoid surgery Each patient will be subjected to chochloestomy and insertion of electrodes. The treatment group will be subjected to perfusion of the surgical area with the test composition prior to surgery and after surgery. The patients will be monitored for 6 weeks. Intracochlear trauma will be evaluated based on audiometric measurements, speech audiogram as well as quality of life. Occurrence of secondary infections and/or inflammation will be monitored.

Example 33

Clinical Trial of Auris Sensory Cell Modulator Formulations in Combination with Surgery The purpose of this study is to determine if a composition comprising a combination of AM-101 and Dexamethasone administered in combination with tympanostomy is safe and effective in preventing and/or treating middle ear infections in patients with ear tubes.

Study Type: Interventional

Study Design: This will be a non-inferiority open label study to compare the current standard of care versus the use of extended release intratympanic compositions in combination with tympanostomy. The current standard of care requires the use of otic drops for 5-7 days post-surgery. The study is designed to test whether administration of a sustained release composition at the time of surgery obviates the need for out-patient treatment. The test hypothesis is that administration of a single injection of an extended release composition at the time of surgery is not inferior to administration of otic drops after surgery.

Inclusion Criteria:

6 months to 12 years old, hearing loss in one or both ears

Patient may not have had otic surgery other than tube placement in the last year Patient may not have any disease or condition that would negatively affect the conduct of the study Patient may not require any other systemic antimicrobial therapy during the study.

Analgesic use (other than acetaminophen) is not allowed

Exclusion Criteria: Age

Study Protocol: Twenty patients will be divided into two groups. The first group of patients will receive an injection of an extended release composition comprising micronized AM-101 and micronized dexamethasone, prepared according to Example 22, during the surgical procedure. Each patient will undergo a tympanostomy for placement of a tube. During the surgical procedure, the surgeon will clean the ear and while the myngotomoy incision is open, the surgeon injects a test composition into the middle ear space. The tube is inserted after injection of the extended release composition into the middle ear space. The test composition is either prepared in the operating room by suspending dry micronized powder of AM-101 and dexamethasone with other excipients, or the test composition is a prepared suspension ready for injection.

The second group of patients will be given ear drops comprising non-micronized AM-101 and non-micronized dexamethasone as immediate release components to be administered for 5-7 days after the surgery.

Patients are monitored with weekly follow up visits for one month. Any differences in treatment outcomes between the two groups are recorded.

Primary Outcome Measures: Time to cessation of otorrhea as recorded by the parent or guardian via a patient.

Secondary Outcome Measures: Clinical cure rate; Microbiological outcome; Treatment failures; Recurrence of disease.

The treatment outcome for each group of patients is compared to determine whether administration of the extended release composition comprising AM-101 and dexamethasone in combination with tympanostomy is no worse than administration of ear drops comprising AM-101 and dexamethasone after surgery for reduction of otorrhea, infections, and/or inflammation associated with tympanostomy.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. A method of alleviating damage to auris sensory cells comprising administering to an individual in need thereof an intratympanic composition comprising a therapeutically effective amount of a multiparticulate non-microencapsulated otoprotectant, wherein the otoprotectant is a non-corticosteroid otoprotectant, and sterile water, q.s., buffered to provide a pH between about 5.5 and about 8.0; wherein the intratympanic composition provides sustained release of the otoprotectant in the ear for a period of at least 5 days following a single administration, and wherein the otoprotectant is a glutamate receptor antagonist.

2. The method of claim 1, wherein the otoprotectant is administered before or during an otic intervention.

3. The method of claim 1, wherein the otoprotectant is administered after an otic intervention.

4. The method of claim 1, wherein the otoprotectant is essentially in the form of micronized particles.

5. The method of claim 1, wherein the glutamate receptor antagonist is 1-aminoadamantane; dextromethorphan; dextrorphan; ibogaine; ifenprodil; (S)-ketamine; (R)-ketamine; memantine; dizocilpine (MK-801); gacyclidine; traxoprodil; D-2-amino-5-phosphonopentanoic acid (D-AP5); 3-((±)-2-carboxypiperazin-4-yl)-propyl-1-phosphonic acid (CPP); conantokin; 7-chlorokynurenate (7-CK); licostinel; nitrous oxide; phencyclidine; riluzole; tiletamine; aptiganel; remacimide; DCKA (5,7-dichlorokynurenic acid); kynurenic acid; 1-aminocyclopropanecarboxylic acid (ACPC); AP7 (2-amino-7-phosphonoheptanoic acid); APV (R-2-amino-5-phosphonopentanoate); CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-propanol; (1S,2S)-1-(4-hydroxy-3-methoxyphenyl)-2-(4-hydroxy-4-phenylpiperidino)-1-propanol; (3R,4S)-3-(4-(4-fluorophenyl)-4-hydroxypiperidin-1-yl)-chroman-4,7-diol; or (1R*,2R*)-1-(4-hydroxy-3-methylphenyl)-2-(4-(4-fluoro-phenyl)-4-hydroxypiperidin-1-yl)-propan-1-ol-mesylate.

6. The method of claim 1, wherein the multiparticulate glutamate receptor antagonist is a multiparticulate NMDA receptor antagonist.

7. The method of claim 6, wherein the NMDA receptor antagonist is an arylcycloalkylamine or a quinazoline.

8. The method of claim 1, wherein the individual is suffering from an otic disorder selected from excitotoxicity, sensorineural hearing loss, noise induced hearing loss, tinnitus, Meniere's disease, endolymphatic hydrops, vestibular neuronitis, and ototoxicity.

9. The method of claim 1, wherein the intratympanic composition further comprises an auris-acceptable viscosity agent selected from poloxamer, hydroxypropyl methylcellulose, hydroxyethyl cellulose, polyvinylpyrrolidone, carboxymethyl cellulose, polyvinyl alcohol, sodium chondroitin sulfate, sodium hyaluronate, acacia (gum arabic), agar, aluminum magnesium silicate, sodium stearate, bladderwrack, bentonite, carbomer, carrageenan, polyacrylic acid polymer, xanthan, cellulose, microcrystalline cellulose (MCC), ceratonia, chitin, carboxymethylated chitosan, chondrus, dextrose, furcellaran, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, poly(hydroxyethyl methacrylate), oxypolygelatin, pectin, polygeline, propylene carbonate, methyl vinyl ether/maleic anhydride copolymer (PVM/MA), poly(methoxyethyl methacrylate), poly(methoxyethoxyethyl methacrylate), hydroxypropyl cellulose, silicon dioxide, hyaluronic acid or its derivatives, alginate hydrogels, poly(glycolic acid), poly-d,l-lactic acid, poly-l-lactic acid, poly (d,l-lactic-co-glycolic acid) (PLGA), or combinations thereof.

10. The method of claim 1, wherein the intratympanic composition further comprises an auris-acceptable viscosity agent selected from carboxymethyl cellulose, polyacrylic acid polymer, hyaluronic acid or its derivatives and PLGA.

11. The method of claim 1, wherein the intratympanic composition further comprises an auris-acceptable viscosity agent selected from carboxymethyl cellulose, polyacrylic acid polymer, and PLGA.

12. The method of claim 1, wherein the rheology of the intratympanic composition is pseudo plastic.

13. The method of claim 1, wherein the intratympanic composition is injectable via a 18-31 gauge needle.

* * * * *

UNITED STATES PATENT AND TRADEMARK OFFICE
CERTIFICATE OF CORRECTION

PATENT NO.         : 8,496,957 B2
APPLICATION NO.    : 12/504553
DATED              : July 30, 2013
INVENTOR(S)        : Jay Lichter et al.

Page 1 of 1

It is certified that error appears in the above-identified patent and that said Letters Patent is hereby corrected as shown below:

In the Specification

Column 1, line 22, please insert the following new heading and paragraph after the first paragraph entitled "CROSS-REFERENCE":

-- JOINT RESEARCH AGREEMENT

The claimed invention was made as a result of activities undertaken within the scope of a joint research agreement between Jay Benjamin Lichter, Benedikt K. Vollrath, Otonomy, Inc., and Avalon Ventures VIII GP, LLC that was in effect on or before the date the invention was made. --

Signed and Sealed this
Twenty-fourth Day of September, 2013

Teresa Stanek Rea
*Deputy Director of the United States Patent and Trademark Office*